(12) United States Patent
Kimchy et al.

(10) Patent No.: US 8,036,731 B2
(45) Date of Patent: Oct. 11, 2011

(54) INGESTIBLE PILL FOR DIAGNOSING A GASTROINTESTINAL TRACT

(75) Inventors: Yoav Kimchy, Haifa (IL); Roni Amrami, Yokneam (IL); Yona Bouskila, Maidenhead (GB); Udi Antebi, Kiryat Bialik (IL); Nick Sidorenko, Acre (IL); Gal Ben-David, Mitzpe Adi (IL); Yoel Zilberstein, Haifa (IL)

(73) Assignee: Spectrum Dynamics LLC, Orangeburg, NY (US)

( * ) Notice: Subject to any disclaimer, the term of this patent is extended or adjusted under 35 U.S.C. 154(b) by 775 days.

(21) Appl. No.: 10/616,301

(22) Filed: Jul. 10, 2003

(65) Prior Publication Data

US 2004/0054278 A1    Mar. 18, 2004

Related U.S. Application Data

(63) Continuation-in-part of application No. 10/240,239, filed as application No. PCT/IL02/00057 on Jan. 22, 2002, which is a continuation-in-part of application No. 09/765,316, filed on Jan. 22, 2001, now abandoned.

(60) Provisional application No. 60/394,936, filed on Jul. 11, 2002.

(51) Int. Cl.
*A61B 6/00* (2006.01)
(52) U.S. Cl. ..................................................... 600/436
(58) Field of Classification Search .................. 600/436, 600/407, 112, 160, 302; 424/464
See application file for complete search history.

(56) References Cited

U.S. PATENT DOCUMENTS

| | | | |
|---|---|---|---|
| 2,776,377 A | 1/1957 | Anger | |
| 3,340,866 A | 9/1967 | Nöller | |
| 3,684,887 A | 8/1972 | Hugonin | |
| 3,690,309 A | 9/1972 | Pluzhnikov et al. | |
| 3,719,183 A | 3/1973 | Schwartz | |
| 3,739,279 A | 6/1973 | Hollis | |
| 3,971,362 A | 7/1976 | Pope et al. | |
| 4,015,592 A | 4/1977 | Bradley-Moore | |
| 4,278,077 A | 7/1981 | Mizumoto | |
| 4,364,377 A | 12/1982 | Smith | |
| 4,521,688 A | 6/1985 | Yin | |
| H12 H | 1/1986 | Bennett et al. | |
| 4,595,014 A * | 6/1986 | Barrett et al. | 600/431 |

(Continued)

FOREIGN PATENT DOCUMENTS

DE    1516429    12/1969

(Continued)

OTHER PUBLICATIONS

Hassan et al., "A Radiotelemetry Pill for the Measurement of Ionising Radiation using a Mercuric Iodide Detector", Jan. 13, 1977, Physics in Medicine and Biology, vol. 23, No. 2, pp. 302-308.*

(Continued)

*Primary Examiner* — Tse Chen
*Assistant Examiner* — Elmer Chao

(57) ABSTRACT

An ingestible device, adapted to travel in the gastrointestinal tract and perform a diagnostic image of tissue therein, is provided. The diagnostic image may comprise diagnostic information as a function of time, or diagnostic information as a function of distance traveled within the gastrointestinal tract. An imaging method by depth calculations is provided, based on the attenuation of photons of different energies, which are emitted from the same source, coupled with position monitoring.

17 Claims, 19 Drawing Sheets

U.S. PATENT DOCUMENTS

| | | | |
|---|---|---|---|
| 4,674,107 A | 6/1987 | Urban et al. | |
| 4,689,041 A | 8/1987 | Corday et al. | |
| 4,689,621 A | 8/1987 | Kleinberg | |
| 4,731,536 A | 3/1988 | Rische et al. | |
| 4,773,430 A | 9/1988 | Porath | |
| 4,828,841 A | 5/1989 | Porter et al. | |
| 4,844,067 A | 7/1989 | Ikada et al. | |
| 4,844,076 A | 7/1989 | Lesho et al. | |
| 4,893,013 A | 1/1990 | Denen et al. | |
| 4,928,250 A | 5/1990 | Greenberg et al. | |
| 4,929,832 A | 5/1990 | Ledley | |
| 4,951,653 A | 8/1990 | Fry et al. | |
| 4,959,547 A | 9/1990 | Carroll et al. | |
| 4,995,396 A | 2/1991 | Inaba et al. | |
| 5,014,708 A | 5/1991 | Hayashi et al. | |
| 5,032,729 A | 7/1991 | Charpak | |
| 5,033,998 A | 7/1991 | Corday et al. | |
| 5,070,878 A | 12/1991 | Denen | |
| 5,088,492 A | 2/1992 | Takayama et al. | |
| 5,119,818 A | 6/1992 | Carroll et al. | |
| 5,151,598 A | 9/1992 | Denen | |
| 5,170,055 A | 12/1992 | Carroll et al. | |
| 5,170,789 A | 12/1992 | Narayan et al. | |
| 5,243,988 A | 9/1993 | Sieben et al. | |
| 5,246,005 A | 9/1993 | Carroll et al. | |
| 5,249,124 A | 9/1993 | DeVito | |
| 5,279,607 A | 1/1994 | Schentag et al. | |
| 5,299,253 A | 3/1994 | Wessels | |
| 5,307,808 A | 5/1994 | Dumoulin et al. | |
| 5,349,190 A | 9/1994 | Hines et al. | |
| 5,383,456 A | 1/1995 | Arnold et al. | |
| 5,386,446 A | 1/1995 | Fujimoto et al. | |
| 5,395,366 A | 3/1995 | D'Andrea | |
| 5,399,868 A | 3/1995 | Jones et al. | |
| 5,415,181 A | 5/1995 | Hogrefe et al. | |
| 5,441,050 A | 8/1995 | Thurston et al. | |
| 5,448,073 A | 9/1995 | Jeanguillaume | |
| 5,475,219 A | 12/1995 | Olson | |
| 5,484,384 A | 1/1996 | Fearnot | |
| 5,489,782 A | 2/1996 | Wernikoff | |
| 5,493,595 A | 2/1996 | Schoolman | |
| 5,519,221 A | 5/1996 | Weinberg | |
| 5,572,999 A | 11/1996 | Funda et al. | |
| 5,579,766 A | 12/1996 | Gray | |
| 5,604,531 A | 2/1997 | Iddan et al. | |
| 5,617,858 A | 4/1997 | Taverna et al. | |
| 5,635,717 A | 6/1997 | Popescu | |
| 5,657,759 A | 8/1997 | Essen-Moller | |
| 5,672,877 A | 9/1997 | Liebig et al. | |
| 5,682,888 A | 11/1997 | Olson et al. | |
| 5,690,691 A | 11/1997 | Chen et al. | |
| 5,694,933 A | 12/1997 | Madden et al. | |
| 5,695,500 A | 12/1997 | Taylor et al. | |
| 5,716,595 A | 2/1998 | Goldenberg | |
| 5,727,554 A | 3/1998 | Kalend et al. | |
| 5,729,129 A | 3/1998 | Acker | |
| 5,732,704 A | 3/1998 | Thurston et al. | |
| 5,744,805 A | 4/1998 | Raylman et al. | |
| 5,784,432 A | 7/1998 | Kurtz et al. | |
| 5,803,914 A | 9/1998 | Ryals et al. | |
| 5,811,814 A | 9/1998 | Leone et al. | |
| 5,821,541 A | 10/1998 | Tumer | |
| 5,833,603 A | 11/1998 | Kovacs et al. | |
| 5,838,009 A | 11/1998 | Plummer et al. | |
| 5,842,977 A | 12/1998 | Lesho et al. | |
| 5,846,513 A | 12/1998 | Carroll et al. | |
| 5,857,463 A | 1/1999 | Thurston et al. | |
| 5,871,013 A | 2/1999 | Wainer et al. | |
| 5,880,475 A | 3/1999 | Oka et al. | |
| 5,891,030 A | 4/1999 | Johnson et al. | |
| 5,900,533 A | 5/1999 | Chou | |
| 5,916,167 A | 6/1999 | Kramer et al. | |
| 5,928,150 A | 7/1999 | Call | |
| 5,932,879 A | 8/1999 | Raylman et al. | |
| 5,939,724 A | 8/1999 | Eisen et al. | |
| 5,961,457 A | 10/1999 | Raylman et al. | |
| 5,984,860 A | 11/1999 | Shan | |
| 5,987,350 A | 11/1999 | Thurston | |
| 5,993,378 A | 11/1999 | Lemelson | |
| 6,002,480 A | 12/1999 | Izatt et al. | |
| 6,072,177 A | 6/2000 | McCroskey et al. | |
| 6,076,009 A * | 6/2000 | Raylman et al. | 600/436 |
| 6,082,366 A | 7/2000 | Andra et al. | |
| 6,107,102 A | 8/2000 | Ferrari | |
| 6,115,635 A | 9/2000 | Bourgeois | |
| 6,129,670 A | 10/2000 | Burdette et al. | |
| 6,132,372 A | 10/2000 | Essen-Moller | |
| 6,135,955 A | 10/2000 | Madden et al. | |
| 6,147,353 A | 11/2000 | Gagnon et al. | |
| 6,173,201 B1 | 1/2001 | Front | |
| 6,205,347 B1 | 3/2001 | Morgan et al. | |
| 6,212,423 B1 | 4/2001 | Krakovitz | |
| 6,236,878 B1 | 5/2001 | Taylor et al. | |
| 6,236,880 B1 * | 5/2001 | Raylman et al. | 600/436 |
| 6,239,438 B1 | 5/2001 | Schubert | |
| 6,240,312 B1 | 5/2001 | Alfano et al. | |
| 6,242,743 B1 | 6/2001 | DeVito | |
| 6,246,901 B1 | 6/2001 | Benaron | |
| 6,261,562 B1 | 7/2001 | Xu et al. | |
| 6,263,229 B1 | 7/2001 | Atalar et al. | |
| 6,271,524 B1 | 8/2001 | Wainer et al. | |
| 6,271,525 B1 | 8/2001 | Majewski et al. | |
| 6,280,704 B1 | 8/2001 | Schutt et al. | |
| 6,310,968 B1 | 10/2001 | Hawkins et al. | |
| 6,324,418 B1 | 11/2001 | Crowley et al. | |
| 6,339,652 B1 | 1/2002 | Hawkins et al. | |
| 6,346,706 B1 | 2/2002 | Rogers et al. | |
| 6,368,331 B1 | 4/2002 | Front et al. | |
| 6,381,349 B1 | 4/2002 | Zeng et al. | |
| 6,392,235 B1 | 5/2002 | Barrett et al. | |
| 6,407,391 B1 | 6/2002 | Mastrippolito et al. | |
| 6,415,046 B1 | 7/2002 | Kerut, Sr. | |
| 6,420,711 B2 | 7/2002 | Tuemer | |
| 6,426,917 B1 | 7/2002 | Tabanou et al. | |
| 6,429,431 B1 | 8/2002 | Wilk | |
| 6,431,175 B1 | 8/2002 | Penner et al. | |
| 6,438,401 B1 | 8/2002 | Cheng et al. | |
| 6,453,199 B1 | 9/2002 | Kobozev | |
| 6,459,925 B1 | 10/2002 | Nields et al. | |
| 6,480,732 B1 | 11/2002 | Tanaka et al. | |
| 6,484,051 B1 | 11/2002 | Daniel | |
| 6,490,476 B1 | 12/2002 | Townsend et al. | |
| 6,510,336 B1 | 1/2003 | Daghighian et al. | |
| 6,516,213 B1 | 2/2003 | Nevo | |
| 6,525,320 B1 | 2/2003 | Juni | |
| 6,525,321 B2 | 2/2003 | Juni | |
| 6,549,646 B1 | 4/2003 | Yeh et al. | |
| 6,560,354 B1 | 5/2003 | Maurer et al. | |
| 6,567,687 B2 | 5/2003 | Front et al. | |
| 6,584,348 B2 * | 6/2003 | Glukhovsky | 600/547 |
| 6,587,710 B1 | 7/2003 | Wainer | |
| 6,592,520 B1 | 7/2003 | Peszynski et al. | |
| 6,602,488 B1 | 8/2003 | Daghighian | |
| 6,607,301 B1 | 8/2003 | Glukhovsky et al. | |
| 6,611,141 B1 | 8/2003 | Schulz et al. | |
| 6,614,453 B1 | 9/2003 | Suri et al. | |
| 6,628,983 B1 | 9/2003 | Gagnon | |
| 6,628,984 B2 | 9/2003 | Weinberg | |
| 6,632,216 B2 * | 10/2003 | Houzego et al. | 604/890.1 |
| 6,633,658 B1 | 10/2003 | Dabney et al. | |
| 6,638,752 B2 | 10/2003 | Contag et al. | |
| 6,643,538 B1 | 11/2003 | Majewski et al. | |
| 6,662,036 B2 | 12/2003 | Cosman | |
| 6,680,750 B1 | 1/2004 | Tournier et al. | |
| 6,697,660 B1 | 2/2004 | Robinson | |
| 6,728,583 B2 | 4/2004 | Hallett | |
| 6,748,259 B1 | 6/2004 | Benaron et al. | |
| 6,766,048 B1 | 7/2004 | Launay et al. | |
| 6,771,802 B1 | 8/2004 | Patt et al. | |
| 6,943,355 B2 | 9/2005 | Shwartz et al. | |
| 6,963,770 B2 | 11/2005 | Scarantino et al. | |
| 7,043,063 B1 | 5/2006 | Noble et al. | |
| 7,142,634 B2 | 11/2006 | Engler et al. | |
| 7,176,466 B2 | 2/2007 | Rousso et al. | |
| 7,187,790 B2 | 3/2007 | Sabol et al. | |
| 7,468,513 B2 | 12/2008 | Charron et al. | |
| 7,490,085 B2 | 2/2009 | Walker et al. | |

| | | |
|---|---|---|
| 2002/0072784 A1 | 6/2002 | Sheppard et al. |
| 2002/0085748 A1 | 7/2002 | Baumberg |
| 2002/0087101 A1 | 7/2002 | Barrick et al. |
| 2002/0099295 A1 | 7/2002 | Gil et al. |
| 2002/0103431 A1 | 8/2002 | Toker et al. |
| 2002/0148970 A1 | 10/2002 | Wong et al. |
| 2002/0168317 A1 | 11/2002 | Daighighian et al. |
| 2002/0183645 A1 | 12/2002 | Nachaliel |
| 2002/0188197 A1 | 12/2002 | Bishop et al. |
| 2003/0001837 A1 | 1/2003 | Baumberg |
| 2003/0013966 A1 | 1/2003 | Barnes et al. |
| 2003/0063787 A1 | 4/2003 | Natanzon et al. |
| 2003/0081716 A1 | 5/2003 | Tumer |
| 2003/0191430 A1 | 10/2003 | D'Andrea et al. |
| 2003/0202629 A1 | 10/2003 | Dunham et al. |
| 2003/0208117 A1 | 11/2003 | Shwartz et al. |
| 2003/0216631 A1 | 11/2003 | Bloch et al. |
| 2004/0003001 A1 | 1/2004 | Shimura |
| 2004/0010397 A1 | 1/2004 | Barbour et al. |
| 2004/0015075 A1 | 1/2004 | Kimchy et al. |
| 2004/0054248 A1 | 3/2004 | Kimchy et al. |
| 2004/0081623 A1 | 4/2004 | Eriksen et al. |
| 2004/0086437 A1 | 5/2004 | Jackson et al. |
| 2004/0101176 A1 | 5/2004 | Mendonca et al. |
| 2004/0116807 A1 | 6/2004 | Amrami et al. |
| 2004/0153128 A1 | 8/2004 | Suresh et al. |
| 2004/0171924 A1 | 9/2004 | Mire et al. |
| 2004/0195512 A1 | 10/2004 | Crosetto |
| 2004/0204646 A1 | 10/2004 | Nagler et al. |
| 2004/0251419 A1 | 12/2004 | Nelson et al. |
| 2005/0020915 A1 | 1/2005 | Belardinelli et al. |
| 2005/0055174 A1 | 3/2005 | David et al. |
| 2005/0205792 A1 | 9/2005 | Rousso et al. |
| 2005/0211909 A1 | 9/2005 | Smith |
| 2005/0215889 A1 | 9/2005 | Patterson, II |
| 2005/0253073 A1 | 11/2005 | Joram et al. |
| 2005/0266074 A1 | 12/2005 | Zilberstein et al. |
| 2006/0074290 A1 | 4/2006 | Chen et al. |
| 2006/0160157 A1 | 7/2006 | Zuckerman |
| 2006/0237652 A1 | 10/2006 | Kimchy et al. |
| 2007/0156047 A1 | 7/2007 | Nagler et al. |
| 2007/0166227 A1 | 7/2007 | Liu et al. |
| 2007/0166277 A1 | 7/2007 | Liu et al. |
| 2007/0194241 A1 | 8/2007 | Rousso et al. |
| 2008/0033291 A1 | 2/2008 | Rousso et al. |
| 2008/0042067 A1 | 2/2008 | Rousso et al. |
| 2008/0128626 A1 | 6/2008 | Rousso et al. |
| 2008/0230705 A1 | 9/2008 | Rousso et al. |
| 2008/0237482 A1 | 10/2008 | Shahar et al. |
| 2008/0260228 A1 | 10/2008 | Dichterman et al. |
| 2008/0260637 A1 | 10/2008 | Dickman |
| 2008/0277591 A1 | 11/2008 | Shahar et al. |
| 2009/0078875 A1 | 3/2009 | Rousso et al. |
| 2009/0152471 A1 | 6/2009 | Rousso et al. |
| 2009/0190807 A1 | 7/2009 | Rousso et al. |
| 2010/0245354 A1 | 9/2010 | Rousso et al. |

FOREIGN PATENT DOCUMENTS

| | | |
|---|---|---|
| DE | 19814199 | 7/1999 |
| DE | 19815362 | 10/1999 |
| EP | 0543626 | 5/1993 |
| EP | 0697193 | 2/1996 |
| EP | 0887661 | 12/1998 |
| GB | 2031142 | 4/1980 |
| JP | 06-109848 | 4/1994 |
| WO | WO 92/00402 | 9/1992 |
| WO | WO 99/03003 | 1/1999 |
| WO | WO 99/30610 | 6/1999 |
| WO | WO 99/39650 | 8/1999 |
| WO | WO 00/10034 | 2/2000 |
| WO | WO 00/31522 | 2/2000 |
| WO | WO 00/22975 | 4/2000 |
| WO | WO 00/18294 | 6/2000 |
| WO | WO 01/89384 | 11/2001 |
| WO | WO 02/58531 | 1/2002 |
| WO | WO 02/16965 | 2/2002 |
| WO | WO 2004/042546 | 5/2004 |
| WO | WO 2005/067383 | 7/2005 |
| WO | WO 2005/104939 | 11/2005 |
| WO | WO 2005/118659 | 12/2005 |
| WO | WO 2005/119025 | 12/2005 |
| WO | WO 2006/042077 | 4/2006 |
| WO | WO 2006/051531 | 5/2006 |
| WO | WO 2006/054296 | 5/2006 |
| WO | WO 2006/075333 | 7/2006 |
| WO | WO 2006/129301 | 12/2006 |
| WO | WO 2007/010534 | 1/2007 |
| WO | WO 2007/010537 | 1/2007 |
| WO | WO 2007/054935 | 5/2007 |
| WO | WO 2007/074467 | 7/2007 |
| WO | WO 2008/010227 | 1/2008 |
| WO | WO 2008/075362 | 6/2008 |

OTHER PUBLICATIONS

Zhang et al., "An Innovative High Efficiency and High Resolution Probe for Prostate Imaging", Jun. 4, 2000, The Journal of Nuclear Medicine, Proceedings of the 47th Annual Meeting, Jun. 4, 2000, p. 18p No. 68.*

Mettler et al, "Essentials of Nuclear Medicine Imaging", Pub.: WB Saunders, Chap. 14.

Piperno et al, "Breast Cancer Screening by Impedance Measurements", *Frontiers Med. Biol. Engng.*, 2(2):11-17, 1990.

Rajshekhar, V., "Continuous Impedance Monitoring During CT-Guided Stereotactic Surgery: Relative Value in Cystic and Solid Lesions", *British Journal of Neurosurgery*, 6:439-444, 1992.

Jessup, JM, "Tumor Markers—Prognostic and Therapeutic Implications for Colorectal Carcinoma", *Surgical Oncology*, 7:139-151, 1998.

Corstens et al, "Nuclear Medicine's Role in Infection and Inflamation", *The Lancet*, 354:765-770, 1999.

Mori et al, "Overexpression of Matrix Metalloproteinase-7mRNA in Human Colon Carcinomas", *Cancer*, 75:1516-1519, 1995.

Erbil et al, "Use and Limitations of Serum Total and Lipid-Bound Sialic Acid Concentrations as Markers for Colorectal Cancer", *Cancer*, 55:404-409, 1985.

Molinolo et al, "Enhanced Tumor Binding Using Immunohistochemical Analyses by Second Generation Anti-Tumor-Associated Glycoprotein 72 Monoclonal Antibodies *versus* Monoclonal Antibody B72.3 in Human Tissue", *Cancer Research*, 50:1291-1298, 1990.

Day et al,. "Localization of Radioiodinated Rat Fibrogen in Transplanted Rat Tumors", *J. Nat. Cancer Inst.*, 23:799-812, 1959.

Jeanguillaume et al. "From the Whole-Body Counting to Imaging: The Computer Aided Collimation Gamma Camera Project (CACAO)", Radiation Projection Dosimetry 89(3-4): 349-352, 2000.

Quartuccia et al. "Computer Assisted Collimation Gama Camera: A New Approach to Imaging Contaminated Tissues", Radiation Projection Dosimetry 89(3-4): 343-348, 2000.

Bromiley et al. "Attenuation Correction in PET Using Consistency Conditions and a Three-Dimensional Template", IEEE Transactions on Nuclear Science, 48(4): 1371-1377, 2001. p. 1376, col. 2, § 2.

Hayakawa et al. "A PET-MRI Registration Technique for PET Studies of the Rat Brain", Nuclear Medicine & Biology, 27: 121-125, 2000. p. 121, col. 1.

Lavallée et al. "Building a Hybrid Patient's Model for Augmented Reality in Surgery: A Registration Problem", Computing in Biological Medicine, 25(2): 149-164, 1995. p. 149-150.

Kojima et al. "Quantitative Planar Imaging Method for Measurement of Renal Activity by Using a Conjugate-Emission Image and Transmission Data", Medical Physics, 27(3): 608-615, 2000. p. 608.

Pardridge et al. "Tracer Kinetic Model of Blood-Brain Barrier Transport of Plasma Protein-Bound Ligands", Journal of Clinical Investigation, 74: 745-752, 1984.

Reutter et al. "Direct Least Squares Estimation of Spatiotemporal Distributions From Dynamic SPECT Projections Using a Spatial Segmentation and Temporal B-Splines", IEEE Transactions on Medical Imaging, 19(5): 434-450, 2000.

Huesman et al. "Kinetic Parameter Estimation From SPECT Cone-Beam Projection Measurements", Physics in Medicine and Biology, 43(4): 973-982, 1998.

Reutter et al. "Kinetic Parameter Estimation From Attenuated Spect Projection Measurements", IEEE Transactions on Nuclear Science, 45(6): 3007-3013, 1998.
Garcia et al. "Accuracy of Dynamic SPECT Acquisition for Tc-99m Teboroxime Myocardial Perfusion Imaging: Preliminary Results", American College of Cardiology, 51st Annual Scientific Session, Atlanta, Georgia, USA, 8 P., 2002.
Communication Pursuant to Article 96(2) EPC Dated Jun. 19, 2006 From the European Patent Office Re.: Application No. 03810570.6.
Communication pursuant to Article 96(2) EPC Dated Aug. 30, 2007 From the European Patent Office Re.: Application No. 03810570.6.
Communication Relating to the Results of the Partial International Search Dated Apr. 18, 2007 From the International Searching Authority of the Patent Cooperation Treaty Re.: Application No. PCT/IL2006/001291.
Communication Relating to the Results of the Partial International Search Dated May 21, 2008 From the International Searching Authority of the Patent Cooperation Treaty Re.: Application No. PCT/IL2007/001588.
International Search Report Dated Jul. 11, 2008 From the International Searching Authority of the Patent Cooperation Treaty Re.: Application No. PCT/IL06/01511.
International Search Report May 24, 2007 From the International Searching Authority of the Patent Cooperation Treaty Re.: Application No. PCT/IL05/00575.
International Search Report Dated Nov. 1, 2007 From the International Searching Authority of the Patent Cooperation Treaty Re.: Application No. PCT/IL06/00840.
International Search Report Dated Jul. 25, 2008 From the International Searching Authority of the Patent Cooperation Treaty Re.: Application No. PCT/IL2007/001588.
International Search Report Dated Feb. 1, 2006 From the International Searching Authority of the Patent Cooperation Treaty Re.: Application No. PCT/IL05/00048.
International Search Report Dated Jul. 1, 2008 From the International Searching Authority of the Patent Cooperation Treaty Re.: Application No. PCT/IL06/00834.
International Search Report Dated Jul. 2, 2007 From the International Searching Authority of the Patent Cooperation Treaty Re.: Application No. PCT/IL2006/001291.
International Search Report Dated Aug. 3, 2006 From the International Searching Authority of the Patent Cooperation Treaty Re.: Application No. PCT/IL05/001173.
International Search Report Dated May 11, 2006 From the International Searching Authority of the Patent Cooperation Treaty Re.: Application No. PCT/IL05/001215.
International Search Report Dated Sep. 11, 2002 From the International Searching Authority of the Patent Cooperation Treaty Re.: Application No. PCT/IL01/00638.
International Search Report Dated Mar. 18, 2004 From the International Searching Authority of the Patent Cooperation Treaty Re.: Application No. PCT/IL03/00917.
International Search Report Dated Mar. 23, 2006 From the International Searching Authority of the Patent Cooperation Treaty Re.: Application No. PCT/IL05/00572.
International Search Report Dated Mar. 26, 2007 From the International Searching Authority of the Patent Cooperation Treaty Re.: Application No. PCT/IL05/00394.
Official Action Dated Dec. 2, 2007 From the Israeli Patent Office Re.: Application No. 158442.
Official Action Dated Jun. 1, 2006 From the United States Patent and Trademark Office Re.: U.S. Appl. No. 10/686,536.
Official Action Dated May 3, 2007 From the United States Patent and Trademark Office Re.: U.S. Appl. No. 10/616,301.
Official Action Dated Sep. 4, 2008 From the United States Patent and Trademark Office Re.: U.S. Appl. No. 10/533,568.
Official Action Dated Sep. 5, 2008 From the United States Patent and Trademark Office Re.: U.S. Appl. No. 12/084,559.
Official Action Dated Oct. 7, 2008 From the United States Patent and Trademark Office Re.: U.S. Appl. No. 10/616,301.
Official Action Dated Aug. 10, 2007 From the United States Patent and Trademark Office Re.: U.S. Appl. No. 10/836,223.
Official Action Dated Jul. 12, 2007 From the United States Patent and Trademark Office Re.: U.S. Appl. No. 10/616,301.
Official Action Dated Dec. 13, 2007 From the United States Patent and Trademark Office Re.: U.S. Appl. No. 10/616,301.
Official Action Dated Dec. 15, 2006 From the US Patent Office Re.: U.S. Appl. No. 10/616,301.
Official Action Dated Apr. 15, 2008 From the United States Patent and Trademark Office Re.: U.S. Appl. No. 09/641,973.
Official Action Dated Feb. 15, 2008 From the United States Patent and Trademark Office Re.: U.S. Appl. No. 10/343,972.
Official Action Dated Jul. 15, 2008 From the United States Patent and Trademark Office Re.: U.S. Appl. No. 09/641,973.
Official Action Dated Mar. 15, 2004 From the United States Patent and Trademark Office Re.: U.S. Appl. No. 09/725,316.
Official Action Dated Jan. 17, 2006 From the United States Patent and Trademark Office Re.: U.S. Appl. No. 11/034,007.
Official Action Dated Jul. 17, 2007 From the Israeli Patent Office Re.: Application No. 154323.
Official Action Dated Apr. 20, 2006 From the United States Patent and Trademark Office Re.: U.S. Appl. No. 10/240,239.
Official Action Dated Mar. 21, 2008 From the United States Patent and Trademark Office Re.: U.S. Appl. No. 10/533,568.
Official Action Dated Jun. 23, 2006 From the United States Patent and Trademark Office Re.: U.S. Appl. No. 09/727,464.
Official Action Dated Jun. 25, 2008 From the US Patent and Trademark Office Re.: U.S. Appl. No. 10/616,301.
Official Action Dated Sep. 25, 2006 From the US Patent and Trademark Office Re.: U.S. Appl. No. 10/616,301.
Official Action Dated Sep. 30, 2008 From the US Patent and Trademark Office Re.: U.S. Appl. No. 10/616,301.
Supplementary European Search Report Dated Dec. 12, 2005 From the European Patent Office Re.: Application No. 03810570.6.
Supplementary Partial European Search Report Dated Nov. 11, 2008 From the European Patent Office Re.: Application No. 01951883.6.
Written Opinion Dated Feb. 1, 2006 From the International Searching Authority of the Patent Cooperation Treaty Re.: Application No. PCT/IL05/00048.
Written Opinion Dated Jul. 1, 2008 From the International Searching Authority of the Patent Cooperation Treaty Re.: Application No. PCT/IL06/00834.
Written Opinion Dated Oct. 10, 2006 From the International Searching Authority of the Patent Cooperation Treaty Re.: Application No. PCT/IL06/00059.
Written Opinion Dated Jul. 2, 2007 From the International Searching Authority of the Patent Cooperation Treaty Re.: Application No. PCT/IL2006/001291.
Written Opinion Dated Mar. 23, 2006 From the International Searching Authority of the Patent Cooperation Treaty Re.: Application No. PCT/IL05/00572.
Written Opinion Dated May 24, 2007 From the International Searching Authority of the Patent Cooperation Treaty Re.: Application No. PCT/IL05/00575.
Written Opinion Dated Jul. 25, 2008 From the International Searching Authority of the Patent Cooperation Treaty Re.: Application No. PCT/IL05/001173.
Written Opinion Dated Mar. 26, 2007 From the International Searching Authority of the Patent Cooperation Treaty Re.: Application No. PCT/IL05/00394.
Gugnin et al "Radiocapsule for Recording the Ionizing Radiation in the Gastrointestinal Tract", UDC 615. 417:616.34-005.1-073.916-71 (All-Union Scientific-Research Institute of medical Instrument Design, Moscow. Translated from Meditsinskaya Tekhnika, 1:21-25, Jan.-Feb. 1972).
Stoddart et al. "New Multi-Dimensional Reconstructions for the 12-Detector, Scanned Focal Point, Single-Photon Tomograph", Physics in Medicine and Biology, XP020021960, 37(3): 579-586, Mar. 1, 1992. p. 582, § 2-p. 585, § 1.
Official Action Dated Jan. 7, 2009 From the US Patent and Trademark Office Re.: U.S. Appl. No. 10/616,307.
Summons to Attend Oral Proceedings Pursuant to Rule 115(1) EPC Dated Jan. 16, 2009 From the European Patent Office Re.: Application No. 03810570.6.

Supplementary Partial European Search Report Dated Sep. 4, 2007 From the European Patent Office Re.: Application No. 0 2716285.8.
Supplementary Partial European Search Report Dated Nov. 20, 2007 From the European Patent Office Re.: Application No. 02716285.8.
Kinahan et al. "Attenuation Correction for a Combined 3D PET/CT Scanner", Medical Physics, 25(10): 2046-2053, Oct. 1998.
Takahashi et al. "Attenuation Correction of Myocardial SPECT Images With X-Ray CT: Effects of Registration Errors Between X-Ray CT and SPECT", Annals of Nuclear Medicine, 16(6): 431-435, Sep. 2002.
Yu et al. "Using Correlated CT Images in Compensation for Attenuation in PET Image Reconstruction", Proceedings of the SPIE, Applications of Optical Engineering: Proceedings of OE/Midwest '90, 1396: 56-58, 1991.
Zaidi et al. "Magenetic Resonance Imaging-Guided Attenuation and Scatter Corrections in Three-Dimensional Brain Positron Emission Tomography", Medical Physics, 30(5): 937-948, May 2003.
Zaidi et al. "MRI-Guided Attenuation Correction in 3D Brain PET", Neuroimage Human Brain Mapping 2002 Meeting, 16(2): Abstract 504, Jun. 2002.
Final OA dated Jul. 12, 2007.
Invitation to Pay Additional Fees.
Invitation to pay additional fees dated Apr. 18, 2007.
OA dated Sep. 4, 2008.
OA of Jun. 1, 2006.
OA of Aug. 10, 2007.
OA of Jan. 17, 2006.
OA of Jun. 19, 2006.
OA of Dec. 2, 2007.
OA of Jan. 7, 2009.
Official Action Dated May 3, 2007 From the US Patent and Trademark Office Re.: U.S. Appl. No. 10/240,239.
Official Action Dated Oct. 7, 2008 From the US Patent and Trademark Office Re.: U.S. Appl. No. 10/616,301.
Official Action Dated Apr. 15, 2008 From the US Patent and Trademark Office Re.: U.S. Appl. No. 09/727,464.
Official Action Dated Dec. 15, 2006 From the US Patent and Trademark Office Re.: U.S. Appl. No. 10/616,301.
Official Action Dated Feb. 15, 2008 From the US Patent and Trademark Office Re.: U.S. Appl. No. 10/343,792.
Official Action Dated Jul. 15, 2008 From the US Patent and Trademark Office Re.: U.S. Appl. No. 10/641,973.
Official Action Dated Apr. 20, 2006 From the US Patent and Trademark Office Re.: U.S. Appl. No. 10/240,239.
Official Action Dated Dec. 23, 20078 From the US Patent and Trademark Office Re.: U.S. Appl. No. 09/727,464.
Official Action Dated Jun. 23, 2006 From the US Patent and Trademark Office Re.: U.S. Appl. No. 09/727,464.
International Preliminary Report on Patentability Dated Apr. 16, 2009 From the International Bureau of WIPO Re.: Applicaiton No. PCT/IL2007/000918.
International Preliminary Report on Patentability Dated Jun. 21, 2007 From the International Bureau of WIPO Re.: Applicaiton No. PCT/IL2005/000575.
International Preliminary Report on Patentability Dated Jan. 22, 2009 From the International Bureau of WIPO Re.: Applicaiton No. PCT/IL2006/000834.
International Preliminary Report on Patentability Dated Jan. 22, 2009 From the International Bureau of WIPO Re.: Applicaiton No. PCT/IL2006/001511.
International Preliminary Report on Patentability Dated May 22, 2007 From the International Preliminary Examining Authority Re.: Applicaiton No. PCT/IL06/00059.
International Preliminary Report on Patentability Dated May 22, 2008 From the International Bureau of WIPO Re.: Applicaiton No. PCT/IL2006/001291.
International Preliminary Report on Patentability Dated May 24, 2007 From the International Bureau of WIPO Re.: Applicaiton No. PCT/IL2005/001173.
International Preliminary Report on Patentability Dated Apr. 26, 2007 From the International Bureau of WIPO Re.: Applicaiton No. PCT/IL2005/000394.
International Preliminary Report on Patentability Dated Jan. 31, 2008 From the International Bureau of WIPO Re.: Applicaiton No. PCT/IL2006/000840.
International Search Report Dated Sep. 12, 2002 from the International Searching Authority of the Patent Cooperation Treaty Re: Application No. PCT/IL02/00057.
International Search Report Dated Oct. 15, 2008 From the International Searching Authority Re.: Application NO. PCT/IL07/00918.
Invitation to Pay Additional Fees Dated Jul. 10, 2008 From the International Searching Authority Re.: Application No. PCT/IL06/01511.
Invitation to Pay Additional Fees Dated Feb. 15, 2007 From the International Searching Authority Re.: Application No. PCT/IL05/00575.
Official Action Dated Dec. 16, 2008 From the US Patent and Trademark Office Re.: U.S. Appl. No. 10/343,792.
Official Action Dated Dec. 23, 2008 From the US Patent and Trademark Office Re.: U.S. Appl. No. 09/727,464.
Official Action Dated Nov. 26, 2008 From the US Patent and Trademark Office Re.: U.S. Appl. No. 10/240,239.
Official Action Dated Apr. 29, 2009 From the US Patent and Trademark Office Re.: U.S. Appl. No. 11/980,690.
Response Dated Aug. 14, 2008 to Official Action of Apr. 15, 2008 From the US Patent and Trademark Office Re.: U.S. Appl. No. 09/727,464.
Response Dated Nov. 25, 2005 to Official Action of May 13, 2005 From the Patent Office of the People's Republic of China Re.: Application 1817689.5.
Response to the International Search Report and the Written Opinion of Oct. 10, 2006 From the International Searching Authority Re.: Application No. PCT/IL06/00059.
Translation of Office Action Dated May 13, 2005 From the Patent Office of the People's Republic of China Re.: Application No. 01817689.5.
Written Opinion Dated Oct. 15, 2008 From the International Searching Authority Re.: Application No. PCT/IL07/00918.
Communication Pursuant to Article 94(3) EPC Dated Oct. 21, 2009 From the European Patent Office Re.: Application No. 02716285.8.
Official Action Dated Dec. 8, 2009 From the US Patent and Trademark Office Re.: U.S. Appl. No. 11/132,320.
Official Action Dated Oct. 30, 2009 From the US Patent and Trademark Office Re.: U.S. Appl. No. 11/980,690.
Response Dated Dec. 10, 2009 to Official Action of Aug. 11, 2009 From the US Patent and Trademark Office Re.: U.S. Appl. No. 09/641,973.
Response Dated Nov. 16, 2009 to Official Action of Jul. 15, 2009 From the US Patent and Trademark Office Re.: U.S. Appl. No. 10/616,301.
Response Dated Dec. 30, 2009 to Official Action of Sep. 1, 2009 From the US Patent and Trademark Office Re.: U.S. Appl. No. 11/794,799.
Communication Pursuant to Article 94(3) EPC Dated Jul. 22, 2009 From the European Patent Office Re.: Application No. 06809851.6.
Notice of Allowance Dated Jul. 16, 2009 From the US Patent and Trademark Office Re.: U.S. Appl. No. 12/084,559.
Official Action Dated Jul. 7, 2009 From the US Patent and Trademark Office Re.: U.S. Appl. No. 10/533,568.
Official Action Dated Jul. 20, 2009 From the US Patent and Trademark Office Re.: U.S. Appl. No. 11/980,617.
Ogawa et al. "Ultra High Resoultion Pinhole SPECT", IEEE Nuclear Science Symposium, 2: 1600-1604, 1998.
Pellegrini et al. "Design of Compact Pinhole SPECT System Based on Flat Panel PMT", IEEE Nuclear Science Symposium Conference Record, 3: 1828-1832, 2003.
Wu et al. "ECG-Gated Pinhole SPECT in Mice With Millimeter Spatial Resolution", IEEE Transactions on Nuclear Science, 47(3): 1218-1221, Jun. 2000.
Second International Search Report Dated Jun. 1, 2009 From the International Searching Authority Re.: Application No. PCT/IL07/00918.
Second Written Opinion Dated Jun. 1, 2009 From the International Searching Authority Re.: Application No. PCT/IL07/00918.

Response Dated May 11, 2010 to Official Action of Mar. 11, 2010 From the US Patent and Trademark Office Re.: U.S. Appl. No. 11/607,075.
Response Dated May 26, 2010 to Official Action of Mar. 19, 2010 From the US Patent and Trademark Office Re.: U.S. Appl. No. 10/240,239.
Communication Pursuant to Article 94(3) EPC Dated Apr. 16, 2010 From the European Patent Office Re. Application No. 01951883.6.
Appeal Brief Dated Jan. 19, 2010 to Notice of Appeal of Nov. 16, 2009 From the US Patent and Trademark Office Re.: U.S. Appl. No. 10/616,301.
Communication Pursuant to Article 94(3) EPC Dated Mar. 8, 2010 From the European Patent Office Re.: Application No. 06832278.3.
International Search Report Dated Sep. 12, 2002 From the International Searching Authority of the Patent Cooperation Treaty Re: Application No. PCT/IL02/00057.
Notice of Allowance Dated Sep. 17, 2009 From the US Patent and Trademark Office Re.: U.S. Appl. No. 10/533,568. Suppl. IDS VIII in 25855.
Notice of Allowance Dated Nov. 23, 2009 From the US Patent and Trademark Office Re.: U.S. Appl. No. 12/084,559.
Notice of Appeal and Pre-Appeal Brief Dated Jan. 4, 2010 to Official Action of Sep. 2, 2009 From the US Patent and Trademark Office Re.: U.S. Appl. No. 10/343,792.
Notice of Appeal Dated Nov. 16, 2009 to Official Action of Jul. 15, 2009 From the US Patent and Trademark Office Re.: U.S. Appl. No. 10/616,301.
Office Action Dated Jan. 2, 2006 From the Israeli Patent Office Re.: Application No. 154323.
Office Action Dated Sep. 4, 2007 From the Israeli Patent Office Re.: Application No. 157007.
Official Action Dated Mar. 1, 2010 From the US Patent and Trademark Office Re.: U.S. Appl. No. 11/794,799.
Official Action Dated Sep. 1, 2009 From the US Patent and Trademark Office Re.: U.S. Appl. No. 11/794,799.
Official Action Dated Jul. 2, 2004 From the US Patent and Trademark Office Re.: U.S. Appl. No. 09/641,973.
Official Action Dated Mar. 2, 2010 From the US Patent and Trademark Office Re.: U.S. Appl. No. 10/836,223.
Official Action Dated Mar. 2, 2010 From the US Patent and Trademark Office Re.: U.S. Appl. No. 11/980,617.
Official Action Dated Sep. 2, 2009 From the US Patent and Trademark Office Re.: U.S. Appl. No. 10/343,792.
Official Action Dated Jan. 8, 2010 From the US Patent and Trademark Office Re.: U.S. Appl. No. 11/656,548.
Official Action Dated Aug. 11, 2009 From the US Patent and Trademark Office Re.: U.S. Appl. No. 09/641,973.
Official Action Dated Mar. 11, 2010 From the US Patent and Trademark Office Re.: U.S. Appl. No. 11/607,075.
Official Action Dated May 13, 2009 From the US Patent and Trademark Office Re.: U.S. Appl. No. 11/798,017.
Official Action Dated May 14, 2009 From the US Patent and Trademark Office Re.: U.S. Appl. No. 11/656,548.
Official Action Dated Sep. 15, 2009 From the US Patent and Trademark Office Re.: U.S. Appl. No. 10/616,307.
Official Action Dated Sep. 15, 2009 From the US Patent and Trademark Office Re.: U.S. Appl. No. 10/836,223.
Official Action Dated Dec. 16, 2008 From the US Patent and Trademark Office Re.: U.S. Appl. No. 10/343,792.
Official Action Dated Sep. 16, 2009 From the US Patent and Trademark Office Re.: U.S. Appl. No. 09/727,464.
Official Action Dated Mar. 19, 2010 From the US Patent and Trademark Office Re.: U.S. Appl. No. 10/240,239.
Official Action Dated Sep. 21, 2009 From the US Patent and Trademark Office Re.: U.S. Appl. No. 11/798,017.
Official Action Dated Feb. 23, 2010 From the US Patent and Trademark Office Re.: U.S. Appl. No. 09/641,973.
Official Action Dated Aug. 28, 2009 From the US Patent and Trademark Office Re.: U.S. Appl. No. 10/240,239.
Response Dated Oct. 12, 2009 to Notice of Allowance of Jul. 16, 2009 From the US Patent and Trademark Office Re.: U.S. Appl. No. 12/084,559.
Response Dated Jan. 14, 2009 to Official Action of Sep. 15, 2009 From the US Patent and Trademark Office Re.: U.S. Appl. No. 10/616,307.
Response Dated Jan. 14, 2009 to Official Action of Sep. 15, 2009 From the US Patent and Trademark Office Re.: U.S. Appl. No. 10/836,223.
Response Dated Oct. 14, 2009 to Official Action of May 14, 2009 From the US Patent and Trademark Office Re.: U.S. Appl. No. 11/656,548.
Response Dated Jan. 21, 2010 to Official Action of Sep. 21, 2009 From the US Patent and Trademark Office Re.: U.S. Appl. No. 11/798,017.
Response Dated Feb. 22, 2010 to Communication Pursuant to Article 94(3) EPC of Oct. 21, 2009 From the European Patent Office Re.: Application No. 02716285.8.
Response Dated Dec. 28, 2009 to Official Action of Aug. 29, 2009 From the US Patent and Trademark Office Re.: U.S. Appl. No. 10/240,239.
Response Dated Dec. 30, 2009 to Official Action of Oct. 30, 2009 From the US Patent and Trademark Office Re.: U.S. Appl. No. 11/980,690.
Supplementary Partial European Search Report and the European Search Opinion Dated Dec. 15, 2009 From the European Patent Office Re.: Application No. 06832278.3.
Supplementary Partial European Search Report and the European Search Opinion Dated Oct. 16, 2009 From the European Patent Office Re.: Application No. 06756259.5.
Bloch et al. "Application of Computerized Tomography to Radiation Therapy and Surgical Planning", Proceedings of the IEEE, 71(3): 351-355, Mar. 1983.
Gilland et al. "A 3D Model of Non-Uniform Attenuation and Detector Response for Efficient Iterative Reconstruction in SPECT", Physics in Medicine and Biology, XP002558623, 39(3): 547-561, Mar. 1994. p. 549-550, Section 2.3 'Active Voxel Reconstruction', p. 551, Lines 4-8.
Gilland et al. "Simultaneous Reconstruction and Motion Estimation for Gated Cardiac ECT", IEEE Transactions on Nuclear Science, XP011077797, 49(5): 2344-2349, Oct. 1, 2002. p. 2344, Section 'Introduction', First §.
Kadrmas et al. "Static Versus Dynamic Teboroxime Myocardial Perfusion SPECT in Canines", IEEE Transactions on Nuclear Science, 47(3): 1112-1117, Jun. 2000.
Li et al. "A HOTLink/Networked PC Data Acquisition and Image Reconstruction System for a High Resolution Whole-Body PET With Respiratory or ECG-Gated Performance", IEEE Nuclear Sience Symposium and Medical Imaging Conference, Norfolk, VA, USA, Nov. 10-16, 2002, XP010663724, 2: 1135-1139, Nov. 10, 2002. p. 1137, First col. 2nd §.
Moore et al. "Quantitative Multi-Detector Emission Computerized Tomography Using Iterative Attenuation Compensation", Journal of Nuclear Medicine, XP002549083, 23(8): 706-714, Aug. 1982. Abstract, p. 707, Section 'The Multi-Detector Scanner', First §.
Qi et al. "Resolution and Noise Properties of MAP Reconstruction for Fully 3-D PET", IEEE Transactions on Medical Imaging, XP002549082, 19(5): 493-506, May 2000. p. 493, col. 2, Lines 10-21, p. 495, col. 1, Last §.
Wilson et al. "Non-Stationary Noise Characteristics for SPECT Images", Proceedings of the Nuclear Science Symposium and Medical Imaging Conference, Santa Fe, CA, USA, Nov. 2-9, 1991, XP010058168, p. 1736-1740, Nov. 2, 1991. p. 1736, col. 2, Lines 4-6.
Official Action Dated Apr. 9, 2010 From the US Patent and Trademark Office Re.: U.S. Appl. No. 11/798,017.
Communication Pursuant to Article 93(3) EPC Dated Mar. 8, 2010 From the European Patent Office Re.: Application No. 06832278.3.
International Search Report Dated Oct. 10, 2006 From the International Searching Authority of the Patent Cooperation Treaty Re.: Application No. PCT/IL06/00059.
Written Opinion Dated Aug. 3, 2006 From the International Searching Authority of the Patent Cooperation Treaty Re.: Application No. PCT/IL05/001173.
Response Dated Jun. 3, 2010 to Notice of Appeal and Pre-Appeal Brief of Jan. 4, 2010 to Official Action of Sep. 2, 2009 From the US Patent and Trademark Office Re.: U.S. Appl. No. 10/343,792.

Response Dated Jul. 1, 2010 to Official Action of Mar. 2, 2010 From the US Patent and Trademark Office Re.: U.S. Appl. No. 11/980,617.
Response Dated Jun. 1, 2010 to Official Action of Mar. 1, 2010 From the US Patent and Trademark Office Re.: U.S. Appl. No. 11/794,799.
Response Dated Jul. 8, 2010 to Communication Pursuant to Article 94(3) EPC of Mar. 8, 2010 From the European Patent Office Re.: Application No. 06832278.3.
Official Action Jul. 19, 2010 From the US Patent and Trademark Office Re.: U.S. Appl. No. 11/607,075.
Official Action Dated Jul. 19, 2010 From the US Patent and Trademark Office Re.: U.S. Appl. No. 11/656,548.
Response Dated Jul. 1, 2010 to Official Action of Mar. 2, 2010 From the US Patent and Trademark Office Re.: U.S. Appl. No. 10/836,223.
Response Dated Jul. 8, 2010 to Official Action of Apr. 9, 2010 From the US Patent and Trademark Office Re.: U.S. Appl. No. 11/798,017.
Response Dated Jun. 23, 2010 to Official Action of Feb. 23, 2010 From the US Patent and Trademark Office Re.: U.S. Appl. No. 09/641,973.
Official Action Jul. 27, 2010 From the US Patent and Trademark Office Re.: U.S. Appl. No. 10/616,307.
Notice of Allowance Dated Jun. 30, 2010 From the United States Patent and Trademark Office Re.: U.S. Appl. No. 09/727,464.
Official Action Aug. 3, 2010 From the US Patent and Trademark Office Re.: U.S. Appl. No. 11/980,690.
Supplemental Response After Interview Dated Aug. 4, 2010 to Official Action of Mar. 2, 2010 From the US Patent and Trademark Office Re.: U.S. Appl. No. 11/980,617.
Notice of Allowance Dated Jul. 22, 2010 From the United States Patent and Trademark Office Re.: U.S. Appl. No. 11/794,799.
Response Dated Aug. 16, 2010 to Communication Pursuant to Article 94(3) EPC of Apr. 16, 2010 From the European Patent Office Re. Application No. 01951883.6.
Supplemental Response Under 37 C.F.R. § 1.125 Dated Aug. 12, 2010 to Telephonic Interview of Aug. 6, 2010 From the US Patent and Trademark Office Re. U.S. Appl. No. 11/980,617.
Response Dated Aug. 25, 2010 to Official Action of Jul. 27, 2010 From the US Patent and Trademark Office Re.: U.S. Appl. No. 10/616,307.
Communication Pursuant to Article 94(3) EPC Dated May 12, 2010 From the European Patent Office Re.: Application No. 06809851.6.
Notice of Allowance Dated Aug. 25, 2010 From the US Patent and Trademark Office Re.: U.S. Appl. No. 11/980,617.
Response Dated Sep. 8, 2010 to Communication Pursuant to Article 94(3) EPC Dated May 12, 2010 From the European Patent Office Re.: Application No. 06809851.6.
Amendment After Allowance Under 37 CFR 1.312 Dated Sep. 13, 2010 to Notice of Allowance of Jul. 22, 2010 From the US Patent and Trademark Office Re.: U.S. Appl. No. 11/794,799.
Official Action Dated Jan. 31, 2011 From the US Patent and Trademark Office Re. U.S. Appl. No. 11/667,793.
Amendment After Allowance Under 37 CFR 1.312 Dated Sep. 13, 2010 to Notice of Allowance of Jul. 22, 2010 From the US Patent and Trademark Office Re.: U.S. Appl. No. 11/794,799.
International Search Report Dated May 24, 2007 From the International Searching Authority of the Patent Cooperation Treaty Re.: Application No. PCT/IL05/00575.
Office Action Dated Dec. 2, 2007 From the Israeli Patent Office Re.: Application No. 158442.
Office Action Dated Jul. 17, 2007 From the Israeli Patent Office Re.: Application No. 154323.
Official Action Dated Jun. 1, 2006 From the US Patent and Trademark Office Re.: U.S. Appl. No. 10/686,536.
Official Action Dated Sep. 5, 2002 From the US Patent and Trademark Office Re.: U.S. Appl. No. 12/084,559.
Official Action Dated Aug. 10, 2007 From the US Patent and Trademark Office Re.: U.S. Appl. No. 10/836,223.
Official Action Dated Apr. 15, 2008 From the US Patent and Trademark Office Re.: U.S. Appl. No. 09/641,973.
Official Action Dated Mar. 15, 2004 From the US Patent and Trademark Office Re.: U.S. Appl. No. 09/765,316.
Official Action Dated Sep. 30, 2010 From the US Patent and Trademark Office Re.: U.S. Appl. No. 11/798,017.

Response dated Sep. 1, 2010 to Official Action of Aug. 3, 2010 From the US Patent and Trademark Office Re.: U.S. Appl. No. 11/980,690.
Response Dated Oct. 5, 2010 to Official Action of Jul. 19, 2010 From the US Patent and Trademark Office Re.: U.S. Appl. No. 11/656,548.
Aoi et al. "Absolute Quantitation of Regional Myocardial Blood Flow of Rats Using Dynamic Pinhole SPECT", IEEE Nuclear Science Symposium and Medical Imaging Conference Record, 3: 1780-1783, 2002. Abstract, Figs.
Beekman et al. "Efficient Fully 3-D Iterative SPECT Reconstruction With Monte Carlo-Based Scatter Compensation", IEEE Transactions on Medical Imaging, 21(8): 867-877, Aug. 2002.
Bromiley et al. "Attenuation Correction in PET Using Consistency Conditions and A Three-Dimensional Template", IEEE Transactions on Nuclear Science, XP002352920, 48(4): 1371-1377, 2001. p. 1376, col. 2, § 2.
Brown et al. "Method for Segmenting Chest CT Image Data Using An Anatomical Model: Preliminary Results", IEEE Transactions on Medical Imaging, 16(6): 828-839, Dec. 1997.
Corstens et al. "Nuclear Medicine's Role in Infection and Inflammation", The Lancet, 354: 765-770, 1999.
Day et al. "Localization of Radioiodinated Rat Fibrogen in Transplanted Rat Tumors", Journal of the National Cancer Institute, 23(4): 799-812, 1959.
Del Guerra et al. "An Integrated PET-SPECT Small Animal Imager: Preliminary Results", Nuclear Science Symposium, IEEE Records, 1: 541-544, 1999.
Hassan et al. "A Radiotelemetry Pill for the Measurement of Ionising Radiation Using A Mercuric Iodide Detector", Physics in Medicine and Biology, 23(2): 302-308, 1978.
Hoffman et al. "Intraoperative Probes and Imaging Probes", European Journal of Nuclear Medicine, 26(8): 913-935, 1999.
Jessup "Tumor Markers—Prognostic and Therapeutic Implications for Colorectal Carcinoma", Surgical Oncology, 7: 139-151, 1998.
Lavallée et al. "Building A Hybrid Patient's Model for Augmented Reality in Surgery: A Registration Problem", Computing in Biological Medicine, 25(2): 149-164, 1995.
Lin et al. "Improved Sensor Pills for Physiological Monitoring", NASA Tech. Brief, 25(2), 2000. JPL New Technology Report, NPO-20652.
Molinolo et al. "Enhanced Tumor Binding Using Immunohistochemical Analyses by Second Generation Anti-Tumor-Associated Glycoprotein 72 Monoclonal Antibodies versus Monoclonal Antibody B72.3 in Human Tissue", Cancer Research, 50: 1291-1298, 1990.
Piperno et al. "Breast Cancer Screening by Impedance Measurements", Frontiers Med. Biol. Engng., 2(2): 11-17, 1990.
Rajshekhar "Continuous Impedence Monitoring During CT-Guided Stereotactic Surgery: Relative Value in Cystic and Solid Lesions", British Journal of Neurosurgery, 6: 439-444, 1992.
Official Action Dated Jan. 28, 2011 From the US Patent and Trademark Office Re.: U.S. Appl. No. 09/641,973.
Response Dated Feb. 10, 2011 to Official Action of Nov. 10, 2010 From the US Patent and Trademark Office Re.: U.S. Appl. No. 10/616,307.
Response Dated Jan. 27, 2011 to Official Action of Nov. 1, 2010 From the US Patent and Trademark Office Re.: U.S. Appl. No. 11/980,690.
Response Dated Jan. 31, 2011 to Official Action of Sep. 30, 2010 From the US Patent and Trademark Office Re.: U.S. Appl. No. 11/798,017.
Notice of Allowance Dated Dec. 17, 2010 From the US Patent and Trademark Office Re. U.S. Appl. No. 11/980,617.
Official Action Dated Dec. 8, 2010 From the US Patent and Trademark Office Re.: U.S. Appl. No. 09/641,973.
Official Action Dated Dec. 28, 2010 From the US Patent and Trademark Office Re.: U.S. Appl. No. 11/607,075.
Response Dated Dec. 15, 2010 to Official Action of Jul. 19, 2010 From the US Patent and Trademark Office Re.: U.S. Appl. No. 11/656,548.
Official Action Dated Dec. 8, 2010 From the US Patent and Trademark Office Re.: U.S. Appl. No. 11/980,690.
Official Action Dated Nov. 10, 2010 From the US Patent and Trademark Office Re.: U.S. Appl. No. 10/616,307.

Official Action Dated Nov. 10, 2010 From the US Patent and Trademark Office Re.: U.S. Appl. No. 10/836,223.
Official Action Dated Nov. 23, 2010 From the US Patent and Trademark Office Re.: U.S. Appl. No. 11/656,548.
Response Dated Nov. 18, 2010 to Official Action of Jul. 19, 2010 From the US Patent and Trademark Office Re.: U.S. Appl. No. 11/607,075.
Official Action Dated Nov. 1, 2010 From the US Patent and Trademark Office Re.: U.S. Appl. No. 11/980,690.
Pluim et al. "Image Registration by Maximization of Combined Mutual Information and Gradient Information", IEEE Transactions on Medical Imaging, 19(8): 1-6, 2000.
Communication Pursuant to Article 94(3) EPC Dated Mar. 2, 2011 From the European Patent Office Re.: Application No. 06756259.5.
Notice of Non-Compliant Amendment Dated Feb. 14, 2011 From the US Patent and Trademark Office Re.: U.S. Appl. No. 10/616,307.
Mettler et al. "Legal Requirements and Radiation Safety", Essentials of Nuclear Medicine Imaging, 2nd Ed., Chap.13: 323-331, 1985.
Response Dated Mar. 8, 2011 to Official Action of Dec. 8, 2010 From the US Patent and Trademark Office Re.: U.S. Appl. No. 11/980,690.
Notice of Allowance Dated May 5, 2011 From the US Patent and Trademark Office Re.: U.S. Appl. No. 10/240,239.
Notice of Allowance Dated Feb. 23, 2011 From the US Patent and Trademark Office Re.: U.S. Appl. No. 11/980,690.
Official Action Dated Mar. 15, 2011 From the US Patent and Trademark Office Re.: U.S. Appl. No. 10/343,792.
Response Dated Mar. 24, 2011 to Official Action of Dec. 8, 2010 From the US Patent and Trademark Office Re.: U.S. Appl. No. 09/641,973.
Response Dated Mar. 3, 2011 to Notice of Non-Compliant Amendment of Feb. 14, 2011 From the US Patent and Trademark Office Re.: U.S. Appl. No. 10/616,307.
Notice of Allowance Dated May 6, 2011 From the US Patent and Trademark Office Re. U.S. Appl. No. 11/980,617.
Official Action Dated Apr. 20, 2011 From the US Patent and Trademark Office Re.: U.S. Appl. No. 11/798,017.
Official Action Dated Apr. 27, 2011 From the US Patent and Trademark Office Re.: U.S. Appl. No. 10/836,223.
Interview Summary Dated Mar. 25, 2011 From the US Patent and Trademark Office Re.: U.S. Appl. No. 10/836,223.
Mao et al. "Human Prostatic Carcinoma: An Electron Microscope Study", Cancer Research, XP002625777, 26(5): 955-973, May 1966.
Storey et al. "Tc-99m Sestamibi Uptake in Metastatic Prostate Carcinoma", Clinical Nuclear Medicine, XP009145398, 25(2): 133-134, Feb. 2000.
Official Action Dated May 23, 2011 From the US Patent and Trademark Office Re. U.S. Appl. No. 11/667,793.
Official Action Dated May 23, 2011 From the US Patent and Trademark Office Re.: U.S. Appl. No. 10/616,307.
Official Action Dated May 23, 2011 From the US Patent and Trademark Office Re.: U.S. Appl. No. 11/980,690.
Chengazi et al. "Imaging Prostate Cancer With Technetium-99m-7E11-05.3 (CYT-351)", Journal of Nuclear Medicine, 38: 675-682, 1997.
McJilton et al. "Protein Kinase Cε Interacts With Bax and Promotes Survival of Human Prostate Cancer Cells", Oncogene, 22; 7958-7968, 2003.
Xu et al. "Quantitative Expression Profile of Androgen-Regulated Genes in Prostate Cancer Cells and Identification of Prostate-Specific Genes", International Journal of Cancer, 92: 322-328, 2001.
Response Dated Apr. 5, 2011 to Official Action of Nov. 10, 2010 From the US Patent and Trademark Office Re.: U.S. Appl. No. 10/836,223.
Supplementary European Search Report and the European Search Opinion Dated Mar. 16, 2011 From the European Patent Office Re. Application No. 05803689.8.
Herrmann et al. "Mitochondrial Proteome: Altered Cytochtrome C Oxidase Subunit Levels in Prostate Cancer", Proteomics, XP002625778, 3(9): 1801-1810, Sep. 2003.
Krieg et al. "Mitochondrial Proteome: Cancer-Altered Metabolism Associated With Cytochrome C Oxidase Subunit Level Variation", Proteomics, XP002625779, 4(9): 2789-2795, Sep. 2004.
Communication Pursuant to Rules 70(2) and 70a(2) EPC Dated Apr. 4, 2011 From the European Patent Office Re. Application No. 05803689.8.
Response Dated Mar. 31, 2011 to Official Action of Jan. 31, 2011 From the US Patent and Trademark Office Re. U.S. Appl. No. 11/667,793.

* cited by examiner

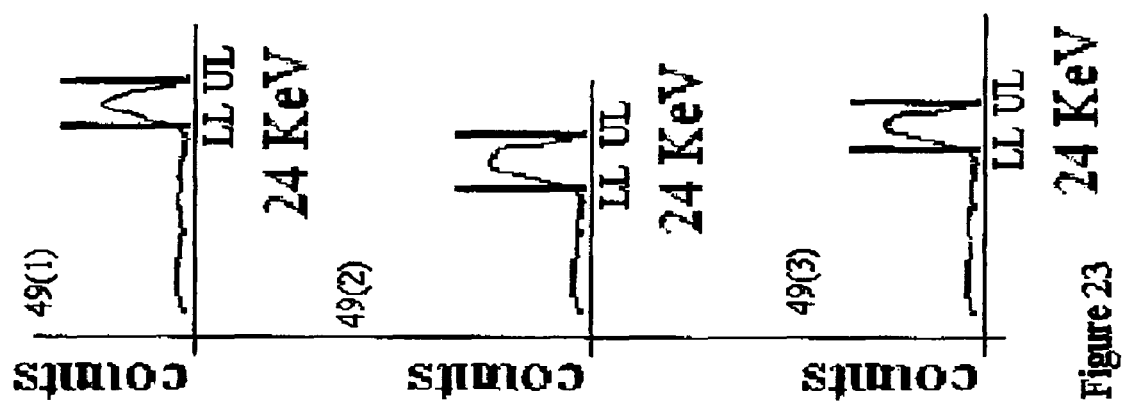

INGESTIBLE PILL FOR DIAGNOSING A GASTROINTESTINAL TRACT

This is a continuation-in-part of U.S. patent application Ser. No. 10/240,239, filed on Sep. 30, 2002, which is a National Phase application of PCT/IL02/00057, filed on Jan. 22, 2002, which is a continuation-in-part U.S. patent application Ser. No. 09/765,316 filed Jan. 22, 2001, now abandoned which derived priority form U.S. Provisional Application No. 60/285,233, filed on Apr. 23, 2001 Additionally, this application is filed concurrently with co-pending application Ser. No. 10/616,307 "RADIOACTIVE EMISSION DETECTOR EQUIPPED WITH A POSITION TRACKING SYSTEM," whose disclosure is incorporated herein by reference, and both applications derive priority from U.S. Provisional application No. 60/394,936, filed on Jul. 11, 2002.

BACKGROUND AND FIELD OF THE INVENTION

The present invention relates generally to the field of the diagnosis of ailments of said gastrointestinal tract, and particularly, to an ingestible device that travels in the gastrointestinal tract and performs diagnosis therein.

The impact of cancer of the gastrointestinal tract is grave. In spite of enormous expenditures of financial and human resources, early detection of malignant tumors remains an unfulfilled medical goal. While it is known that a number of cancers are treatable if detected at an early stage, lack of reliable screening procedures results in their being undetected and untreated.

There are other gastrointestinal-tract disorders, which similarly require reliable screening and diagnostic procedures for early detection and treatment. These include, for example, irritable bowel syndrome, fluxional diarrhea, ulcerative colitis, collagenous colitis, microscopic colitis, lymphocytic colitis, inflammatory bowel disease, Crohn's disease, infectious diarrhea, ulcerative bowel disease, lactase deficiency, infectious diarrhea, amebiasis, and giardiasis.

To some extent, simple diagnostic procedures for gastrointestinal pathologies may be employed, as part of routine checkups. For example, sampling for blood in the stool is a screening technique for digestive tract cancer. However, this procedure is not very sensitive, because blood is released when comparatively large polyps develop. Sometimes, there is no release of blood to the stool until very late in the development of the disease.

Additionally, PCT International Application WO92/00402 PCT describes a non-invasive method for detecting gastric epithelial damage using a disaccharide such as sucrose, maltose or lactose which is orally administered to a patient. Blood and urine samples are then assayed, for the disaccharide, to determine the existence and extent of gastric epithelial damage. However, this method does not reliably detect damage of the intestinal tract.

For more reliable diagnoses, various forms of endoscopes and other imaging apparatus may be used.

Diagnosis of different conditions of the colon generally involves using a colonoscope. A typical colonoscope includes, at its distal end, with respect to an operator, a light source, a video chip, and a suction channel. These elements are all in communication with a proximal end of the colonoscope via wires and channels housed within a flexible tube. The distal end is inserted into a patient's rectum and can be maneuvered along the length of the colon. A colonoscope can be inserted far enough into a patient's colon for the distal end to enter the patient's cecum. The tip of the colonoscope can also be maneuvered through the ileo-cecal valve into the terminal ileum.

A colonoscope provides a visual image only of the region of the colon that is immediately near the light source and video chip, yielding visual information for only a small region of the colon at any given time. Lesions in a patient's colon typically are identified by progressive and painstaking visual examination of the entire colon. However, a single colonoscopy is often not sufficient to identify the source of colorectal bleeding which is typically sporadic and in many cases would be best located by observing the entire colon over a period of time.

Various attachments to a colonoscope allow small surgical procedures, such as tissue biopsies, to be carried out during a colonoscopic examination.

Endoscopy of the small intestine is also known. U.S. Pat. No. 5,984,860, to Shan, entitled, "Pass-through duodenal enteroscopic device," whose disclosure is incorporated herein by reference, describes a tethered ingestible, enteroscopic video camera, which utilizes the natural contraction wave of the small intestine to propel it through the small intestine at about the same speed as any other object therein. The video camera includes an illumination source at its forward end. Covering the camera lens and illumination source is a transparent inflatable balloon, adapted to gently expand the small intestine immediately forward the camera for better viewing. A small diameter communication and power cable unwinds through an aperture in the rear of the camera as it moves through the small intestine. Upon completion of movement through the small intestine the cable is automatically separated, permitting the cable to be withdrawn through the stomach and intestine. The camera continues through the large intestine and passes from the patient through the rectum.

The aforementioned endoscopes, while providing means to access and visualize portions of the gastrointestinal track, do not provide means of detecting gastrointestinal pathologies, which are not clearly visible. In particular, they do not provide means for localization and differentiation of occult tumors. Typically, a large tumor is readily located by visualization. Yet, for subsequent operative success, as well as for the success of other forms of treatment, it is necessary to somehow locate tumors in their occult stage, when they cannot be found by sight and feel.

The use of radiolabeled immunoglobulin for tumor localization was shown to be possible in 1959 when Day et al. radiolabeled isolated antifibrin. (Day, E. O.; Planisek, J. A.; Pressman D: "Localization of Radioiodinated Rat Fibrinogen in Transplanted Rat Tumors", J. Natl. Cancer Inst. 23: 799-812, 1959). Fibrin, while not a tumor-specific antigen, was known to have a frequency of presence in tumors due to the inflammatory process-accompanying invasion. Day et al. demonstrated that a protein in high concentration in tumor sites could be used to localize tumors. The antibodies against human fibrin and ferritin were used in attempts to employ specific immunoglobulins for diagnosis.

Since the work of Day et al, in 1959, an expanding number of monoclonal antibodies have received FDA approval. Examples, applicable to gastrointestinal tract tumors, include the following:

1. CEA-Scan is a $Tc^{99m}$-labeled monoclonal antibody fragment, which targets CEA—produced and shed by colorectal carcinoma cells. The use of anti-CEA monoclonal antibody has been recommended as the only marker to estimate prognosis and response to therapy. Anti-CEA monoclonal antibody may also be labeled by other radioisotopes, for example, iodine isotopes. (Jessup J M. 1998, Tumor markers—prognostic and therapeutic implications for colorectal carcinoma, Surgical Oncology; 7: 139-151.)
2. $In^{111}$-Satumomab Pendetide (Oncoscint®) is designed to target TAG-72. TAG-72 is a mucin-like glycoprotein expressed in human colorectal, gastric, ovarian, breast and lung cancers. It is rarely expressed in normal human adult tissues. (Molinolo A; Simpson J F; et al. 1990, Enhanced tumor binding using immunohistochemical analyses by second generation anti-tumor-associated glycoprotein 72 monoclonal antibodies versus monoclonal antibody B72.3 in human tissue, Cancer Res. 50(4): 1291-8.)
3. Lipid-Associated Sialic Acid (LASA) is a tumor antigen, which for colorectal carcinoma LASA, has a similar sensitivity as CEA but a greater specificity for differentiating between benign and malignant lesions. (Ebril K M, Jones J D, Klee G G. 1985, Use and limitations of serum total and lipid-bound sialic acid concentrations as markers for colorectal cancer, Cancer; 55:404-409.)
4. Matrix Metaloproteinase-7 (MMP-7) is a proteins enzyme, believed to be involved in tumor invasion and metastasis. Its expression is elevated in tumor tissue compared to normal tissue and may be a potential marker for tumor aggressiveness and traditional staging. (Mori M, Barnard G F et al. 1995, Overexpression of matrix metalloproteinase-7 mRNA in human colon carcinoma Cancer; 75: 1516-1519.)

Additionally, pharmaceuticals may be used as markers for nonmalignant pathologies, such as gastrointestinal inflammations and infections. Examples include the following:
1. $Ga^{67}$ citrate binds to transferrin and is used for detection of chronic inflammation. (Mettler F A, and Guiberteau M J, Eds. 1998, Inflammation and infection imaging. Essentials of nuclear medicine. Fourth edition. Pgs: 387-403.)
2. Nonspecific-polyclonal immunoglobulin G (IgG) may be labeled with both $In^{111}$ or $Tc^{99m}$, and has a potential to localize nonbacterial infections. (Mettler F A, and Guiberteau M J, ibid.)
3. Radio-labeled leukocytes, such as such as $In^{111}$ oxine leukocytes and $Tc^{99m}$ HMPAO leukocytes are attracted to sites of inflammation, where they are activated by local chemotactic factors and pass through the endothelium into the soft tissue. Labeled leukocytes in the gastrointestinal tract are nonspecific and may indicate a number of pathologies, including Crohn's disease, ulcerative colitis, psudomembranous colitis, diverticulosis, various gastrointestinal infections, fistulas, ischemic or infracted bowel. (Mettler F A, and Guiberteau M J, ibid; Corstens F H; van der Meer J W. 1999. Nuclear medicine's role in infection and inflammation. Lancet; 354 (9180): 765-70.)

The particular choice of a radionuclide for labeling antibodies is dependent upon its nuclear properties, the physical half-life, the detection instruments' capabilities, the pharmacokinetics of the radiolabeled antibody, and the degree of difficulty of the labeling procedure. Examples of radionuclides used for labeling antibodies include Technetium $Tc^{99m}$, Iodine $I^{125}$, $I^{123}$, $I^{131}$, and $I^{133}$, Indium $In^{111}$, Gallium $Ga^{67}$, thallium $Tl^{201}$, fluorine $F^{18}$ and $P^{32}$.

Nuclear-radiation imaging of radionuclide-labeled antibodies is a subject of continued development and study. A particular difficulty in using radionuclides is that blood-pool background radioactivity has caused ordinary scintigrams to prove difficult to interpret. Computer subtraction of radioactive blood-pool background radioactivity has been attempted to enhance imaging. Yet the ability to detect occult tumors has remained low.

An attempt to overcome the blood-pool background radioactivity is described in U.S. Pat. No. 4,782,840 to Martin, Jr., et al., entitled, "Method for locating, differentiating, and removing neoplasms," whose disclosure is incorporated herein by reference. Martin, Jr., et al describe a method for improved localization, differentiation and removal of neoplastic tissue in animals. The improved method commences with the administering to the animal of an effective amount of a labeled antibody specific for neoplastic tissue and labeled with a radioactive isotope exhibiting specific photon emissions of energy levels. A waiting period follows, to permit the labeled antibody to preferentially concentrate in any neoplastic tissue present in the animal and to allow blood-pool background radioactivity to decrease, thus increasing the ratio of photon emissions from neoplastic tissue to background photon emissions in the animal. Thereafter, a general background photon-emission count is determined, for the tissue. Once the background count has been determined, the tissue suspected of being neoplastic is accessed by surgical means, and a handheld probe is manually maneuvered along that tissue. The probe is configured for fascicle hand positioning and maneuvering. The probe is characterized by a collimatable radiation detector having a selective photon entrance and having an output deriving discrete signals responsive to photon emissions when the entrance is positioned immediately adjacent thereto. The probe further comprises amplifier means having an input coupled with the radiation detector output and responsive to the discrete signals to provide corresponding amplified output pulses. Finally, the probe comprises readout means responsive to the output pulses and actuable to an initial condition for commencing the provision of a perceptible indication of an indicia corresponding to the number of the output pulses received. From the perceptible indication, the extent of tissue exhibiting a number of output pulses having a value above background output pulses is determined and such tissue is removed surgically.

Due to the proximity of the detection probe to the labeled antibody, the faint radiation emanating from occult sites becomes detectable. This is in part because of the inherent application of the approximate inverse square law of radiation propagation, and in part because the collimatable radiation detector may be maneuvered at various angles with respect to the suspected neoplastic tissue, so that at some positions, the collimator is aligned with the source of radiation. The procedure now is known as radioimmunoguided surgery, or RIGS™. (RIGS is a registered trademark of Neoprobe Corporation of Dublin, Ohio).

The RIGS™ system for surgery is successful because the blood-pool background of the circulating radiolabeled antibody is cleared from the body prior to imaging with the probe. As a consequence, the photon emissions or radiation emitted at minute tumors, compared to surrounding tissue, become detectable. Fortuitously, the radiolabeled antibody is capable of remaining bound to or associated with neoplastic tissue for extended periods of time with the radio tag still bound thereto. Even though the accretion of radioactivity at the tumor site decreases over time, the blood-pool background at surrounding tissue (relative to the tumor sites) decreases at a much greater rate.

RIG instrumentation generally includes two basic components, a hand-held probe, as described hereinabove, and a control console, in electrical communication with hand-held probe, via a flexible cable. The control console is located within the operating room facility but out of the sterile field, while the hand-held probe and forward portions of its associated cable are located within that field. The hand-held radiation-detecting probe is relatively small and performs in conjunction with a cadmium-zinc-telluride detector or crystal.

Further work continued to improve the sensitivity of RIGS™ to the minute number of photons that may be emitted from an occult tumor. U.S. Pat. No. 4,801,803 to Denen, et al., entitled, "Detector and localizer for low energy radiation emissions," whose disclosure is incorporated herein by reference, describes a probe particularly suited for use in immuno-guided surgery capable of detecting very faint gamma emissions and thereby localizing cancerous tumor. Detection is achieved under room temperature conditions using a crystal such as cadmium telluride. To achieve the extreme sensitivity capabilities of the apparatus, an instrumentation approach has been developed in which the somewhat fragile crystal is securely retained in isolation from externally induced incidents otherwise creating excessive noise. Microphonic effects are minimized through employment of a sequence of materials exhibiting divergent acoustic impedance. Capacitive effects caused by minute intercomponent movements are controlled to acceptable levels.

Additionally, a preamplifier is incorporated within the probe itself, which employs an integrator stage front end combining a field effect transistor and bipolar device with a very small feedback capacitance of less than one picofarad. A bootstrap technique is utilized to enhance the amplification of the bipolar amplification stage. Pulse related signals outputted from the device are normalized and compared to produce pulse data, which are analyzed. In one mode of operation a siren effect is employed to guide the surgeon towards emission sources.

The aforementioned probe is directed at low energy radionuclides, such as $I^{125}$. Additionally, the distribution of radio-labeled antibody with the nuclide is quite sparse so that background emissions can be minimized and the ratio of tumor-specific counts received to background counts can be maximized. The probe instrument and related control circuitry has been assigned the trade designation "NEOPROBE" instrument.

Further improvements to the "NEOPROBE" instrument are described in U.S. Pat. No. 5,151,598 to Denen, entitled, "Detector and localizer for low energy radiation emissions," whose disclosure is incorporated herein by reference. Further improvements include controlling capacitive and piezoelectric effects occasioned by the most minute of intercomponent movements. Additionally, compressive retention of the crystal and electrical contacts is employed in conjunction with electrically conductive but pliable surface supports.

Additionally, improvements to the "NEOPROBE" instrument are described in U.S. Pat. No. 4,893,013 to Denen et al., entitled, "Detector and Localizer for Low Energy Radiation Emissions," and U.S. Pat. No. 5,070,878 to Denen, entitled, "Detector and localizer for low energy radiation emissions," whose disclosures are incorporated herein by reference. The probe includes a cadmium telluride crystal, secured in a light-tight environment. A noise immune structuring of the probe and crystal combination includes the utilization of electrically conductive, compliant cushion layer located at one face of the crystal in conjunction with freely abutting biasing and ground contacts. A nylon, resilient retainer is positioned in tension over the assemblage of crystal, ground and biasing contacts and compliant layers to achieve a compressively retained assemblage. A dead air space is developed between the forward facing window of the probe and the crystal retaining assemblage.

To derive data representing the presence or absence of occult tumor, a microprocessor-driven complex system of analysis continuously works to statistically evaluate validated counts or gamma strikes to apprise the surgeon of the presence or absence of occult neoplastic tissue. U.S. Pat. No. 4,889,991 by Ramsey and Thurston, entitled, "Gamma Radiation Detector with Enhanced Signal Treatment," whose disclosure is incorporated herein by reference, describes an algorithm under which such an evaluation takes place. Accordingly, a hand-held gamma radiation probe, such as NEOPROBE instrument, is employed, in conjunction with a control function which provides an enhanced audio output, directed for cueing the user to the source position, as he maneuvers the probe along the tissue. The probe is positioned at a location on the animal body representing background radiation and a squelch low count rate is developed therefrom. The squelch low count rate is multiplied by a range factor to develop a squelch high-count rate and frequencies are developed from a look-up frequency table from lowest to highest in correspondence with the developed high and low squelch count rates. Slew rate limiting of the count rates is provided by development of a squelch delta value representing the difference between the squelch high and low count rates divided by a time element. Selection of frequencies for audio output from the frequency table is limited by the value of the squelch delta value. Weighting of received radiation counts is carried out continuously to develop count rate values used by the system.

U.S. Pat. No. 6,259,095, to Boutun, et al., entitled, "System and apparatus for detecting and locating sources of radiation," whose disclosure is incorporated herein by reference, describes further improvements to the aforementioned probes of Neoprobe Corporation. The apparatus incorporates a large window display utilizing icon imagery to identify counting functions such as target count and background. A variety of radionuclide modes of operation can be selected by the operator and the system automatically defaults to detector bias selection and window reference voltage selection in correspondence with the elected radionuclide. A bar graph readout apprises the user of the amount of time or count level remaining in a target or background procedure and the flashing of icon identifiers occurs during such procedures. Pulse validation is improved by the utilization of a discriminator, which evaluates pulse width.

In spite of these advances, background radiation remains an obstacle that limits the probe sensitivity to occult tumors, and there are continued endeavors to minimize its effect.

Optical fluorescence spectroscopy is a known imaging technique.

When a sample of large molecules is irradiated, for example, by laser light, it will absorb radiation, and various levels will be excited. Some of the excited states will return back substantially to the previous state, by elastic scattering, and some energy will be lost in internal conversion, collisions and other loss mechanisms. However, some excited states will create fluorescent radiation, which, due to the distribution of states will give a characteristic wavelength distribution.

Some tumor-marking agents give well-structured fluorescence spectra, when irradiated by laser light. In particular, hematoporphyrin derivatives (HPD), give a well-structured fluorescence spectrum, when excited in the Soret band around 405 nm. The fluorescence spectrum shows typical peaks at about 630 and 690 nm, superimposed in practice on more unstructured tissue autofluorescence. Other useful tumor-marking agents are dihematoporphyrin ether/ester (DHE), hematoporphyrin (HP), polyhematoporphyrin ester (PHE), and tetrasulfonated phthalocyanine (TSPC), when irradiated at 337 nm ($N_2$ laser)

U.S. Pat. No. 5,115,137, to Andersson-Engels, et al, entitled, "Diagnosis by means of fluorescent light emission from tissue," whose disclosure is incorporated herein by reference, relates to improved detection of properties of tissue by means of induced fluorescence of large molecules. The tissue character may then be evaluated from the observed large-molecule spectra According to U.S. Pat. No. 5,115,137, the spectrum for tonsil cancer is clearly different from normal mucosa, due to endogenous porphyrins.

Similarly, U.S. Pat. No. 4,785,806, to Deckelbaum, entitled, "Laser ablation process and apparatus," whose disclosure is incorporated herein by reference, describes a process and apparatus for ablating atherosclerotic or neoplastic tissues. Optical fibers direct low power light energy at a section of tissue to be ablated to cause the section to fluoresce. The fluorescence pattern is analyzed to determine whether the fluorescence frequency spectrum is representative of normal or abnormal tissue. A source of high power, ultraviolet, laser energy directed through an optical fiber at the section of tissue is fired only when the fluorometric analysis indicates that it is directed at abnormal tissue.

Additionally, U.S. Pat. No. 4,682,594, to Mok, entitled, "Probe-and fire lasers," whose disclosure is incorporated herein by reference, describes a method and apparatus of irradiating a treatment area within a body, such as blood vessel plaque. The method includes initially administering to the patient a non-toxic atheroma-enhancing reagent which causes the plaque to have a characteristic optical property when illuminated with a given radiation, introducing a catheter system including fiberoptic cable means into the artery such that the distal end thereof is operatively opposite the plaque site, introducing into the proximal end of the fiberoptic cable means the given radiation, photoelectrically sensing at the proximal end the characteristic optical property to generate a control signal, and directly under the control of the control signal transmitting via the cable means from the proximal end to the distal end, periodically occurring laser pulses until the characteristic optical property is no longer sensed.

A related fluorescence technique is described in U.S. Pat. No. 4,336,809 to Clark, entitled. "Human and animal tissue photoradiation system and method," whose disclosure is incorporated herein by reference. It relates to utilizing certain dyes, which not only selectively stain neoplastic tissue but also fluoresce in response to irradiation. Additionally, they are photodynamically cytotoxic in response to a proper wavelength of light in the presence of oxygen within living tissue. One of the dyes that is presently preferred for these characteristics contains hematoporphyrin or hematoporphyrin derivatives that when administered intravenously remain at higher concentrations for longer periods of time in traumatized or malignant tumorous tissue than in normal tissue. This dye also has a strong absorption peak centered at a wavelength of approximately 407 nanometers and responds to excitation at about this wavelength by fluorescing at a wavelength of about 614 nanometers. This makes tumor diagnosis possible by injecting the dye, allowing it to concentrate in tumorous tissue, irradiating the tissue with deep blue violet light, and observing red fluorescence. Thus, the difference in the optical property of the stained tissue and the unstained healthy tissue improves the visualization of the treatment area. This same dye has a photodynamic absorption peak at a wavelength of about 631 nanometers and is cytotoxic to malignant tissue containing the dye when irradiated with red light of about this wavelength. For diagnostic purposes krypton ion laser was used for its 406.7/413.1 nanometer lines matching the 407 nanometer absorption peak of hematoporphyrin.

U.S. Pat. No. 6,258,576, to Richards-Kortum, et al., entitled, "Diagnostic method and apparatus for cervical squamous intraepithelial lesions in vitro and in vivo using fluorescence spectroscopy," whose disclosure is incorporated herein by reference, relates to the use of multiple illumination wavelengths in fluorescence spectroscopy for the diagnosis of cervical cancer and precancer. In this manner, it has been possible to (i) differentiate normal or inflamed tissue from squamous intraepithelial lesions (SILs) and (ii) differentiate high grade SILs from non-high grade SILs. The detection may be performed in vitro or in vivo. Multivariate statistical analysis has been employed to reduce the number of fluorescence excitation-emission wavelength pairs needed to re-develop algorithms that demonstrate a minimum decrease in classification accuracy.

For example, the method of the aforementioned patent may comprise illuminating a tissue sample with electromagnetic radiation wavelengths of about 337 nm, 380 nm and 460 nm, to produce fluorescence; detecting a plurality of discrete emission wavelengths from the fluorescence; and calculating from the emission wavelengths a probability that the tissue sample belongs in particular tissue classification.

Ultrasound is another known imaging technique. Conventional ultrasonic probes are used for internal examinations in the field of obstetrics, gynecology, urology and the like.

U.S. Patent Application 20010020131, to Kawagishi, Tetsuya, et al., entitled, "Ultrasonic diagnosis system," whose disclosure is incorporated herein by reference, describes an ultrasonic diagnosis apparatus that has an ultrasonic probe, having a plurality of arrayed transducer elements, a transmitting beam former for generating driving signals for driving transducer elements, and a receiving beam former for generating receiving signals based on echo signals received by transducer elements. The transmitting beam former generates driving signals so that phases of ultrasonic waves generated from transducer elements are aligned at multiple focal points. An image processor extracts harmonic components from receiving signals of ultrasonic waves having multiple focal points, and generates ultrasonic image data based on the harmonic components.

U.S. Pat. No. 5,088,500 to Wedel., et al., entitled, "Ultrasound finger probe and method for use," whose disclosure is incorporated herein by reference, describes a method and apparatus for performing ultrasound rectal examinations, by providing an ultrasound transducer which is slipped over the physician's finger tip and then inserted into the patient's rectum, together with an apparatus for guiding medical instruments into the area to be imaged.

Similarly, U.S. Pat. No. 5,284,147, to Hanoaka, et al., entitled, "Ultrasonic probe to be installed on fingertip," whose disclosure is incorporated herein by reference, relates to an ultrasonic probe to be inserted into the body of a subject for image-processing a diagnostic target thereof by ultrasonic waves transmitted to and received from the inside of the body. More particularly, it relates to an internal examination ultrasonic probe which can be directly installed on a palpation finger. The ultrasonic probe includes a transducer array for transmitting and receiving the ultrasonic waves; a housing for supporting the transducer array, which housing is provided with a device for installing a fingertip of an operator therein; and electric wiring members connected to the transducer array and extending from the housing to the outside so that transmission and reception signals of the ultrasonic waves are supplied therethrough.

Contrast agents may be used in conjunction with ultrasound imaging, for example as taught by U.S. Pat. No. 6,280,704, to Schutt, et al., entitled, "Ultrasonic imaging system utilizing a long-persistence contrast agent," whose disclosure is incorporated herein by reference.

Temperature imaging for locating and detecting neoplastic tissue is also known. In the 1950's, it was discovered that the surface temperature of skin in the area of a malignant tumor exhibited a higher temperature than that expected of healthy tissue. Thus, by measuring body skin temperatures, it became possible to screen for the existence of abnormal body activity such as cancerous tumor growth. With the development of liquid crystals and methods of forming temperature responsive chemical substrates, contact thermometry became a reality along with its use in medical applications. Devices employing contact thermometry could sense and display temperature changes through indicators which changed colors, either permanently or temporarily, when placed in direct physical contact with a surface such as skin, reflecting a temperature at or near the point of contact. An abnormal reading would alert a user to the need for closer, more detailed examination of the region in question. However, the art in this area has been directed primarily at sensing and displaying temperatures on exterior skin surfaces. Thus, for example, the patent to Vanzetti et al. (U.S. Pat. No. 3,830,224) disclosed the placement of temperature responsive, color changing liquid crystals at various points in a brassiere for the purpose of detecting the existence of breast cancer, while the patent to Sagi (U.S. Re. No. 32,000) disclosed the use of radially arranged rows of temperature responsive indicators deposited on a disc for insertion into the breast-receiving cups of a brassiere for the same purpose.

Additionally, Tomatis, A., et al, studied reflectance images of 43 pigmented lesions of the skin (18 melanomas, 17 common melanocytic naevi and eight dysplastic naevi). Reflectance images were acquired by a telespectrophotometric system and were analyzed in the spectral range from 420 to 1040 nm, to discriminate melanoma from benign melanocytic entities. Different evaluations were carried out considering the whole spectrum, the visible and the near infrared. A total of 33 (76.7%) lesions were correctly diagnosed by the telespectrophotometric system, compared with 35 (81.4%) correct clinical diagnoses. Reflectance in the infrared band appears diagnostically relevant.

It is believed that the same principle may apply to internal body organs. An abnormally high temperature at the surface of an internal organ when compared with surrounding tissue may also indicate the likelihood of a medical problem. Thus, there are advantages to diagnostic measurements of temperature in body cavities for early indications of abnormalities. These may provide simple, speedy, accurate and cost-effective solution to screening procedures.

U.S. Pat. No. 6,135,968, to Brounstein, entitled, entitled, "Differential temperature measuring device and method," whose disclosure is incorporated herein by reference, describes a device and method for sensing temperatures at internal body locations non-surgically accessible only through body orifices. The device is particularly useful in medical applications such as screening for cancer and other abnormal biological activity signaled by an increase in temperature at a selected site. As applied to prostate examinations, the device is temporarily, adhesively affixed to a user's fingertip or to a mechanical probe. In the preferred embodiment, the device includes two temperature-sensing elements, which may include a plurality of chemical indicators. Each indicator changes color in response to detection of a predetermined particular temperature. When properly aligned and installed, the first element is located on the palmar surface of the fingertip while the second element is located on the dorsal surface of the fingertip. After an examination glove has been donned over the fingertip carrying the device, a prostate examination is performed during which the first element is brought into constant but brief contact with the prostate region and the second element is similarly, simultaneously brought into contact with a dermal surface opposing the prostate region. Upon withdrawal of the fingertip from the rectum and removal of the glove, the two temperature sensing elements may be visually examined in order to determine the temperatures detected by each one. A significant difference in observed temperatures indicates the possibility of abnormal biological activity and the need for further diagnostic or medical procedures.

Infrared thermography is a temperature imaging technique, which measures thermal energy emitted from the body surface without contact, quickly and dynamically, and produces a temperature image for analysis. Harzbecker K, et al. report, based on thermic observations in 63 patients and a control experiment in 15 persons, on experiences with thermography in the diagnosis of diseases, which are localized more profoundly in the thoracic cavity. (Harzbeeker K, et al., "Thermographic thorax diagnostics," Z Gesamte Inn Med. Feb. 1, 1978; 33(3):78-80.)

Similarly, Dexter L I, Kondrat'ev V B. report data concerning the use of lymphography and thermography for the purpose of establishing a differential diagnosis in 42 patients with edema of the lower limbs of a different origin. A comparative estimation of different methods of the differential diagnosis indicated the advantages of infrared thermography. (Dexter L I, Kondrat'ev V B., "Thermography in differential diagnosis of lymphostasis in the lower limbs," Vestn Khir Im I I Grek. 1976 June; 116(6):60-4.)

Electrical Impedance imaging is another known imaging technique for detecting tumors. Relying on inexpensive probes, it provides a simple screening procedure, particularly for breast cancer. ("Breast Cancer screening by impedance measurements" by G. Piperno et al. Frontiers Med. Biol. Eng., Vol. 2, pp 111-117). It involves systems in which the impedance between a point on the surface of the skin and some reference point on the body of a patient is determined. Sometimes, a multi-element probe, formed as a sheet with an array of electrical contacts is used, for obtaining a two-dimensional impedance map of the tissue, for example, the breast. The two-dimensional impedance map may be used, possibly in conjunction with other data, such as mammography, for the detection of cancer.

Rajshekhar, V., describes using an impedance probe having a single electrode to measure the impedance characteristics of lesions ("Continuous impedance monitoring during CT-guided stereotactic surgery: relative value in cystic and solid lesions," Rajshekhar, V., British Journal of Neurosurgery, 1992, 6, 439-444). The objective of the study was to use the measurements made in the lesions to determine the extent of the lesions and to localize the lesions more accurately. The probe is guided to the tumor by CT and four measurements were made within the lesion as the probe passed through the lesion. A biopsy of the lesion was performed using the outer sheath of the probe as a guide to position, after the probe itself was withdrawn.

U.S. Pat. No. 4,458,694, to Sollish, et al., entitled, "Apparatus and method for detection of tumors in tissue," whose disclosure is incorporated herein by reference, relates to apparatus for detecting tumors in human breast, based on the dielectric constants of localized regions of the breast tissue. The apparatus includes a probe, comprising a plurality of elements. The apparatus further includes means for applying an AC signal to the tissue, means for sensing electrical properties at each of the probe elements at different times, and signal processing circuitry, coupled to the sensing means, for comparing the electrical properties sensed at the different times. The apparatus thus provides an output of the dielectric constants of localized regions of breast tissue associated with the probe.

Similarly, U.S. Pat. No. 4,291,708 to Frei, et al., entitled, "Apparatus and method for detection of tumors in tissue," whose disclosure is incorporated herein by reference, relates to apparatus for detecting tumors in human breast tissue. The apparatus includes means for determining the dielectric constants of a plurality of localized regions of human breast tissue. These include a bridge, which is provided with a circuit for automatically nulling the bridge while in operation. Means are further provided for measuring variations in the dielectric constants over a plurality of the regions and for indicating the possible presence of a tumor as result of the measurement. The apparatus may be utilized in carrying out a method of detecting tumors which includes the steps of applying a plurality of probe elements to breast tissue for sensing characteristics of localized regions thereof, applying an electrical signal to the probe elements for determining dielectric constants of localized regions of the tissue, sensing variations in the dielectric constants and determining the rate-of-change of dielectric constant at each of the localized regions.

U.S. Pat. Nos. 6,308,097, 6,055,452 and 5,810,742, to Pearlman, A. L., entitled, "Tissue characterization based on impedance images and on impedance measurements," whose disclosures are incorporated herein by reference, describe apparatus for aiding in the identification of tissue type for an anomalous tissue in an impedance image comprising: means for providing an polychromic immitance map of a portion of the body; means for determining a plurality of polychromic measures from one or both of a portion of the body; and a display which displays an indication based on said plurality of polychromic measures.

Magnetic resonance imaging (MRI) is based on the absorption and emission of energy in the radio frequency range of the electromagnetic spectrum, by nuclei having unpaired spins.

The hardware components associated with an MRI imager are:
i. a primary magnet, which produces the $B_o$ field for the imaging procedure;
ii. gradient coils for producing a gradient in $B_o$;
iii. an RF coil, for producing the $B_1$ magnetic field, necessary to rotate the spins by 90° or 180° and for detecting the NRI signal; and
iv. a computer, for controlling the components of the MRI imager.

Generally, the magnet is a large horizontal bore superconducting magnet, which provides a homogeneous magnetic field in an internal region within the magnet. A patient or object to be imaged is usually positioned in the homogeneous field region located in the central air gap for imaging.

A typical gradient coil system comprises an antihelmholtz type of coil. These are two parallel ring shaped coils, around the z axis. Current in each of the two coils flows in opposite directions creating a magnetic field gradient between the two coils.

The RF coil creates a $B_1$ field, which rotates the net magnetization in a pulse sequence. They may be: 1) transmit and receive coils, 2) receive only coils, and 3) transmit only coils.

In this geometry, use of catheters equipped with miniature RF coils for internal imaging of body cavities, still requires positioning the patient in a conventional large MRI magnet. This environment can result in deficient images because the various orientations of the RF coil, e.g., in an artery, will not be positioned always colinearly with the RF excitation field.

This problem has been resolved by U.S. Pat. No. 5,572,132, to Pulyer, et al., entitled, "MRI probe for external imaging," whose disclosure is incorporated herein by reference, wherein an MRI catheter for endoscopical imaging of tissue of the artery wall, rectum, urinal tract, intestine, esophagus, nasal passages, vagina and other biomedical applications is described.

The invention teaches an MRI spectroscopic probe having an external background magnetic field $B_0$ (as opposed to the internal background magnetic filed of the large horizontal bore superconducting magnet.) The probe comprises (i) a miniature primary magnet having a longitudinal axis and an external surface extending in the axial direction and (ii) a RF coil surrounding and proximal to said surface. The primary magnet is structured and configured to provide a symmetrical, preferably cylindrically shaped, homogeneous field region external to the surface of the magnet. The RF coil receives NMR signals from excited nuclei. For imaging, one or more gradient coils are provided to spatially encode the nuclear spins of nuclei excited by an RF coil, which may be the same coil used for receiving NMR signals or another RF coil.

U.S. Pat. No. 6,315,981 to Unger, entitled, "Gas filled microspheres as magnetic resonance imaging contrast agents," whose disclosure is incorporated herein by reference, describes the use of gas filled microspheres as contrast agents for magnetic resonance imaging (MRI). Unger further describes how gas can be used in combination with polymer compositions and possibly also with paramagnetic, superparamagnetic, and liquid fluorocarbon compounds as MRI contrast agents. It is further shown how the gas stabilized by polymers would function as an effective susceptibility contrast agent to decrease signal intensity on T2 weighted images; and that such systems are particularly effective for use as gastrointestinal MRI contrast media.

Ingestible radio pills, which are ingestible capsules containing a transmitter are known. In 1964 research at Heidelberg University developed a pill for monitoring pH of the gastrointestinal tract. (Noller, H. G., "The Heidelberg Capsule Used For the Diagnosis of Pepic Diseases", Aerospace Medicine, February 1964, pp. 15-117.)

U.S. Pat. No. 4,844,076, to Lesho, et al., of July 1989, entitled, "Ingestible size continuously transmitting temperature monitoring pill," whose disclosure is incorporated herein by reference, describes a temperature responsive transmitter, encapsulation in an ingestible size capsule. The capsule is configured to monitor average body temperature, internally. The ingestible size temperature pill can be configured in a rechargeable embodiment. In this embodiment the pill uses the inductive coil in the tank circuit as the magnetic pickup to charge a rechargeable nickel cadmium battery.

U.S. Pat. No. 5,279,607, to Schentag, et al., "Telemetry capsule and process," whose disclosure is incorporated herein by reference, describes an ingestible capsule and a process for delivery, particularly repeatable delivery, of a medicament to the alimentary canal. The ingestible capsule is essentially non-digestible capsule, which contains an electric energy emitting means, a radio signal transmitting means, a medicament storage means and a remote actuatable medicament releasing means. The capsule signals a remote receiver as it progresses through the alimentary tract in a previously mapped route and upon reaching a specified site is remotely triggered to release a dosage of medicament.

Similarly, U.S. Pat. No. 5,395,366, to D'Andrea et al., entitled, "Sampling capsule and process," whose disclosure is incorporated herein by reference, describes a similar ingestible capsule and a process for sampling of fluids in the to the alimentary canal.

U.S. Pat. No. 5,604,531, to Iddan, et al., entitled, "In vivo video camera system," whose disclosure is incorporated herein by reference, describes a video camera system, encapsulated within an ingestible pill, arranged to pass through the entire digestive tract, operating as an autonomous video endoscope. The ingestible pill includes a camera system and an optical system for imaging an area of interest onto the camera system, and a transmitter, which relays the video output of the camera system to an extracorporeal reception system. A light source is located within a borehole of the optical system.

Similarly, U.S. Patent Application 20010035902, to Iddan, G. J., et al., entitled, "Device and system for in vivo imaging," Whose disclosure is incorporated herein by reference, describes a system and method for obtaining in vivo images. The system contains an imaging system and an ultra low power radio frequency transmitter for transmitting signals from the CMOS imaging camera to a receiving system located outside a patient. The imaging system includes at least one CMOS imaging camera, at least one illumination source for illuminating an in vivo site and an optical system for imaging the in vivo site onto the CMOS imaging camera.

U.S. Pat. No. 6,324,418, to Crowley, et al., entitled, "Portable tissue spectroscopy apparatus and method," whose disclosure is incorporated herein by reference, describes a portable tissue spectroscopy apparatus including at least one light source, at least one light detector, a power source and a controller module, all disposed inside a housing that is insertable inside a body. The housing may be in the form of a hand-holdable probe or in the form of a capsule that can be swallowed or implanted in the body. The probe further includes a display mounted at a proximal end of the housing for displaying tissue characteristics. The capsule further includes a transmitter mounted inside the capsule and a receiver placed outside the body for transmitting signals representative of tissue characteristics to a remote receiver.

The capsule includes one or more light emitters and one or more light detectors. The light detectors may be located in various places within the housing for detecting spectroscopic properties from various tissues near the capsule. The capsule may further include other types of emitters and sensors. The additional emitters and sensors, for example, can relate to electromagnetic radiation, pressure, temperature, x-ray radiation and/or heat. In one embodiment, the capsule further comprises an acoustic transmitter and a receiver for measuring flow of fluid or for detecting echo location of the capsule. In another embodiment, the capsule further includes diagnostic sensors such as monitoring electrodes, pressure sensors and temperature sensors.

U.S. Pat. No. 5,415,1818, to Hogrefe, et al., entitled, "AM/FM multi-channel implantable/ingestible biomedical monitoring telemetry system," whose disclosure is incorporated herein by reference, describes a wireless multi-channel circuit for telemetering signals representing physiological values from a point in a human body to a receiver outside of the body. The two signals, S1 and S2, other than the temperature signal are used to provide two frequency modulated signals summed by an amplifier with the summed FM signal then being applied to amplitude modulate a carrier whose frequency varies as a function of temperature. The resulting FM/AM signal is telemetered inductively outside of the body to an external receiver. Appropriate demodulation, filter, and shaping circuits within the external circuit detect the FM signals and thus produce three independent frequencies two of which are the original physiological variables and the third a function of local temperature. Real time plot of the two physiological variables can be obtained using FM discriminators while the temperature dependent frequency is best monitored by a counter.

Similarly, U.S. Pat. No. 5,842,977 to Lesho, et al., entitled, "Multi-channel pill with integrated optical interface," whose disclosure is incorporated herein by reference, describes an optical interface incorporated into a multi-channel telemetry device, used to provide data representing physiological conditions.

Methods of tracking ingestible devices, such as radio pills, are known. U.S. Pat. No. 5,279,607, to Schentag, et al., entitled, "Telemetry capsule and process," and U.S. Pat. No. 5,395,366, to D'Andrea et al., entitled, "Sampling capsule and process," described hereinabove, include extracorporeal apparatus having a plurality of antennae, used to determine the geographic position of the capsule within the gastrointestinal tract. For example, at least three antennae, located at different distances from the point source, and dedicated algorithms may be used to determine the precise location of the capsule, at any time.

U.S. Pat. No. 6,082,366 to Andrii et al., entitled, "Method and arrangement for determining the position of a marker in an organic cavity," whose disclosure is incorporated herein by reference, describe a method for pinpointing a marker such as an ingestible capsule. The method requires that the patient be positioned within a magnetic field, for example, as used for MRI imaging.

Notwithstanding the high level of sophistication of the aforementioned systems, gastrointestinal pathologies, and particularly, occult tumors have remained elusive in medical diagnosis. There is thus a widely recognized need for, and it would be highly advantageous to have, a device and method for detecting pathologies in the gastrointestinal tract devoid of the above limitations.

SUMMARY OF THE INVENTION

According to an aspect of the present invention there is provided an ingestible device, arranged for traveling within a gastrointestinal tract of a body, comprising:
- a probe, operative to perform, along said gastrointestinal tract, a diagnostic image by nuclear radiation of a radiopharmaceutical,
- data-handling apparatus, in signal communication with said probe, for receiving and handling imaging data, generated by said probe;
- a power source, for powering said probe and data-handling apparatus; and
- a shell, which encapsulates said probe, data-handling apparatus, and power source within.

According to an additional aspect of the present invention, said probe comprises a nuclear-radiation detector, arranged for detecting gamma and beta radiation.

According to still an additional aspect of the present invention, said nuclear-radiation detector is not collimated, to detect nuclear radiation impinging at any angle.

According to yet an additional aspect of the present invention, said nuclear-radiation detector is gated to a narrow energy range, associated with a particular radioisotope.

According to still an additional aspect of the present invention, said nuclear-radiation detector comprises at least two crystals.

According to yet an additional aspect of the present invention, each of said at least two crystals is gated to a different narrow energy range, associated with a different radioisotope.

According to still an additional aspect of the present invention, said at least two crystals are a predetermined distance apart, in the direction of travel, and are operative to evaluate an incremental distance traveled within said gastrointestinal tract, during a period $\Delta T$, by cross correlating nuclear radiation striking said at least two crystals at a time T and at a later time T+$\Delta T$.

According another aspect of the present invention, said probe comprises a photodetector, arranged to detect scintillation produced by a scintillation liquid responsive to nuclear radiation of said radiopharmaceutical.

According to an additional aspect of the present invention, said photodetector comprises at least two photo-sensing diodes, arranged a predetermined distance apart, in the direction of travel, operative to evaluate an incremental distance traveled within said gastrointestinal tract, during a period $\Delta T$, by cross correlating scintillation striking said photo-sensing diodes at a time T and at a later time T+$\Delta T$.

According to an aspect of the present invention there is provided an ingestible device, arranged for traveling within a gastrointestinal tract of a body, comprising:
- a probe, comprising a photodetector, operative to perform, along said gastrointestinal tract, a diagnostic image by optical fluorescence of a fluorescing-pharmaceutical;
- a laser light source, of a wavelength which substantially matches at least one absorption peak of said fluorescing-pharmaceutical;
- data-handling apparatus, in signal communication with said probe, for receiving and handling imaging data, generated by said probe;
- a power source, for powering said probe, light source, and data-handling apparatus; and
- a shell, which encapsulates said probe, light source, data-handling apparatus, and power source within.

According to an additional aspect of the present invention, said photodetector comprises at least two photo-sensing diodes, arranged a predetermined distance apart, in the direction of travel, operative to evaluate an incremental distance traveled within said gastrointestinal tract, during a period $\Delta T$, by cross correlating fluorescence striking said photo-sensing diodes at a time T and at a later time T+$\Delta T$.

According to still an additional aspect of the present invention, said ingestible device further includes at least two reflected-light photo-sensing diodes, arranged a predetermined distance apart, in the direction of travel, operative to evaluate an incremental distance traveled within said gastrointestinal tract, during a period $\Delta T$, by cross correlating reflected light striking said reflected-light photo-sensing diodes at a time T and at a later time T+$\Delta T$.

According to an aspect of the present invention there is provided an ingestible device, arranged for traveling within a gastrointestinal tract of a body, comprising:
- a probe, comprising a photodetector, operative to perform, along said gastrointestinal tract, a diagnostic image by optical fluorescence of a bare gastrointestinal-tract tissue;
- a laser light source, of a wavelength which substantially matches an absorption peak of said bare gastrointestinal-tract tissue;
- data-handling apparatus, in signal communication with said probe, for receiving and handling imaging data, generated by said probe;
- a power source, for powering said probe, light source, and data-handling apparatus; and
- a shell, which encapsulates said probe, light source, data-handling apparatus, and power source within,
- wherein said photodetector comprises at least two photo-sensing diodes, arranged a predetermined distance apart, in the direction of travel, operative to evaluate an incremental distance traveled within said gastrointestinal tract, during a period $\Delta T$, by cross correlating fluorescence striking said photo-sensing diodes at a time T and at a later time T+$\Delta T$.

According to an additional aspect of the present invention, said ingestible device further includes at least two reflected-light photo-sensing diodes, adapted to sense reflected light from said laser light source, arranged a predetermined distance apart, in the direction of travel, operative to evaluate an incremental distance traveled within said gastrointestinal tract, during a period $\Delta T$, by cross correlating reflected light striking said reflected-light photo-sensing diodes at a time T and at a later time T+$\Delta T$.

According to an aspect of the present invention there is provided an ingestible device, arranged for traveling within a gastrointestinal tract of a body, comprising:
- a probe, comprising a thermography detector, operative to perform, along said gastrointestinal tract, a diagnostic image by infrared thermography;
- data-handling apparatus, in signal communication with said probe, for receiving and handling imaging data, generated by said probe;
- a power source, for powering said probe and data-handling apparatus; and
- a shell, which encapsulates said probe, data-handling apparatus, and power source within.

According to an additional aspect of the present invention, said thermography detector comprises at least two photo-sensing diodes, arranged a predetermined distance apart, in the direction of travel, operative to evaluate an incremental distance traveled within said gastrointestinal tract, during a period $\Delta T$, by cross correlating infrared radiation striking said photo-sensing diodes at a time T and at a later time T+$\Delta T$.

According to an aspect of the present invention there is provided an ingestible device, arranged for traveling within a gastrointestinal tract of a body, comprising:
- a thermocouple probe, operative to perform, along said gastrointestinal tract, a diagnostic image by temperature-differences;
- data-handling apparatus, in signal communication with said probe, for receiving and handling imaging data, generated by said probe;
- a power source, for powering said probe and data-handling apparatus; and
- a shell, which encapsulates said probe, data-handling apparatus, and power source within.

According to an aspect of the present invention there is provided an ingestible device, arranged for traveling within a gastrointestinal tract of a body, comprising:
- an impedance probe, operative to perform, along said gastrointestinal tract, a diagnostic image by impedance;
- data-handling apparatus, in signal communication with said probe, for receiving and handling imaging data, generated by said probe;
- a power source, for powering said probe and data-handling apparatus; and
- a shell, which encapsulates said probe, data-handling apparatus, and power source within.

According to an aspect of the present invention there is provided an ingestible device, arranged for traveling within a gastrointestinal tract of a body, comprising:
- an ultrasound probe, operative to perform, along said gastrointestinal tract, a diagnostic image by ultrasound reflection;
- data-handling apparatus, in signal communication with said probe, for receiving and handling imaging data, generated by said probe;

a power source, for powering said probe and data-handling apparatus; and a shell, which encapsulates said probe, data-handling apparatus, and power source within.

According to an aspect of the present invention there is provided an ingestible device, arranged for traveling within a gastrointestinal tract of a body, comprising:

an MRI probe, operative to perform, along said gastrointestinal tract, a diagnostic image by magnetic resonance;

data-handling apparatus, in signal communication with said probe, for receiving and handling imaging data, generated by said probe;

a power source, for powering said probe and data-handling apparatus; and a shell, which encapsulates said probe, data-handling apparatus, and power source within.

According to an aspect of the present invention there is provided an ingestible device, arranged for traveling within a gastrointestinal tract of a body, comprising:

at least two probes, each operative to perform, along said gastrointestinal tract, a diagnostic image selected from the group, which consists of nuclear radiation of a radiopharmaceutical, scintillation of a scintillation liquid, responsive to nuclear radiation of a radiopharmaceutical, optical fluorescence of a fluorescing-pharmaceutical, optical fluorescence of a bare gastrointestinal-tract tissue, infrared thermography, temperature-differences, impedance, ultrasound reflection, magnetic resonance, and video, wherein each probe is operative to perform a different diagnostic image;

data-handling apparatus, in signal communication with said probes, for receiving and handling imaging data, generated by said probes;

a power source, for powering said probes and said data-handling apparatus; and a shell, which encapsulates said probes, data-handling apparatus, and power source within.

According to an additional aspect of the present invention, said ingestible device further includes a coating, selected from the group consisting of a candy-like coating, a biologically inert coating which is replaced between uses, and a biologically inert coating which is replaced between uses, covered with a candy-like coating.

According to still an additional aspect of the present invention, said data-handling apparatus comprises a transmitter, communicable with said probe and in signal communication with extracorporeal apparatus.

According to yet an additional aspect of the present invention, said transmitter comprises a piezoelectric transducer.

According to still an additional aspect of the present invention, said piezoelectric transducer is further arranged for tracking said ingestible device within said gastrointestinal tract, in tandem with at least three extracorporeal piezoelectric transducers, at different locations, in direct contact with said body, based on the time of signal travel from each of said extracorporeal transducer to said ingestible device and back.

According to yet an additional aspect of the present invention, said transmitter comprises an RF transmitter.

According to still an additional aspect of the present invention, said transmitter is further arranged for tracking said ingestible device within said gastrointestinal tract, in tandem with at least three extracorporeal RF receivers.

According to yet an additional aspect of the present invention, said transmitter comprises a multi-channel transmitter.

According to still an additional aspect of the present invention, said transmitter produces a reference signal at predetermined time intervals.

According to yet an additional aspect of the present invention, said reference signal further includes identifying information of said body.

According to still an additional aspect of the present invention, said ingestible device further includes a receiver.

According to yet an additional aspect of the present invention, said receiver comprises a multi-channel receiver.

According to still an additional aspect of the present invention, said data-handling apparatus comprises a computing means.

According to yet an additional aspect of the present invention, said ingestible device further includes a memory, for recording diagnostic information produced by said probe, therein.

According to still an additional aspect of the present invention, said memory is a removable data-storage implement.

According to yet an additional aspect of the present invention, said power source comprises an energizable power source.

According to still an additional aspect of the present invention, said energizable power source comprises a piezoelectric transducer.

According to yet an additional aspect of the present invention, said ingestible device further includes a tracking means, for tracking said ingestible device within said gastrointestinal tract.

According to still an additional aspect of the present invention, said tracking is performed vis a vis an extracorporeal reference system.

According to yet an additional aspect of the present invention, said tracking means comprises at least one acceleration sensor, which senses accelerations in at least three degrees of freedom, with respect to a set of three mutually perpendicular coordinate axes.

According to another aspect of the present invention, said tracking means comprises at least at least three acceleration sensors, each sensing accelerations along a single axis of a set of three mutually perpendicular coordinate axes.

According to still another aspect of the present invention, said tracking means comprises a magnetic tracking and location system.

According to yet another aspect of the present invention, said tracking means includes a piezoelectric transducer, operable in tandem with at least three extracorporeal piezoelectric transducers, at different locations, in direct contact with said body, for tracking based on the time of signal travel from each of said extracorporeal transducer to said ingestible device and back.

According to another aspect of the present invention, said tracking is performed vis a vis the walls of said gastrointestinal tract.

According to an additional aspect of the present invention, said tracking means comprises at least one roller, adapted to roll against the tissue of said gastrointestinal tract, wherein said at least one roller is in communication with a counter, and wherein the number of revolutions made by said at least one roller indicate the length traveled by said ingestible device.

According to still an additional aspect of the present invention, said tracking means includes at least two piezoelectric transducers, arranged a predetermined distance apart, in the direction of travel, operative to evaluate an incremental distance traveled within said gastrointestinal tract, during a period $\Delta T$, by cross correlating ultrasound reflection of an ultrasound pulse, originating from one of said at least two piezoelectric transducers, striking said at least two piezoelectric transducers, at a time T and at a later time $T+\Delta T$.

According to yet an additional aspect of the present invention, said ingestible device further includes a plurality of piezoelectric transducers, to enhance the cross correlation.

According to still an additional aspect of the present invention, said tracking means includes a light source and at least two photo-sensing diodes, arranged a predetermined distance apart, in the direction of travel, operative to evaluate an incremental distance traveled within said gastrointestinal tract, during a period $\Delta T$, by cross correlating reflected light striking said photo-sensing diodes at a time T and at a later time $T+\Delta T$.

According to yet an additional aspect of the present invention, said ingestible device further includes a plurality of photo-sensing diodes to enhance the cross correlation.

According to still an additional aspect of the present invention, said ingestible device is disposable, and needs not be retrieved.

According to an aspect of the present invention there is provided a tissue diagnostic system, comprising:
an ingestible device; and
extracorporeal apparatus, comprising:
at least one extracorporeal receiver;
an extracorporeal computing means; and
an extracorporeal power source.

According to an additional aspect of the present invention, said extracorporeal apparatus further includes a replaceable interface.

According to still an additional aspect of the present invention, said at least one extracorporeal receiver further includes at least three extracorporeal receivers, for tracking said ingestible device.

According to yet an additional aspect of the present invention, said at least three extracorporeal receivers further includes at least three piezoelectric-transducer patch-sensor devices.

According to another aspect of the present invention, said at least one extracorporeal receiver comprises an RF receiver.

According to an additional aspect of the present invention, said at least one extracorporeal receiver comprises a multi-channel receiver.

According to still an additional aspect of the present invention, said system further comprises an RF transmitter.

According to yet an additional aspect of the present invention, said ingestible device further comprises at least one intracorporeal acceleration sensor, which senses accelerations in at least three degrees of freedom, with respect to a set of three mutually perpendicular coordinate axes, and said extracorporeal apparatus further comprises at least one extracorporeal acceleration sensor, for sensing accelerations of said body, in at least three degrees of freedom, with respect to a set of three mutually perpendicular coordinate axes, in order to correct measurements of said intracorporeal acceleration sensor, for movements of said body.

According to an aspect of the present invention there is provided a method of performing tissue diagnosis within a gastrointestinal tract of a body, comprising:
providing an ingestible device comprising a probe, operative to perform, along said gastrointestinal tract, a diagnostic image by nuclear radiation of a radiopharmaceutical;
administrating said radiopharmaceutical;
ingesting said ingestible device, a predetermined time after said administrating said radiopharmaceutical;
producing diagnostic signals with said probe, as said ingestible device travels in said gastrointestinal tract, thus forming said diagnostic image; and
recording information of said diagnostic image.

According to an additional aspect of the present invention, said probe comprises a nuclear-radiation detector, arranged for detecting gamma and beta radiation.

According to still an additional aspect of the present invention, said nuclear-radiation detector comprises at least two crystals.

According to yet an additional aspect of the present invention, said method further includes gating each of said crystals to a different narrow energy range, associated with a different radioisotope.

According to still an additional aspect of the present invention, said method further includes using the clock-like property of nuclear radiation to identify a pathological site, by an activity ratio of at least two radioisotopes.

According to yet an additional aspect of the present invention, said at least two crystals are arranged a predetermined distance apart, in the direction of travel, and wherein said method further includes evaluating the distance traveled within said gastrointestinal tract, by cross correlating nuclear radiation striking said crystals at a time T and at a later time $T+\Delta T$.

According another aspect of the present invention, said probe comprises a photodetector, wherein said method further includes administrating a scintillation liquid, a predetermined time after said administrating said radiopharmaceutical and a predetermined time before said ingesting said ingestible device, and wherein said producing diagnostic signals with said probe further includes detecting scintillation, produced by said scintillation liquid, responsive to nuclear radiation of said radiopharmaceutical, thus forming said diagnostic image.

According to an additional aspect of the present invention, said probe comprises at least two photo-sensing diodes, arranged a predetermined distance apart, in the direction of travel, and said method further includes evaluating the distance traveled within said gastrointestinal tract, by cross correlating scintillation striking said photo-sensing diodes at a time T and at a later time $T+\Delta T$.

According to an aspect of the present invention there is provided a method of performing tissue diagnosis within a gastrointestinal tract, comprising:
providing an ingestible device comprising a laser light source and a probe, comprising a photodetector, operative to perform, along said gastrointestinal tract, a diagnostic image by optical fluorescence of a fluorescing-pharmaceutical, wherein said laser light source is operative at a wavelength that substantially matches an absorption peak of said fluorescing-pharmaceutical;
administrating said fluorescing-pharmaceutical;
ingesting said ingestible device, a predetermined time after said administrating said fluorescing-pharmaceutical;
producing diagnostic signals with said probe, as said ingestible device travels in said gastrointestinal tract, thus forming said diagnostic image; and
recording information of said diagnostic image.

According to an additional aspect of the present invention, said photodetector comprises at least two photo-sensing diodes, arranged a predetermined distance apart, in the direction of travel, and said method further includes evaluating the distance traveled within said gastrointestinal tract, by cross correlating fluorescence striking said photo-sensing diodes at a time T and at a later time $T+\Delta T$.

According to still an additional aspect of the present invention, said ingestible device further includes at least two reflected-light photo-sensing diodes, arranged a predetermined distance apart, in the direction of travel, and said method further includes evaluating the distance traveled within said gastrointestinal tract, by cross correlating reflected light striking said reflected-light photo-sensing diodes at a time T and at a later time T+ΔT.

According to an aspect of the present invention there is provided a method of performing tissue diagnosis within a gastrointestinal tract, comprising:
 providing an ingestible device comprising a laser light source and a probe, comprising a photodetector, operative to perform, along said gastrointestinal tract, a diagnostic image by optical fluorescence of a bare tissue, wherein said laser light source is operative at a wavelength that substantially matches an absorption peak of said bare gastrointestinal-tract tissue;
 ingesting said ingestible device;
 producing diagnostic signals with said probe, as said ingestible device travels in said gastrointestinal tract, thus forming said diagnostic image; and
 recording information of said diagnostic image,
 wherein said photodetector comprises at least two photo-sensing diodes, arranged a predetermined distance apart, in the direction of travel, and wherein said method further includes evaluating the distance traveled within said gastrointestinal tract, by cross correlating fluorescence striking said photo-sensing diodes at a time T and at a later time T+ΔT.

According to an additional aspect of the present invention, said ingestible device further includes at least two reflected-light photo-sensing diodes, arranged a predetermined distance apart, in the direction of travel, and wherein said method further includes evaluating the distance traveled within said gastrointestinal tract, by cross correlating reflected light striking said reflected-light photo-sensing diodes at a time T and at a later time T+ΔT.

According to an aspect of the present invention there is provided a method of performing tissue diagnosis within a gastrointestinal tract, comprising:
 providing an ingestible device comprising a probe, which further comprises a thermography detector, operative to perform, along said gastrointestinal tract, a diagnostic image by infrared thermography;
 ingesting said ingestible device;
 producing diagnostic signals with said probe, as said ingestible device travels in said gastrointestinal tract, thus forming said diagnostic image; and
 recording information of said diagnostic image.

According to an additional aspect of the present invention, said thermography detector further comprises at least two photo-sensing diodes, arranged a predetermined distance apart, in the direction of travel, and wherein said method further includes evaluating the distance traveled within said gastrointestinal tract, by cross correlating infrared radiation striking said photo-sensing diodes at a time T and at a later time T+ΔT.

According to an aspect of the present invention there is provided a method of performing tissue diagnosis within a gastrointestinal tract, comprising:
 providing an ingestible device comprising a thermocouple probe, operative to perform, along said gastrointestinal tract, a diagnostic image by temperature-differences;
 ingesting said ingestible device;
 producing diagnostic signals with said probe, as said ingestible device travels in said gastrointestinal tract, thus forming said diagnostic image; and
 recording information of said diagnostic image.

According to an aspect of the present invention there is provided a method of performing tissue diagnosis within a gastrointestinal tract, comprising:
 providing an ingestible device comprising an impedance probe, operative to perform, along said gastrointestinal tract, a diagnostic image by impedance;
 ingesting said ingestible device;
 producing diagnostic signals with said probe, as said ingestible device travels in said gastrointestinal tract, thus forming said diagnostic image; and
 recording information of said diagnostic image.

According to an aspect of the present invention there is provided a method of performing tissue diagnosis within a gastrointestinal tract, comprising:
 providing an ingestible device comprising an ultrasound probe, operative to perform, along said gastrointestinal tract, a diagnostic image by ultrasound reflection;
 ingesting said ingestible device;
 producing diagnostic signals with said probe, as said ingestible device travels in said gastrointestinal tract, thus forming said diagnostic image; and
 recording information of said diagnostic image.

According to an aspect of the present invention there is provided a method of performing tissue diagnosis within a gastrointestinal tract, comprising:
 providing an ingestible device comprising an MRI probe, operative to perform, along said gastrointestinal tract, a diagnostic image by magnetic resonance;
 ingesting said ingestible device;
 producing diagnostic signals with said probe, as said ingestible device travels in said gastrointestinal tract, thus forming said diagnostic image; and
 recording information of said diagnostic image.

According to an additional aspect of the present invention, said method further includes resonating at a frequency of a contrast agent that has been administered to said body.

According to an aspect of the present invention there is provided a method of performing tissue diagnosis within a gastrointestinal tract, comprising:
 providing an ingestible device comprising at least two probes, each operative to perform, along said gastrointestinal tract, a diagnostic image selected from the group, which consists of nuclear radiation of a radiopharmaceutical, scintillation of a scintillation liquid, responsive to nuclear radiation of a radiopharmaceutical, optical fluorescence of a fluorescing-pharmaceutical, optical fluorescence of a bare gastrointestinal-tract tissue, infrared thermography, temperature-differences, impedance, ultrasound reflection, magnetic resonance, and video, wherein each probe is operative to perform a different diagnostic image;
 ingesting said ingestible device;
 producing diagnostic signals with said probes, as said ingestible device travels in said gastrointestinal tract, thus forming said diagnostic images; and
 recording information of said diagnostic images.

According to an additional aspect of the present invention, said diagnostic image comprises diagnostic information as a function of time.

According to yet an additional aspect of the present invention, said diagnostic image comprises diagnostic information as a function of distance traveled by said ingestible device.

According to still an additional aspect of the present invention, said recording further includes transmitting said information extracorporeally, and recording said information by extracorporeal apparatus.

According to another aspect of the present invention, said recording further includes recording said information within said ingestible device.

According to still an additional aspect of the present invention, said method further includes administrating a pharmaceutical a predetermined time prior to said ingesting said ingestible device.

According to still an additional aspect of the present invention, said method further includes screening a large population.

According to still an additional aspect of the present invention, said method further includes screening for gastrointestinal-tract neoplasm.

According to still an additional aspect of the present invention, said method further includes diagnosing for a suspected pathology.

According to still an additional aspect of the present invention, said suspected pathology is malignant.

According to still an additional aspect of the present invention, said suspected pathology is nonmalignant.

According to an aspect of the present invention there is provided a method of locating a site in a gastrointestinal tract, comprising:
  evaluating a distance from a reference point to said site, by tracking an ingestible device within said gastrointestinal tract, vis a vis the walls of said gastrointestinal tract; and
  invasively measuring said distance along said gastrointestinal tract from said reference point to said site.

According to an additional aspect of the present invention, said evaluating said distance further includes:
  providing at least two sensors, arranged a predetermined distance apart, in the direction of travel;
  cross correlating a parameter sensed by said at least two sensors, at a time T and at a later time T+$\Delta$T;
  determining an incremental distance traveled by said ingestible device within said gastrointestinal tract, during period $\Delta$T; and
  summing incremental distances between the time said ingestible device passed by said reference point and the time said ingestible device passed by said site, to obtain said distance.

According to still an additional aspect of the present invention, said parameter, sensed by said at least two sensors, is selected from the group consisting of nuclear radiation of a radiopharmaceutical, scintillation light produced by a scintillation liquid, responsive to nuclear radiation of a radiopharmaceutical, optical fluorescence, reflected light, infrared radiation, temperature differences, impedance, and ultrasound reflection.

According to another aspect of the present invention, said evaluating said distance further includes:
  employing at least one roller, arranged to roll over the walls of said gastrointestinal tract; and
  employing a counter, in communication with said at least one roller, for counting the number of revolutions made by said at least one roller, between the time said ingestible device passed by said reference point and the time said ingestible device passed by said site.

According to an aspect of the present invention there is provided a method of locating a site in a gastrointestinal tract, comprising:
  estimating a distance from a reference point to said site, by tracking an ingestible device within said gastrointestinal tract, vis a vis an extracorporeal reference system; and
  invasively measuring said distance along said gastrointestinal tract from said reference point to said site.

According to an additional aspect of the present invention, said method further includes:
  tracking an ingestible device within said gastrointestinal tract, to obtain instantaneous x; y; z; values vis a vis said extracorporeal reference system;
  estimating an incremental distance traveled by said ingestible device within said gastrointestinal tract, during period $\Delta$T; and
  summing estimated incremental distances between the time said ingestible device passed by said reference point and the time said ingestible device passed by said site, to estimate said distance.

According to an additional aspect of the present invention, said tracking is selected from the group consisting of tracking with an intracorporeal RF transmitter and three extracorporeal RF receivers, tracking with an intracorporeal piezoelectric transducer and three extracorporeal piezoelectric transducer, tracking with at least one acceleration sensor, and tracking with a magnetic tracking and location system.

According to an aspect of the present invention there is provided a method of identifying a pathology, using a clock-like property of radioisotopes, comprising:
  providing a nuclear-radiation detector arranged for distinguishing between at least two forms of radiation, associated with at least two radioisotopes;
  administering a radiopharmaceutical which includes said at least two radioisotopes;
  performing diagnostic images by nuclear radiation for each of said at least two radioisotopes;
  evaluating an activity ratio for said at least two radioisotopes; and identifying said pathology, by an observed change in said activity ratio.

The present invention successfully addresses the shortcomings of the presently known configurations, by providing a an ingestible device, adapted to travel in the gastrointestinal tract and perform a diagnostic image of tissue therein. The diagnostic image comprises diagnostic information as a function of time, for example, since the ingestion of the ingestible device, or diagnostic information as a function of distance traveled by the ingestible device. Specifically, the ingestible device may be arranged to perform a diagnostic image of any of the following, or a combination thereof:
i. nuclear radiation of a radiopharmaceutical;
ii. scintillation of a scintillation liquid, responsive to nuclear radiation of a radiopharmaceutical;
iii. optical fluorescence of a fluorescing-pharmaceutical or of bare gastrointestinal-tract tissue;
iv. infrared radiation of the gastrointestinal-tract tissue, by infrared thermography;
v. temperature-differences along the gastrointestinal-tract tissue;
vi. impedance of the gastrointestinal-tract tissue;
vii. ultrasound reflection of the gastrointestinal-tract tissue; and
viii. magnetic resonance of the gastrointestinal-tract tissue.

Additionally, the ingestible device may be adapted for general screening of a large population, as well as for specific diagnoses of suspected pathologies.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 23 schematically illustrates a method of detector calibration, in accordance with a preferred embodiment of the present invention.

DESCRIPTION OF THE PREFERRED EMBODIMENTS

Figure 1A:
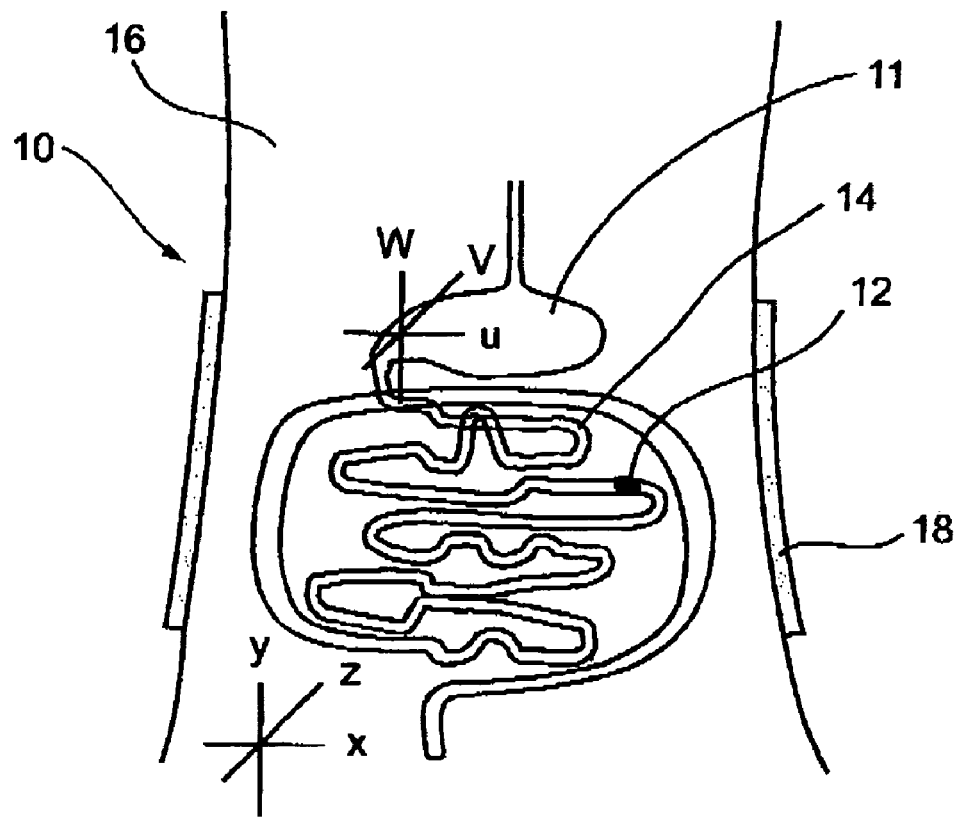
FIGS. 1A-1C schematically illustrate an overview of a diagnostic system, in accordance with the present invention.

The present invention is of an ingestible device, adapted to travel in the gastrointestinal tract and perform a diagnostic image of tissue therein. The diagnostic image comprises diagnostic information as a function of time, for example, since the ingestion of the ingestible device, or diagnostic information as a function of distance traveled by the ingestible device. Specifically, the ingestible device may be arranged to perform a diagnostic image of any of the following, or a combination thereof:

i. nuclear radiation of a radiopharmaceutical;
ii. scintillation of a scintillation liquid, responsive to nuclear radiation of a radiopharmaceutical;
iii. optical fluorescence of a fluorescing-pharmaceutical or of bare gastrointestinal-tract tissue;
iv. infrared radiation of the gastrointestinal-tract tissue, by infrared thermography;
v. temperature-differences along the gastrointestinal-tract tissue;
vi. impedance of the gastrointestinal-tract tissue;
vii. ultrasound reflection of the gastrointestinal-tract tissue; and
viii. magnetic resonance of the gastrointestinal-tract tissue.

Additionally, the ingestible device may be adapted for general screening of a large population, on the one hand, and for specific diagnoses of suspected pathologies, on the other.

The principles and operation of the ingestible device according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 1B:
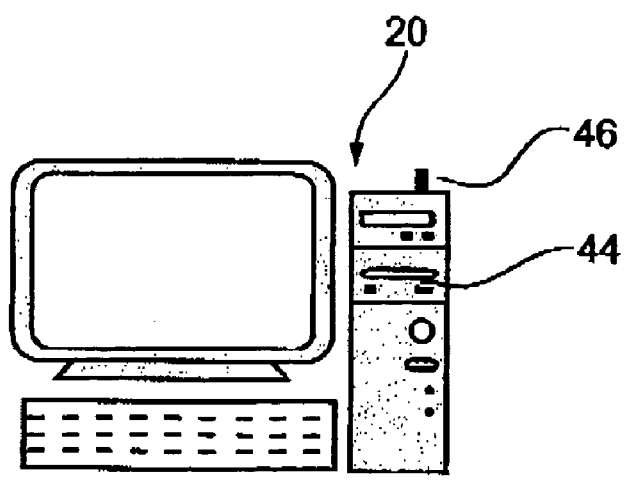
Figure 1C:
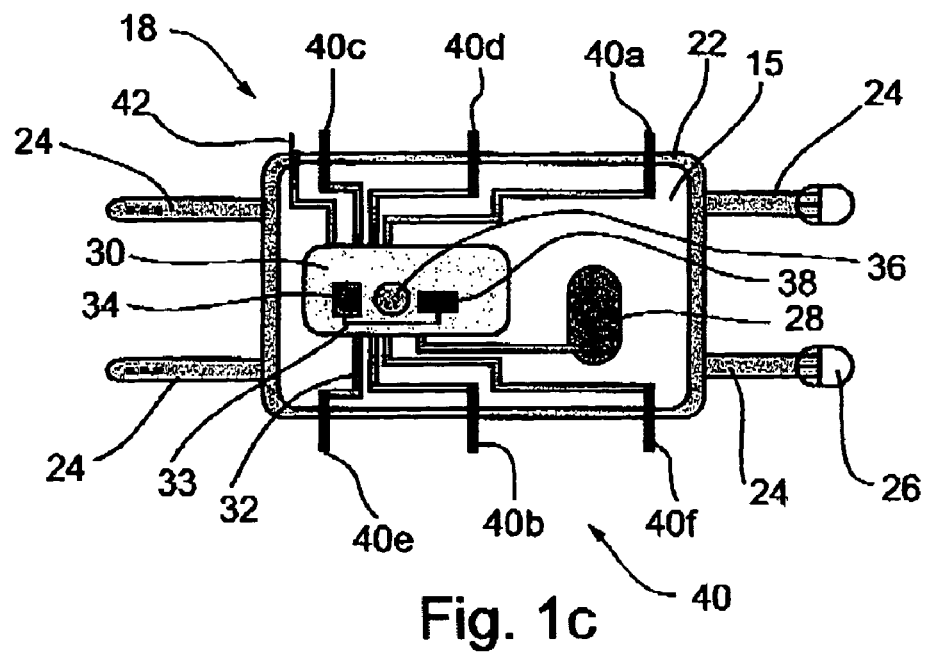

Referring to the drawings, FIGS. 1A-1C schematically illustrate components 12, 18, and 20 of a diagnostic system 10, in accordance with a preferred embodiment of the present invention.

Diagnostic system 10 includes an ingestible device 12, adapted to travel within a gastrointestinal track 14 of a body 16 and perform diagnosis of a tissue therein.

Diagnostic system 10 may further include extracorporeal apparatus 18, in wireless communication with ingestible device 12, adapted to be worn by body 16, or be placed near body 16. Additionally, diagnostic system 10 may include a computer station 20.

For example, extracorporeal apparatus 18 may be configured as a girdle-like garment 22, with straps 24 and buckles 26, arranged to be worn around the abdomen of body 16, to closely proximate gastrointestinal track 14. Alternatively, apparatus 18 may be worn as an elastic garment, a backpack, a handbag, or the like, or be placed near body 16.

Preferably, when worn by body 16, extracorporeal apparatus 18 farther includes an interface 15, such as a removable lining 15 or a removable wrapping 15, for providing a replaceable or a washable surface, between apparatus 18 and body 16.

Preferably, extracorporeal apparatus 18 includes a power source 28, a computer means 30, and a related circuitry 32. Additionally, computer means 30 includes a processor 34 and preferably, a memory 36 and a related circuitry 33. However, in accordance with the present invention, signal communication within extracorporeal apparatus 18 and (or) computer means 30 may be wireless. Preferably, computer means 30 further includes a removable data storage implement 38, such as a diskette, a minidisk, a CD, a tape or the like.

Apparatus 18 further includes at least one receiver 40, for receiving signals from ingestible device 12. Additionally, apparatus 18 may include two, or preferably three or more receivers 40, such as $40_A$, $40_B$, $40_C$, and possibly also $40_D$, $40_E$, and $40_F$. Communication of with ingestible device 12 may be by RF or by ultrasound radiation.

Apparatus 18 may further include a transmitter 42, or a transmitter and receiver system 42, for communicating with computer station 20, preferably, by RF radiation. Alternatively, communication with computer station 20 may be by cable.

Alternatively or additionally, transmitter 42 may be used for sending instructions to ingestible device 12.

Diagnostic system 10 may further include an extracorporeal reference system x; y; z, referenced for example, to any one of receivers 40 of apparatus 18. Additionally, diagnostic system 10 may further include an intracorporeal reference system u; v; w, referenced, for example, to the exit of a stomach 11.

Computer station 20 may be a Personal Computer, a minicomputer, a laptop, or the like. Preferably, computer station 20 includes a data reading implement 44, compatible with removable data-storage implement 38 of apparatus 18. Additionally, computer station 20 may include a receiver 46 or a transmitter and receiver system 46, for communicating with transmitter and receiver system 42 of apparatus 18, or with ingestible device 12. Computer station 20 may also be in communication with a network, for example, for accessing databanks and for contributing to databanks of diagnostic data, as relevant.

Figure 2A:
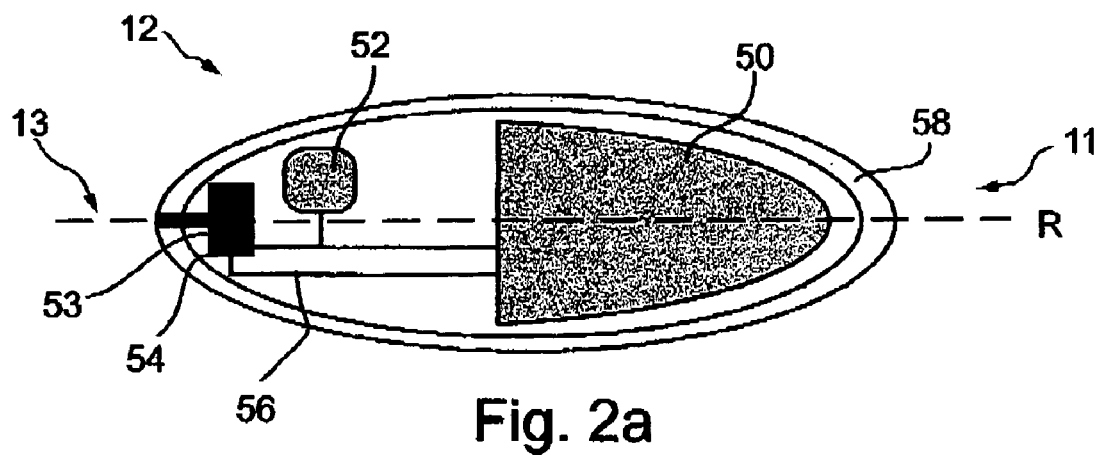
FIGS. 2A-2B schematically illustrate an ingestible device, in accordance with a preferred embodiment of the present invention.
Figure 2B:
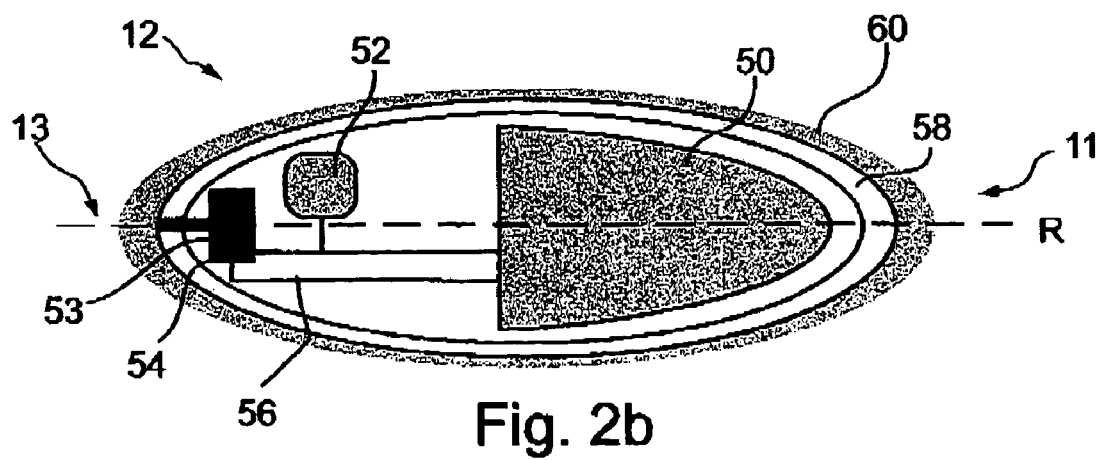

Referring further to the drawings, FIGS. 2A-2B schematically illustrate ingestible device 12, in accordance with a preferred embodiment of the present invention.

As seen in FIG. 2A, ingestible device 12 includes at least one probe 50, operative to perform a diagnostic image of tissue along gastrointestinal tract 14. Ingestible device 12 further includes a distal end 11 and a proximal end 13, with respect to stomach 11 (FIG. 1A). Furthermore, ingestible device 12 defines an axis R, parallel with its direction of travel.

Additionally, ingestible device 12 includes data-handling apparatus 53, in signal communication with probe 50, arranged for receiving and handling imaging data generated by probe 50.

Data-handling apparatus 53 may be, for example, a transmitter 54, arranged to transmit data, sensed by probe 50, to at least one receiver 40 of extracorporeal apparatus 18 (FIG. 1C), or directly to receiver 46 of computer station 20. Transmitter 54 may also transmit a periodic reference signal, which may include identifying details of body 16 and the date and (or) time of the diagnosis.

In accordance with a preferred embodiment of the present invention, transmitter 54 and at least one receiver 40 (FIG. 1C) are arranged for RF communication, which may further include multichannel communication. For example, data may be transmitted in one channel, and a reference signal may be transmitted in another. Additionally, where a plurality of probes is used in conjunction with ingestible device 12, as will be described below, each probe may be assigned a channel. Alternatively, transmitter 54 may be arranged to communicate with at least one receiver 40 by ultrasound radiation.

Ingestible device 12 may further include a power source 52 and a related circuitry 56. However, signal communication within ingestible device 12 may be wireless.

Probe 50, data-handling apparatus 53, power source 52 and related circuitry 56 are encapsulated within a shell 58. Shell 58 may be formed of an inert biocompatible material, such as, polycarbonate, polyethylene, natural rubber, silicon, or a composite formed for example, as an epoxy resin impregnated with glass fibers.

Additionally, shell 58 may be coated with a candy-like coating 59, formed, for example, of crusted sugar, sugared gelatin, chocolate, or the like.

The overall size of ingestible device 12 should be small enough for easy ingestion, for example, about 2 cm in length, and about 1 cm in width. It will be appreciated that smaller dimensions are possible. Additionally, somewhat larger dimensions may be possible.

Preferably, ingestible device 12 is disposable. Ingestible device 12 may be disposed naturally, by the body, or retrieved for examination, and then disposed. Alternatively, ingestible device 12 may be retrieved for repeated use, following cleaning and sterilization.

In accordance with a preferred embodiment of the present embodiment seen in FIG. 2A, device 12 includes a minimal number of components, necessary for diagnosis. As such, it is relatively inexpensive, thus suitable as a general screening device. Additionally, noise, which may arise from interference between components, is kept at a minimum.

In accordance with another preferred embodiment of the present invention, seen in FIG. 2B, ingestible device 12 is arranged for retrieval and repeated use and further includes a second shell 60. Second shell 60 may be formed, for example, of a thin polycarbon layer, or a similar material, and is replaced between uses, following cleaning and sterilization. Additionally, second shell 60 may comprise a candy-like coating. Second shell 60 is utilized in order to overcome any uneasiness, associated with ingesting a device that has been through the gastrointestinal tract of another.

Referring further to the drawings, FIGS. 3A-3D schematically illustrate ingestible device 12, arranged for imaging nuclear radiation of a radiopharmaceutical, and a method of imaging thereof, in accordance with a preferred embodiment of the present invention. Preferably, probe 50 comprises a nuclear-radiation detector 49. Ingestible device 12 may further include transmitter 54, power source 52 and related circuitry 56, as has been described hereinabove, in conjunction with FIG. 2A.

Nuclear-radiation detector 49 may comprise at least one Cadmium Zinc Telluride crystal or at least one Cadmium Telluride crystal, operative to detect both gamma and beta radiation. Additionally, two or more crystals may be employed. These may be obtained from eV Products, PA, USA) 375 Saxonburg Blvd. Saxonburg, Pa. 16056. Alternatively, another nuclear-radiation detector 49, preferably operative to detect both gamma and beta radiation, may be used, as known.

Preferably, nuclear-radiation detector 49 is not collimated; rather, it is operative to detect nuclear radiation from any directions. Alternatively, nuclear-radiation detector 49 may include a honeycomb-type collimator, arranged around its circumference, operative to detect nuclear radiation from any directions. Alternatively, another collimator may be used, as known.

Preferably, nuclear-radiation detector 49 is operative to detect nuclear radiation across a wide energy spectrum from about 6.0 KeV to about 1.5 MeV, associated with beta and gamma radiation. Alternatively, gating may be performed to detect radiation at a specific energy range, associated with a particular isotope. As an example, nuclear-radiation detector 49 may be gated for incoming radiation at an energy of about 28 KeV, which corresponds to gamma photons, emitted by $I^{125}$. As another example, nuclear-radiation detector 49 may be gated for incoming radiation at an energy of about 0.9 MeV, which corresponds to beta energy of $P^{32}$. Where two or more crystals are used, one may be gated for one energy range, and the other, for another energy range, in order to detect specific radiation emitted by different radioisotopes, for example, to minimize background interference.

Preferably, nuclear-radiation detector 49 generates a current pulse that is proportional to the energy of a detected particle, with sufficient time resolution to detect each gamma and (or) beta particle separately. Thus, gating may be performed by the electronic circuitry, according to the particle's energies.

Sometime prior to the ingestion of ingestible device 12, for example, several hours to about two days prior to the ingestion, a radiopharmaceutical is administered to body 16. Preferably, administration is by injection. Alternatively, administration may be oral or intravenous. The radiopharmaceutical may include a monoclonal antibody such as anti-CEA, anti-TAG-72, or another antibody, labeled with a radioisotope, for example, any one of Technetium $Tc^{99m}$, Iodine $I^{125}$, $I^{123}$, $I^{131}$, and $I^{133}$, Indium $In^{111}$, Gallium $Ga^{67}$, thalium $Tl^{201}$, fluorine $F^{18}$ and $P^{32}$ Among these, $Ga^{67}$, $I^{131}$, and $P^{32}$ emit ☐ ☐ ☐ ☐ radiation.

In accordance with the present invention, ☐ ☐ ☐ ☐ radiation is of particular use, in the small intestine. In water, or body tissue, ☐ ☐ ☐ ☐ radiation has a range of only a few millimeters before it is absorbed. Yet in the small intestine, ingestible device makes contact with the walls of gastrointestinal tract 14, and when gated to a particular beta energy, is operative to detect ☐ ☐ ☐ ☐ radiation, without the interference of background radiation.

The radiopharmaceutical may include two or more antibodies, each labeled by a different isotope. For example, a cocktail of anti-CEA labeled with any one of $I^{125}$, $I^{123}$, $I^{131}$, $I^{133}$ or $Tc^{99m}$ and anti-TAG-72 labeled with Indium $In^{111}$ may be used.

Additionally, the radiopharmaceutical may include a mixture of two radioisotopes, for example, anti-CEA labeled with $I^{131}$ and anti-CEA labeled with $I^{133}$.

Preferably, Prior to the ingestion of ingestible device 12, the patient is prepared so that minimal contents are present in gastrointestinal track 14.

For illustrative purposes, it is assumed that a pathological site 82 exists along gastrointestinal tract 14. The radiopharmaceutical tied to pathological specific antibodies is likely to concentrate at site 82, generating nuclear radiation 81.

Figure 3A:
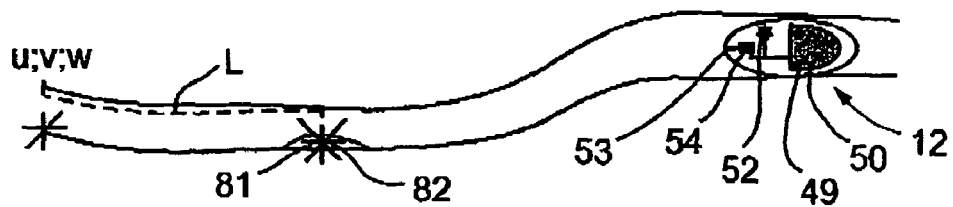
FIGS. 3A-3D schematically illustrate an ingestible device, comprising a probe arranged as a nuclear-radiation detector, in accordance with a preferred embodiment of the present invention.

As ingestible device 12 travels in gastrointestinal tract 14, as seen in FIG. 3A, it transmits data, representing nuclear radiation counts, to extracorporeal computer means 30 (FIG. 1C). Preferably, computer means 30 records the incoming data as a function of time, from the time of ingestion.

Preferably, computer means 30 (FIG. 1C) records the data as the number of counts during a predetermined time interval, or time channel, for all the time intervals, from the time of ingestion. The predetermined time intervals may be, for example, 30 seconds, 1 minute, or 10 minutes, or another predetermined value, and may depend on the expected count rate. For example, if ingestible device 12 takes 70 hours (=4200 minutes) to travel the length of gastrointestinal tract 14, computer means 30 may collect the data in 4200 channels of 1-minute intervals, or in 420 channels of 10-minute intervals, or in any other number of channels that is predetermined. Data manipulation may later coalesce channels to aid in interpretation. For example, data may be collected and stored in very fine channels of, for example, 1 second, and later coalesced and displayed in channels of 10 minutes.

Figure 3B:
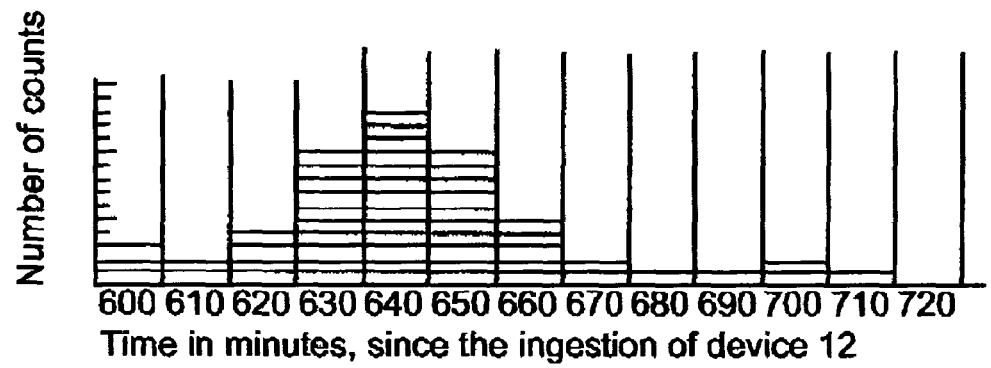

FIG. 3B schematically illustrates nuclear-radiation counts in 10-minute channels, at 10 to 12 hours (600-720 minutes) after ingestion, as may be generated by computer means 30 (FIG. 1C). A statistically significant radiation peak, centered around 640 minutes after ingestion, is indicative of a suspected pathology, such as a neoplastic tissue, at that location.

Although a location known only as 640 (=10.7 hours) after ingestion is not necessarily well defined, it is nonetheless somewhat informative. Generally, ingestible device 12 takes about 70 hours or approximately 3 days to complete its route. Of these, the later 30 to 50 hours are spent in the colon. Thus a surgeon may estimate that at about 11 hours after ingestion, ingestible device 12 was probably in the small intestine.

A method of identifying the location of pathological site 82 is described hereinbelow, in conjunction with FIGS. 3C and 3D. Alternative methods of identifying the location of pathological site 82 are described hereinbelow, in conjunction with FIGS. 13A-19B.

As taught by U.S. Pat. No. 5,279,607, to Schentag et al., entitled, "Telemetry Capsule and Process," and U.S. Pat. No. 5,396,366 to A'Andrea et al., entitled, Sampling capsule and process," whose disclosures are incorporated herein by reference, at least three receivers, such as receivers 40$_A$, 40$_B$ and 40$_C$ (FIG. 1C) arranged at different locations, and dedicated algorithms, may be used to determine a precise location of the source of radiation, transmitter 54 (FIG. 2A) of ingestible device 12, at a given time.

However, due to intrinsic motion of gastrointestinal tract 14 within body 16 (FIG. 1A), as part of the digestive process, a precise location of site 82, with respect to extracorporeal reference system x; y; z, is meaningless. The same diagnosis, performed a week later, with the same extracorporeal reference system x; y; z, will produce different x,y,z values for site 82.

Nonetheless, a distance L traveled by ingestible device 12, from intracorporeal reference system u; v; w, for example, the exit of stomach 11, to site 82, may be estimated, based on instantaneous x; y; z values of ingestible device 12. This distance is of value, as a surgeon may measure, invasively, along gastrointestinal tract 14 and arrive at site 82.

For this purpose, precise, instantaneous locations of ingestible device 12 may be estimated, vis a vis plurality of receivers 40 of extracorporeal apparatus 18 (FIG. 1C), for each time interval i, by computer means 30. Preferably, extracorporeal reference system x; y; z (FIG. 1A) is correlated with the locations of receivers 40, for example, by using one of the receivers as position (0; 0; 0). The instantaneous x,y,z, values of each time interval i may be denoted as $(x,y,z)_i$.

Figure 3C:
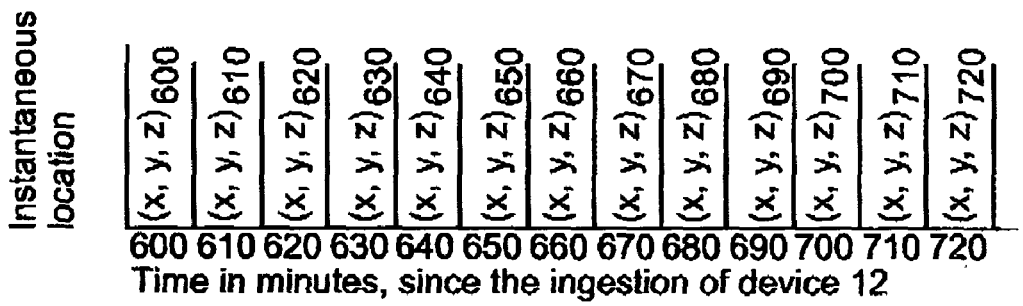

FIG. 3C schematically illustrates instantaneous $(x; y; z)_i$ values of ingestible device 12, as obtained with receivers $40_A$, $40_B$, and $40_C$. Based on theses values, an estimated distance L that has been traveled by ingestible device 12, from intracorporeal reference system u; v; w to site 82 may be calculated, by summing over estimated incremental distances $\Delta L$, as follows:

$$L = \Sigma \Delta L, \text{ where } \Delta L = [(x_{i+1}-x_i)^2 + (y_{i+1}-y_i)^2 + (z_{i+1}-z_i)^2]^{1/2}$$

Preferably, the instantaneous values of $(x; y; z)_i$ are obtained at very short time intervals, for example, of a few seconds.

Figure 3D:
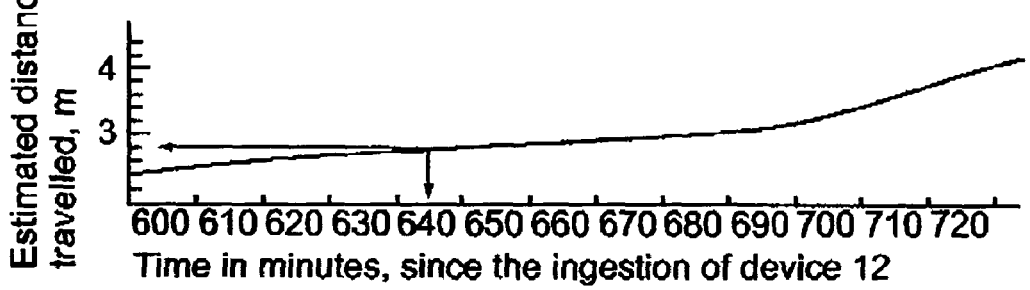

FIG. 3D schematically illustrates estimated distance L as a function of time, since ingestion. Alternatively, another time may be used, for example, the time from intracorporeal reference system u; v; w. Thus, a surgeon may observe, for example, that at 640 minutes after ingestion, which may correspond, for example, to 240 minutes from intracorporeal reference system u; v; w, ingestible device 12 passed near site 82, having traveled approximately 2.8 meters within gastrointestinal tract 14.

Thus, a diagnostic image of nuclear radiation may comprise diagnostic information as a function of time, as seen in FIG. 3A, or diagnostic information as a function of distance traveled by ingestible device 12, based on the information seen in FIG. 3D.

With reference to FIGS. 3A-3D, it will be appreciated that computer station 20 (FIG. 1B) may be used in tandem with, or in place of computer means 30 (FIG. 1C).

Referring further to the drawings, FIGS. 4A-4D schematically illustrate ingestible device 12, arranged for imaging nuclear radiation of at least two radioisotopes, and a method of imaging thereof, in accordance with another preferred embodiment of the present invention.

The clock-like property of radioisotopes may by itself serve for techniques to identify pathological sites in the body, as follows:

In a stagnant pool, the time-dependent isotope concentration N(t) of an isotope having an initial concentration $N_0$ and a decay constant $\lambda$ may be described as, $$N(t) = N_0 e^{-\lambda t}.$$

In the body, cleansing may be described by a cleansing rate constant $\phi$. Thus, the time-dependent isotope concentration in the body decreases by decay and cleansing, at a rate constant of $\lambda + \phi$. Except where $\phi \gg \lambda$, the decrease rate constant $\lambda + \phi$ is unique to each isotope.

At a pathological site, while buildup occurs by absorption, removal takes place by decay and release, wherein release may be described by a release rate constant $\eta$. Thus, the time-dependent isotope concentration at the pathological site decreases at a rate constant of $\lambda + \eta$. As in the case of the body in general, except where $\eta \gg \lambda$, the decrease rate constant $\lambda + \eta$ is unique to each isotope.

In essence, a given isotope behaves as if it has different effective decay constants, as follows: $\lambda + \phi$ for the body in general, and $\lambda + \eta$ for the pathological site. Since the antibody or radiopharmaceutical is selected specifically because of a hold up mechanism within pathologies, which is markedly different from that of the tissue in general (i.e., $\eta \ll \phi$), these effective decay constants may be used to identify a pathological site.

A first technique to identify a pathological site is based on administrating a radiopharmaceutical which contains two radio-isotopes, A and B, preferably bound to the same antibody. Within the body, the time-dependent concentration of the two radio-isotopes will decrease at the rates, $\lambda_A + \phi$ and $\lambda_B + \phi$ for A and B, respectively, and a time-dependent concentration ratio of A/B will depend on these values. However, at a pathological site, their time-dependent concentrations will decrease at the rates, $\lambda_A + \eta$ and $\lambda_B + \eta$ for A and B, respectively. Thus, a change in the isotopic concentration ratio may occur at a pathological site. The change will be observed by a change in the activity ratio between the tissue in general and the pathological site.

In FIGS. 4A-4D, the administration of radiopharmaceutical to body 16 has included a cocktail of two isotopes, $I^{131}$ and $I^{133}$. Additionally, nuclear-radiation detector 49 has been arranged to distinguish between photons of a first energy, associated with $I^{131}$ and photons of a second energy, associated with $I^{133}$, based on the current pulses that are generated, as has been described hereinabove.

Figure 4A:
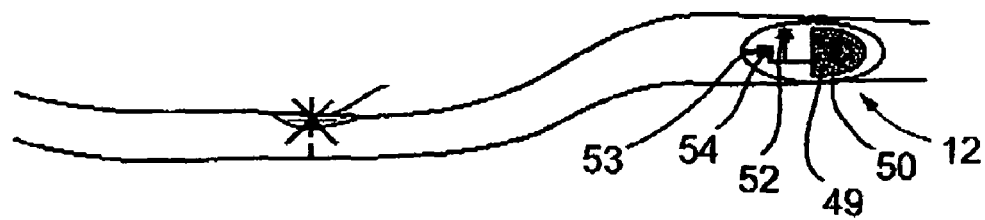
FIGS. 4A-4D schematically illustrate an ingestible device, comprising probe, arranged as a nuclear-radiation detector, in accordance with another preferred embodiment of the present invention.
Figure 4B:
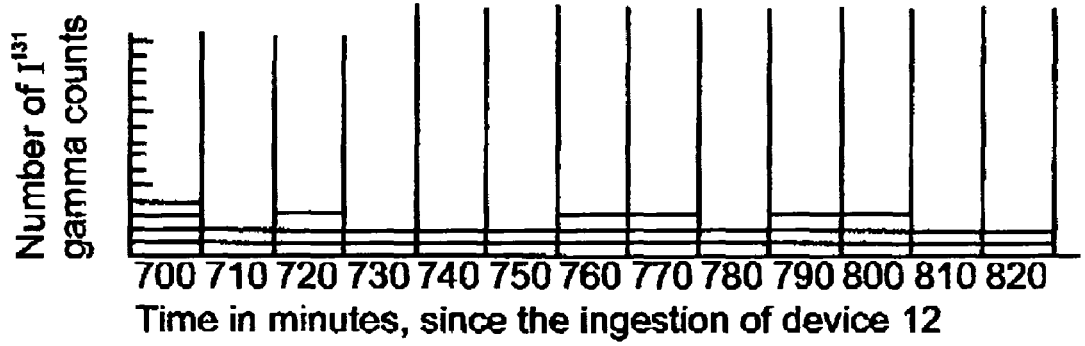
Figure 4C:
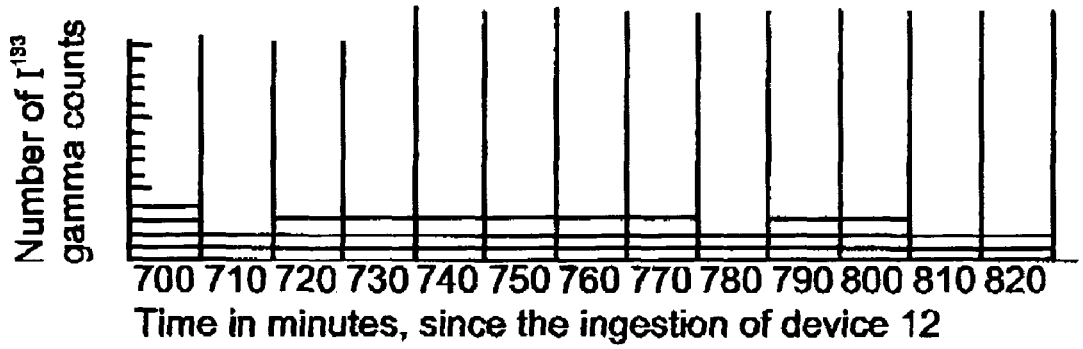

As seen in FIG. 4A, a pathological site 92 may exist in gastrointestinal tract 14, for example, at about 540 minutes from the time of ingestion of ingestible device 12. Additionally, as seen in FIGS. 4B and 4C, pathological site 92 is too small to generate statistically significant photon peaks of radiation counts either of $I^{131}$ or of $I^{133}$.

Figure 4D:
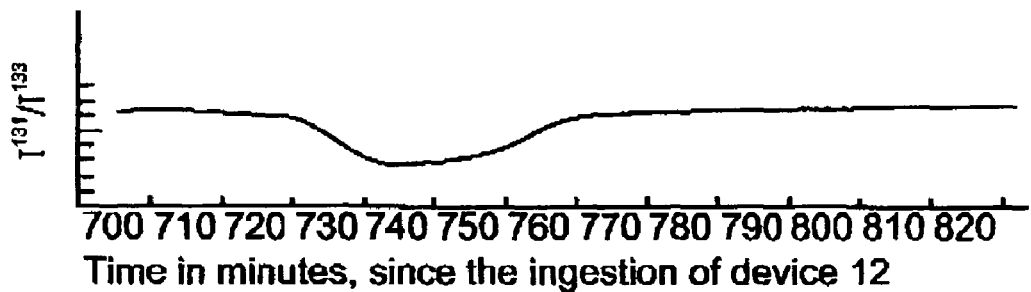

However, as seen in FIG. 4D, a change in the isotopic activity ratio, $I^{131}$ to $I^{133}$, at site 92, is indicative of a suspected pathology.

It will be appreciated that a change in the isotopic activity ratio may be observed even when statistically significant peaks of nuclear-radiation counts are observed, and may be used as a confirmation.

A diagnostic image of the change in the isotopic activity ratio may comprise diagnostic information as a function of time, as seen in FIG. 4D, or diagnostic information as a function of distance traveled by ingestible device 12, based on the information seen in FIG. 3D.

A second technique to identify a pathological site is based on administrating a radiopharmaceutical which contains two radio-isotopes, A and B, wherein only A is bound to an antibody. For the body in general, the time-dependent concentration of the two radio-isotopes will decrease at the rates, $\lambda_A + \phi$ and $\lambda_B + \phi$ for A and B, respectively, and the time-dependent concentration ratio of A/B will depend on these values. However, at a pathological site, the time-dependent concentration of A will decrease at the rate, $\lambda_A + \eta$, while that of B will decrease at the rate $\lambda_B + \phi$, and the time-dependent concentration ratio of A/B at the pathological site will depend on these values. Again, a change in the isotopic activity ratio may be observed near a pathological site.

In accordance with the present invention, the techniques for detecting a pathological site, using activity ratios of two isotopes may be optimized by the selection of isotopes, antibodies, the form of administration and the waiting period between the administration of the radiopharmaceutical and the ingestion of ingestible device 12. Additionally, three or more radio-isotopes may be used. Furthermore, the isotopes need not be chemically identical. Additionally, they need not be bound to the same antibody. Many variations of the aforementioned techniques, that rely on the clock-like property of radio-isotopes to identify the hold-up mechanism, associated with a pathological site are possible, and are within the scope of the present invention.

In accordance with the present invention, nuclear-radiation detector 49 may include features taught by U.S. Pat. No. 4,801,803 to Denen, et al., entitled, "Detector and localizer for low energy radiation emissions," U.S. Pat. No. 5,151,598 to Denen, entitled, "Detector and localizer for low energy radiation emissions," U.S. Pat. No. 4,893,013 to Denen et al., entitled, entitled "Detector and Localizer for Low Energy Radiation Emissions," and U.S. Pat. No. 5,070,878 to Denen, entitled, "Detector and localizer for low energy radiation emissions," and U.S. Pat. No. 6,259,095, to Boutun, et al., entitled, "System and apparatus for detecting and locating sources of radiation," whose disclosures are incorporated herein by reference.

Figure 5:
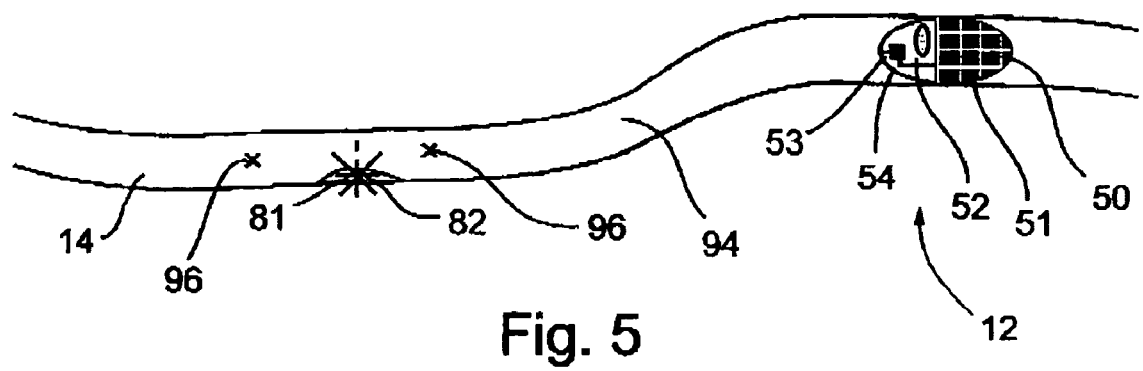
FIG. 5 schematically illustrates an ingestible device, comprising a probe arranged as at least one photo-detector, in accordance with yet another preferred embodiment of the present invention.

Referring further to the drawings, FIG. 5 schematically illustrates ingestible device 12, arranged for indirect imaging of nuclear radiation by the scintillation that it produces, in accordance with still another preferred embodiment of the present invention. The present embodiment provides a technique for identifying a pathological site indirectly, with a scintillation liquid. Accordingly, probe 50 of ingestible device 12 includes a photodetector 51. Ingestible device 12 may further include transmitter 54, power source 52 and related circuitry 56, as has been described hereinabove, in conjunction with FIG. 2A.

In accordance with the present embodiment, the administration of pharmaceuticals to body 16 (FIG. 1A) includes a radiopharmaceutical and a scintillation liquid. White the radiopharmaceutical is administered, preferably, by injection, between several hours to about two days prior to the ingestion of ingestible device 12, the scintillation liquid is preferably administered orally, about two hours prior to the ingestion of ingestible device 12.

Preferably, prior to the ingestion of ingestible device 12, body 16 is prepared so that minimal content is present in gastrointestinal tract 14.

The scintillation liquid may be obtained, for example, from IN/U.S. Systems, Inc., 5809 North 50th Street, Tampa, Fla. 33610-4809, which offers two biodegradable, non-toxic scintillation cocktails, IN-FLOW BD and IN-FLOW ES. Both products have low viscosity to assure pumpability, are non-hazardous and can be disposed of as normal liquid waste.

As ingestible device 12 travels within gastrointestinal tract 14, it is surrounded by a scintillation liquid 94, which produces scintillation to gamma and beta radiation. In the vicinity of pathological site 82, scintillation 96 is produced within the liquid, generated by nuclear radiation 81 from the radiopharmaceutical bound to site 82. Scintillation 96 will be detected by photodetector 51, and transmitted to apparatus 18, via transmitter 54.

A diagnostic image of scintillation may comprise diagnostic information as a function of time, in a manner analogous to that seen in FIG. 3A, or diagnostic information as a function of distance traveled by ingestible device 12, based on the information seen in FIG. 3D.

Photodetector 51 may comprise a single photo-sensing diode, or two or more photo-sensing diodes. Examples of photo-sensing diodes that may be used for the present embodiment, include NT55-754 or NT53-372 described in www.edmundoptics.com/IOD/DisplayProduct.cfm?productid=2232, of Edmund Industrial Optics.

Figure 6:
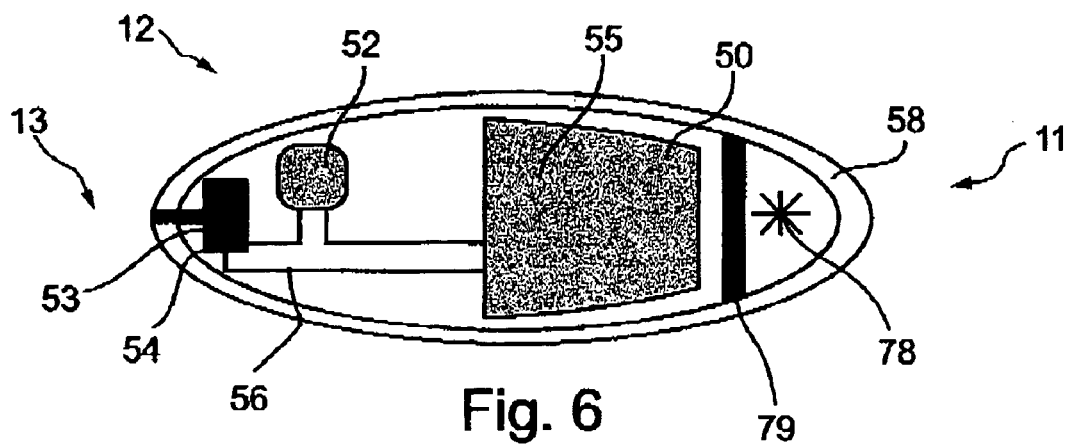
FIG. 6 schematically illustrates an ingestible device, comprising a probe arranged as at least one detector optical fluorescence and a light source, in accordance with still another preferred embodiment of the present invention.

Referring further to the drawings, FIG. 6 schematically illustrates ingestible device 12, arranged for imaging optical fluorescence, in accordance with a preferred embodiment of the present invention. The optical fluorescence may be of a fluorescing-pharmaceutical, or of bare gastrointestinal-tract tissue.

Preferably, probe 50 comprises a photodetector 55, similar, for example, to photodetector 51, described hereinabove, in conjunction with FIG. 5, but which preferably further includes a color filter, for example, NT46-149 obtained from Edmund Industrial Optics, hereinabove, so as to be sensitive to a specific color. Alternatively, photodetector 51 may comprise more than one photodiode, each having a different filter.

Additionally, ingestible device 12 further includes an excitation source 78, preferably, a laser light source 78, distal to photodetector 55. Laser light source 78 may be fitted into ingestible device 12 as taught by U.S. Pat. No. 6,324,418 Crowley, entitled, "Portable tissue spectroscopy apparatus and method," whose disclosure is incorporated herein by reference. A light barrier 79 may separate source 78 and photodetector 55.

Ingestible device 12 may further include transmitter 54, power source 52 and related circuitry 56, as has been described hereinabove, in conjunction with FIG. 2A.

A diagnostic image of optical fluorescence may comprise diagnostic information as a function of time, in a manner analogous to that seen in FIG. 3A, or diagnostic information as a function of distance traveled by ingestible device 12, based on the information seen in FIG. 3D.

Known fluorescing pharmaceuticals, which give well structured fluorescence spectra include hematoporphyrin derivatives (HPD), when excited in the Soret band around 405 nm. Additionally, they include dihematoporphyrin ether/ester (DHE), hematoporphyrin (HP), polyhematoporphyrin ester (PHE), and tetrasulfonated phthalocyanine (TSPC), when irradiated at 337 nm, for example by an $N_2$ laser. Each of these, or a combination of these, or other known fluorescing-pharmaceutical and various combinations thereof may be used, in accordance with the present invention.

As taught by U.S. Pat. No. 5,115,137, to Andersson-Engels, et al, entitled, "Diagnosis by means of fluorescent light emission from tissue," whose disclosure is incorporated herein by reference, the fluorescing-pharmaceutical may include tetrasulfonated phthalocyanine (TSPC), and source 78 may comprise an $N_2$ laser for irradiation at 337 nm.

Alternatively, as taught by U.S. Pat. No. 4,336,809, to Clark entitled, "Human and animal tissue photoradiation system and method," whose disclosure is incorporated herein by reference, the fluorescing-pharmaceutical may include a hematoporphyrin or hematoporphyrin derivative, and source 78 may comprise a xenon ion laser. According to Clark, xenon ion laser has a singly ionized lasing transition in the red range, at a wavelength of about 627 nanometers, which approximately matches the red absorption peak of hematoporphyrin. Additionally, xenon ion laser has a group of doubly ionized lines at wavelengths of about 406, 421, 424, and 427 nanometers. These approximately match the 407 nanometer blue absorption peak of hematoporphyrin.

Alternatively, as taught by Clark hereinabove, the pharmaceuticals that are administered may include a hematoporphyrin or hematoporphyrin derivative, and source 78 may be a krypton ion laser which has 406.7/413.1 nanometer lines matching the 407 nanometer absorption peak of hematoporphyrin.

As ingestible device 12 travels within gastrointestinal tract 14, an optical fluorescence image of the fluorescing-pharmaceutical may be generated. The information of the fluorescence image may be recorded in a manner analogous to that described in conjunction with FIG. 3A.

It will be appreciated that other pharmaceuticals may be used, having absorption peaks that may be specifically matched by an appropriate laser.

Unlike U.S. Pat. No. 6,324,418 to Crowley, hereinabove, which teaches a ingestible pill for performing laser-excited optical fluorescence of bare tissue, the present invention includes administrating a fluorescence pharmaceutical and inducing it at an energy that specifically matches an absorption peak of the pharmaceutical.

However, in accordance with other preferred embodiments of the present invention, ingestible device 12 may be arranged for imaging optical fluorescence of bare gastrointestinal-tract tissue.

Figure 7:
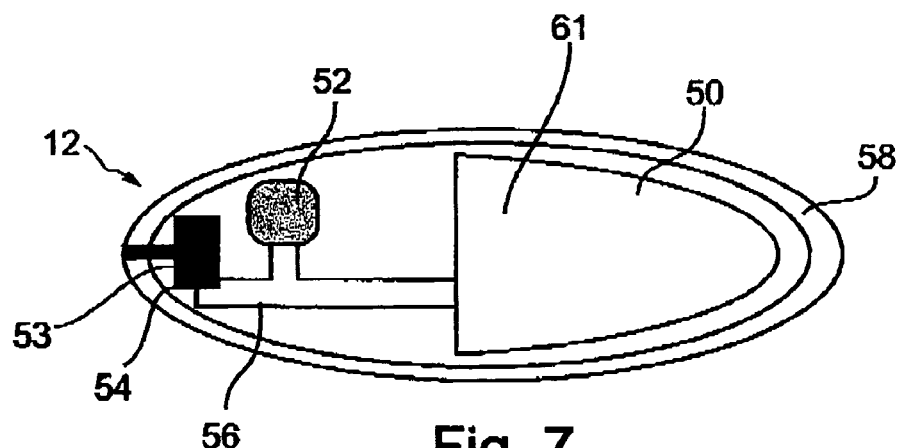
FIG. 7 schematically illustrates an ingestible device, comprising a probe, arranged for infrared thermography, in accordance with yet another preferred embodiment of the present invention.

Referring further to the drawings, FIG. 7 schematically illustrates ingestible device 12, arranged for imaging infrared radiation of the gastrointestinal-tract tissue, by infrared thermography, in accordance with a preferred embodiment of the present invention.

In the small intestine, ingestible device 12 is likely to make contact with the walls of gastrointestinal tract 14. However, in the colon, contact with the walls is unlikely. Infrared thermography, which measures thermal energy emitted from a surface without contact, and produces a temperature image for analysis, is thus uniquely suitable for use with ingestible device 12.

Preferably, probe 50 comprises an infrared thermography detector 61, formed as photodetector 51, described hereinabove, in conjunction with FIG. 5, which further includes an IR filer, for example, IR-NT54-518, obtained from Edmund Industrial Optics hereinabove. Alternatively, infrared thermography detector 61 may be formed of a single photo-sensing diode, or two or more photo-sensing diodes for IR such as EPD-740-0/1.0-IR selective photo diode, obtained from ROITHNER LASERTECHNIK, A-1040 Vienna, Austria, Schoenbrunner Strasse.

Ingestible device 12 may further include transmitter 54, power source 52 and related circuitry 56, as has been described hereinabove, in conjunction with FIG. 2A.

As ingestible device 12 travels within gastrointestinal tract 14, an image of tissue temperature may be obtained. A pathological site, such as site 82 (FIG. 3A) is likely to be at higher temperature than the surrounding tissue, and may thus produce a thermography peak, indicative of pathology.

A diagnostic image of tissue temperature may comprise diagnostic information as a function of time, in a manner analogous to that seen in FIG. 3A, or diagnostic information as a function of distance traveled by ingestible device 12, based on the information seen in FIG. 3D.

Figure 8A:
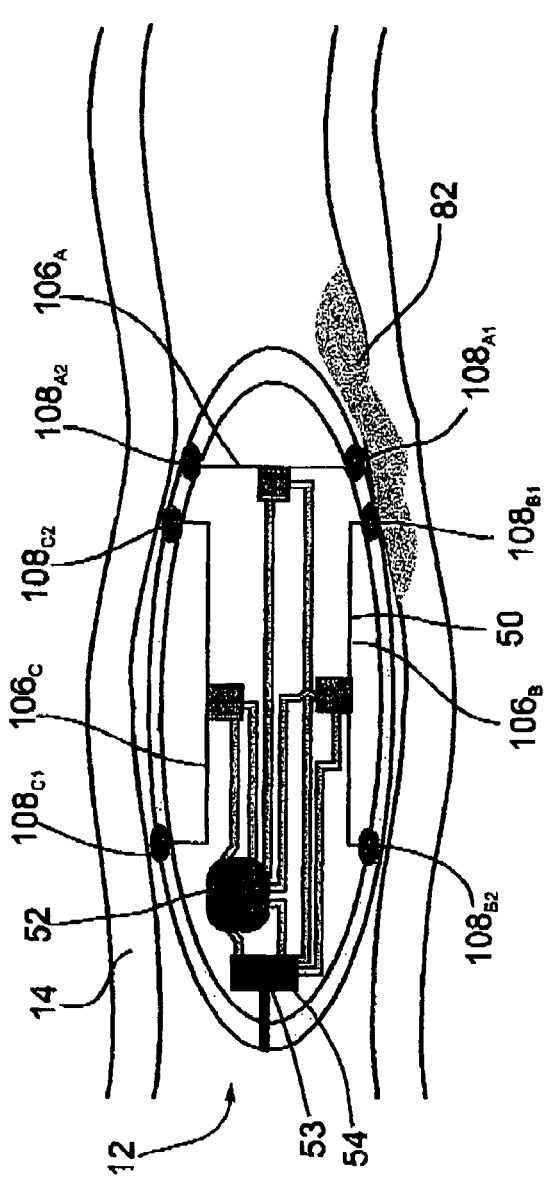
FIGS. 8A and 8B schematically illustrate the operation of an ingestible device comprising at least one thermocouple probe, in accordance with yet another preferred embodiment of the present invention.
Figure 8B:
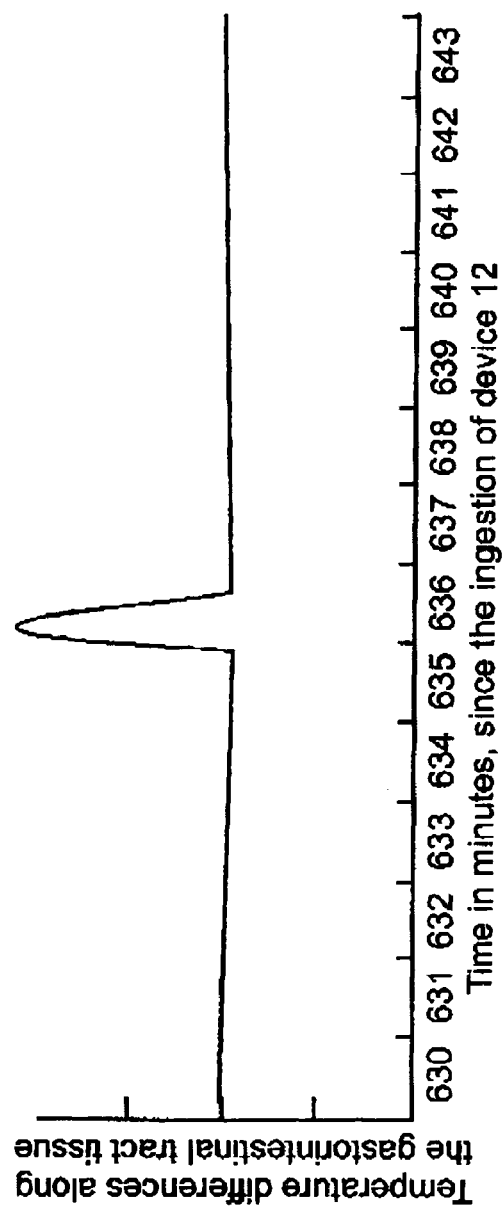

Referring further to the drawings, FIGS. 8A and 8B schematically illustrate ingestible device 12, arranged for imaging temperature-differences along the gastrointestinal-tract tissue, and a method of imaging thereof, using at least one thermocouple $106_A$, in accordance with a preferred embodiment of the present invention.

A thermocouple is a known means for measuring temperature. It includes two wires, made of different metals, connected at one end and very close, but not connected, at the other end. When the connected end of the thermocouple is placed in an area of higher temperature than the other end, a voltage builds up between the wires, at the other end.

At least one thermocouple probe $106_A$ has tips $108_{A1}$ and $108_{A2}$ which preferably are butt with the external surface of shell 58. Temperature differences may thus be measured between tips $108_{A1}$ and $108_{A2}$. Preferably probe 50 includes additional thermocouples, such as $106_B$, having tips $108_{B1}$ and $108_{B2}$, and $106_C$, having tips $108_{C1}$ and $108_{C2}$. Ingestible device 12 may further include transmitter 54, power source 52 and related circuitry 56, as has been described hereinabove, in conjunction with FIG. 2A.

In the small intestine, direct contact between ingestible device 12 and the walls of gastrointestinal tract 14 is likely to occur. As ingestible device 12 travels within gastrointestinal tract 14, particularly in the small intestine, differences in tissue temperatures are detected, as tips $108_A$, $108_B$, and $108_C$ form contact with tissue of gastrointestinal tract 14. At an interface between a healthy tissue and a pathology, for example, where tip $108_{A1}$ is in contact with the pathology, and tip $108_{A2}$ is in contact with a healthy tissue, a spike, indicative of a temperature gradient between the two types of tissue, may be observed.

A diagnostic image of tissue temperature differences may comprise diagnostic information as a function of time, in the manner seen in FIG. 8B, or diagnostic information as a function of distance traveled by ingestible device 12, based on the information seen in FIG. 3D.

Figure 9A:
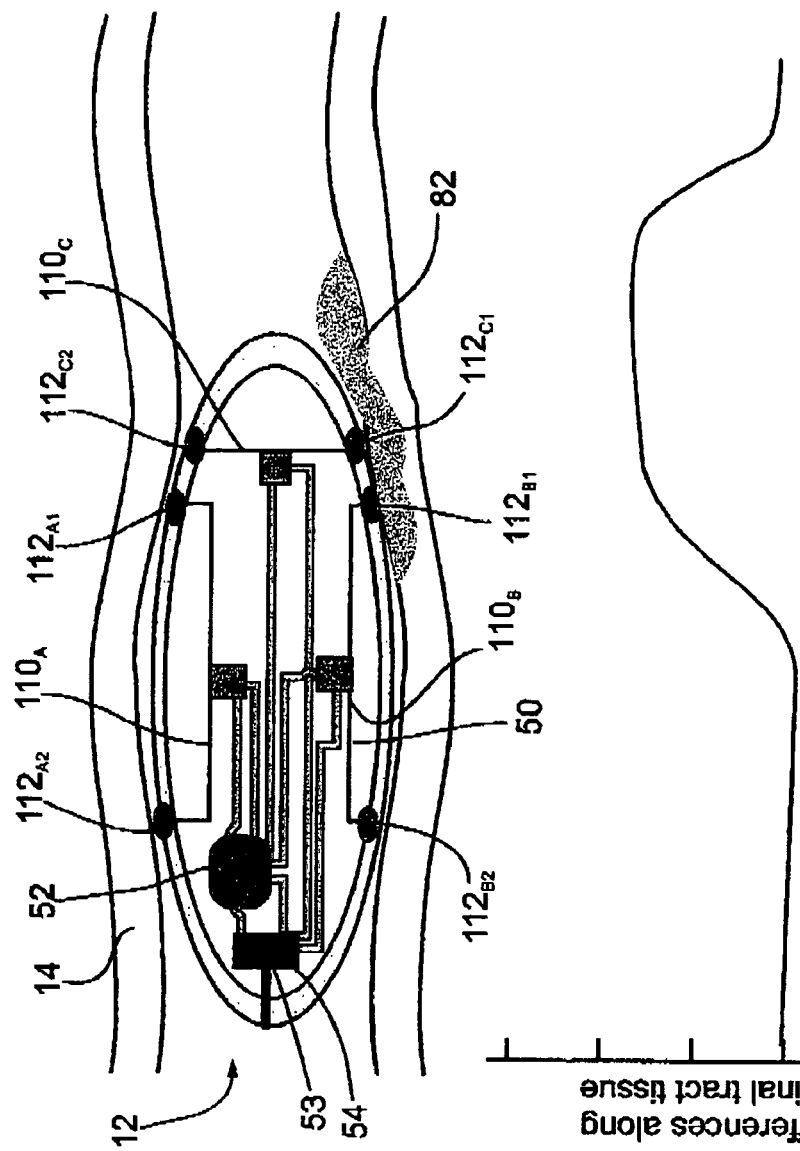
FIGS. 9A and 9B schematically illustrate the operation of an ingestible device comprising at least one impedance probe, in accordance with still another preferred embodiment of the present invention.
Figure 9B:
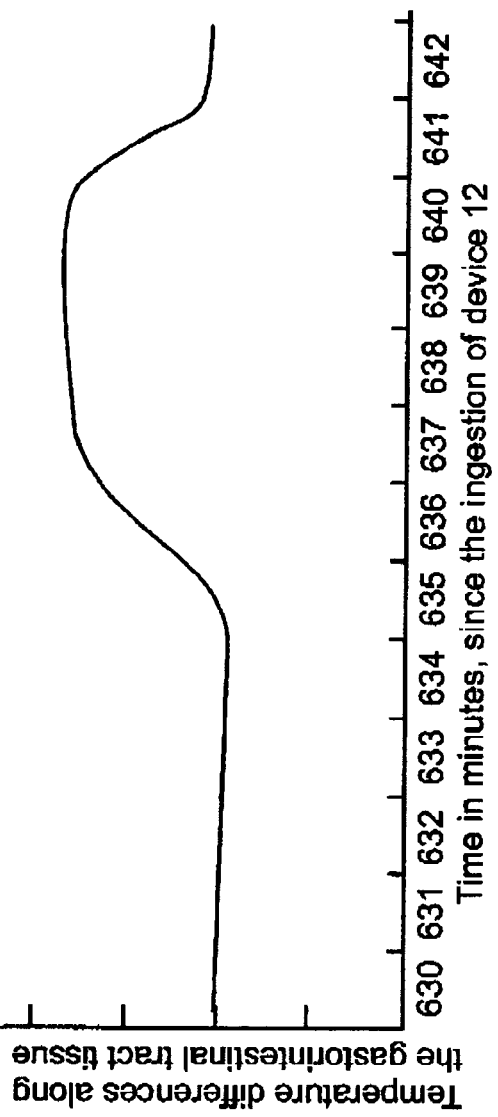

Referring further to the drawings, FIGS. 9A and 9B schematically illustrate ingestible device 12, arranged for imaging impedance of the gastrointestinal-tract tissue, and a method of imaging thereof, using at least one impedance probe $110_A$, in accordance with a preferred embodiment of the present invention. Impedance imaging has been found useful in detecting tumors and other pathologies.

At least one impedance probe $110_A$ has tips $112_{A1}$ and $112_{A2}$ which preferably are butt with the external surface of shell 58, so as to form direct contact with tissue of gastrointestinal tract 14. Preferably, tips $112_{A1}$ and $112_{A2}$ are formed of a biocompatible metal, such as SS, titanium, titanium alloy, and the like, or of another biocompatible conductor. Impedance may thus be measured between tips $112_{A1}$ and $112_{A2}$. Preferably probe 50 includes additional impedance probes, such as $110_B$, having tips $112_{B1}$ and $112_{B2}$, and $110_C$, having tips $112_{C1}$ and $112_{C2}$.

Ingestible device 12 may further include transmitter 54, power source 52 and related circuitry 56, as has been described hereinabove, in conjunction with FIG. 2A.

In the small intestine, direct contact between ingestible device 12 and the walls of gastrointestinal tract 14 is likely to occur. As ingestible device 12 travels within gastrointestinal tract 14, particularly in the small intestine, differences in tissue impedance are detected, as tips $112_{A1}$ and $112_{A2}$, $112_{B1}$ and $112_{B2}$, and $112_{C1}$ and $112_{C2}$ form contact with tissue of gastrointestinal tract 14. At pathological site, a change in impedance is likely to be observed.

A diagnostic image of tissue impedance may comprise diagnostic information as a function of time, in the manner seen in FIG. 9B, or diagnostic information as a function of distance traveled by ingestible device 12, based on the information seen in FIG. 3D.

Figure 10A:
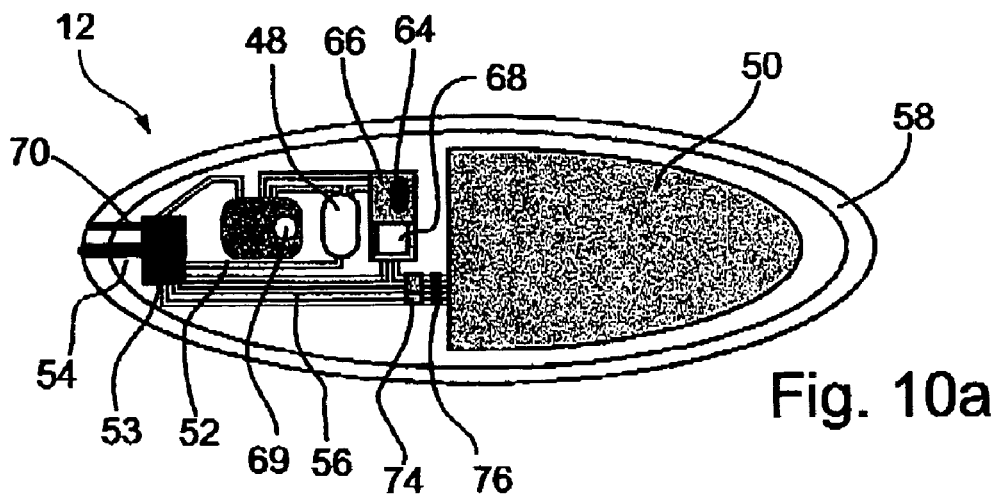
FIGS. 10A and 10B schematically illustrate ingestible devices, in accordance with still other preferred embodiments of the present invention.
Figure 10B:
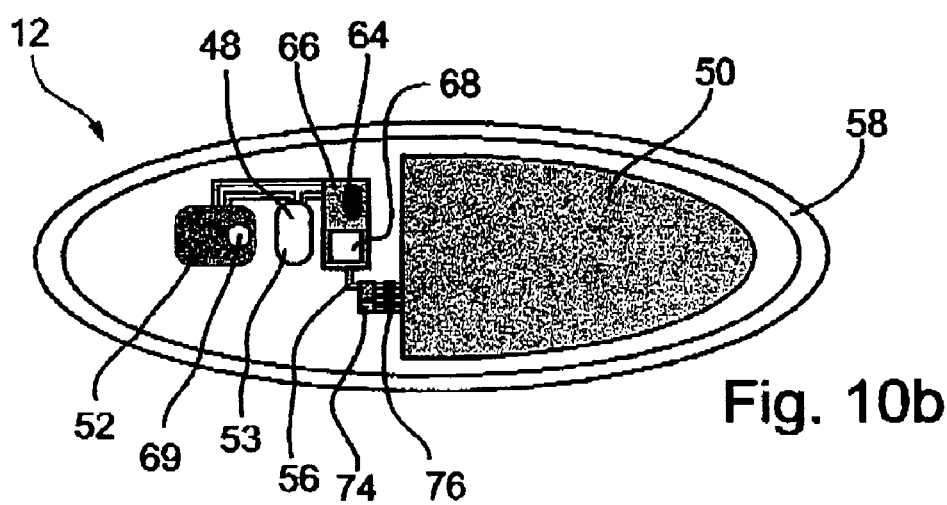

Referring further to the drawings, FIGS. 10A and 10B schematically illustrate additional components of ingestible device 12, in accordance with other preferred embodiments of the present invention. Ingestible device 12 may further include any one of the following components:

i. a tracking system 48;
ii. computer means 64, which may include a processor 66, and preferably also a memory 68, for example, in a form of a microcomputer 64;
iii. a receiver 70, for receiving instructions from computer means 30 or from computer system 20, as will be described hereinbelow;
iv. a transducer 69, in power communication with power source 52, for extracorporeally energizing power source 52;
v. circuitry and components 74 dedicated to signal amplification and (or) preamplification, as known; and vi. circuitry and components 76, dedicated to reducing signal to noise ratio, as known.

In accordance with the present invention, computer means 64 is another component of data-handling apparatus 53, arranged for receiving and handling imaging data generated by probe 50. Computer means 64 may be used in tandem with computer means 30 of extracorporeal apparatus 18 (FIG. 1C), and (or) computer station 20 (FIG. 1B), via transmitter 54, and possibly also, receiver 70, shown in FIG. 10A.

Alternatively, computer means 64 may be used in tandem with computer means 30 of extracorporeal apparatus 18 (FIG. 1C), and (or) computer station 20 (FIG. 1B), via receiver 70 only.

Alternatively, computer means 64 may be used in place of computer means 30 of extracorporeal apparatus 18 (FIG. 1C) and in place of transmitter 54, making ingestible device 12 an autonomous unit, as shown in FIG. 10B. Accordingly, extracorporeal apparatus 18 need not be used. Preferably, where extracorporeal apparatus 18 is not used, data may be recorded by computer means 64, and retrieved with ingestible device 12 after the completion of the diagnostic route in gastrointestinal tract 14. Computer means 64 may record the data and perform calculations in manners analogous to that of computer means 30 (FIG. 1C), or computer station 20 (FIG. 1B), as described hereinabove, in conjunction with FIGS. 3A-9B. Memory 68 is preferably analogous to removable data storage implement 38 (FIG. 1C) and may be removed and read by data reading implement 44 of computer station 20 (FIG. 1B).

Power source 52 may be an energizable power source, which further includes transducer 69, for example, as taught by U.S. Pat. No. 6,277,078, to Porat, et al., entitled, "System and method for monitoring a parameter associated with the performance of a heart," whose disclosure is incorporated herein by reference. Preferably, transducer 69 is a piezoelectric transducer, which may be energized by extracorporeal ultrasound radiation, directed at it.

Receiver 70 may be arranged for RF communication, which may be multichanneled. Alternatively, receiver 70 may be an ultrasound receiver. Receiver 70 and transmitter 54 may be integrated to a single unit.

Communication between the components of ingestible device 12 may be wired or wireless.

Various types of tracking systems 48 may be used, in accordance with the present invention. These may be additional to, or in place of plurality of receivers 40 of extracorporeal apparatus 18 (FIG. 1C) and transmitter 54, as will be described hereinbelow, in conjunction with FIGS. 13A-19B.

Figure 11:
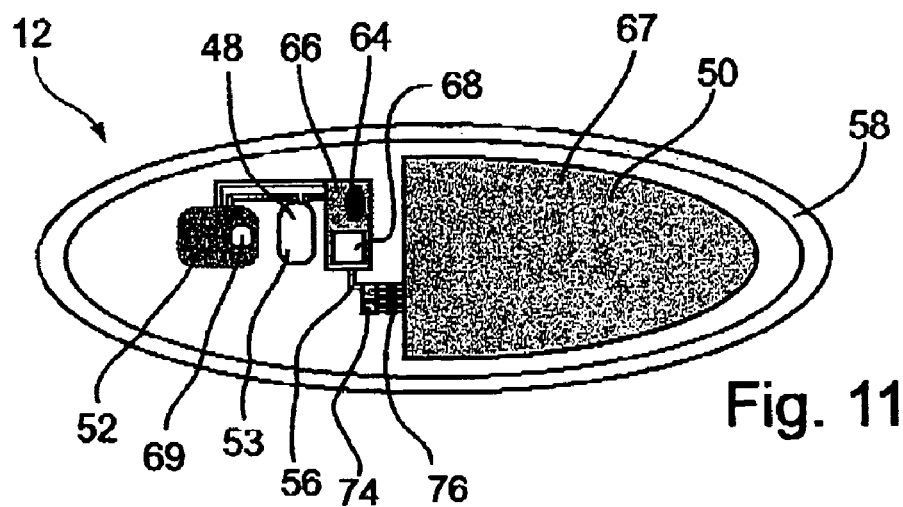
FIG. 11 schematically illustrates an ingestible device comprising an ultrasound probe, in accordance with yet another preferred embodiment of the present invention.

Referring further to the drawings, FIG. 11 schematically illustrates ingestible device 12, arranged for imaging ultrasound reflection of the gastrointestinal-tract tissue, in accordance with a preferred embodiment of the present invention. Accordingly, probe 50 comprises an ultrasound probe 67, formed, for example, as a transducer array, arranged for transmitting and receiving the ultrasonic radiation. Ingestible device 12 may further include computer means 64, and (or) transmitter 54 and possibly also receiver 70, and other components, as described hereinabove, in conjunction with FIGS. 10A and 10B.

Ultrasound probes similar to probe 67 of the present invention are taught by U.S. Pat. No. 5,088,500 to Wedel, et al., entitled, "Ultrasound finger probe and method for use," U.S. Pat. No. 5,284,147, to Hanoaka, et al., entitled, "Ultrasonic probe to be installed on fingertip," and U.S. Patent Application 20010020131, to Kawagishi, Tetsuya, et al., entitled, "Ultrasonic diagnosis system," whose disclosures are incorporated herein by reference.

Various contrast agents may be used with ultrasound probe 67, for example, as taught by U.S. Pat. No. 6,280,704, to Schutt, et al., entitled, "Ultrasonic imaging system utilizing a long-persistence contrast agent," whose disclosure is incorporated herein by reference.

A diagnostic image of ultrasound reflection may comprise diagnostic information as a function of time, in the manner analogous to that seen in FIG. 3A, or diagnostic information as a function of distance traveled by ingestible device 12, based on the information seen in FIG. 3D.

Figure 12A:
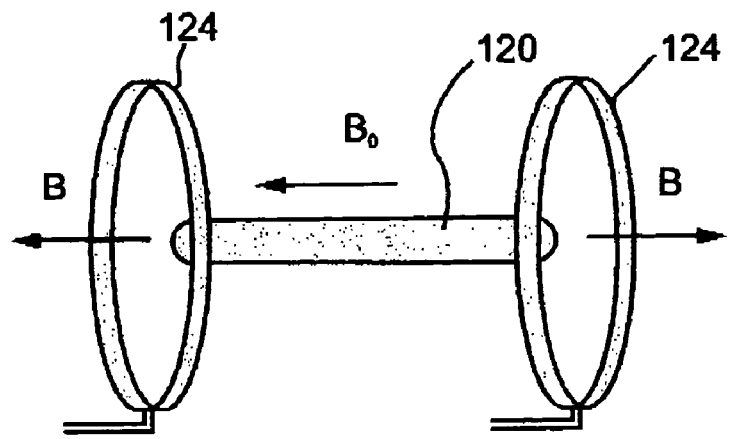
FIGS. 12A-12C schematically illustrate a probe arranged as an MRI probe, in accordance with yet another preferred embodiment of the present invention.
Figure 12B:
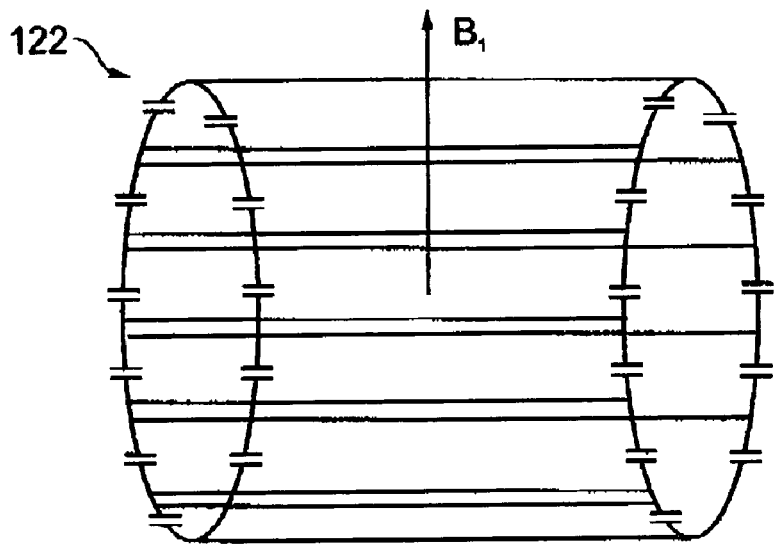
Figure 12C:
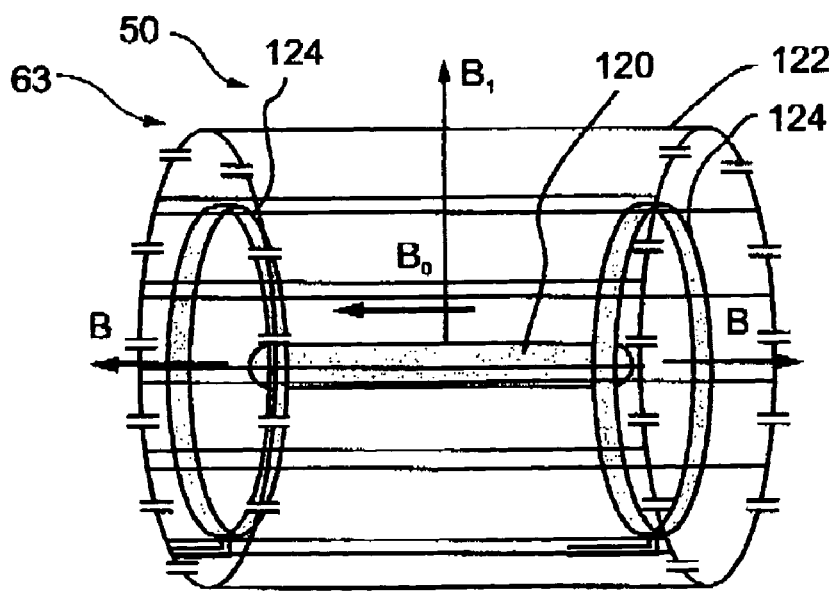

Referring further to the drawings, FIGS. 12A-12C schematically illustrate ingestible device 12, arranged for imaging magnetic resonance of the gastrointestinal-tract tissue, in accordance with a preferred embodiment of the present invention. Accordingly, probe 50 comprises an MRI probe 63.

MRI probe 63 comprises a miniature permanent magnet 120, preferably formed as a cylindrical rod. Permanent magnet 120 defines a longitudinal axis z, and has magnetic field $B_0$ in the z direction. Additionally, MRI probe 63 comprises an RF coil 122, preferably surrounding permanent magnet 120. RF coil 122 may be formed as a bird cage RF coil. Alternatively, RF coil may be formed as a multiple-turn RF coil, the multiple turns surrounding permanent magnet 120. Alternatively, another known RF coil may be used.

In accordance with a preferred embodiment of the present invention, no gradient coils are used; positional information may be acquired, as has been described hereinbelow, in conjunction with FIGS. 3A-3D, or as described hereinabove, in conjunction with FIGS. 13A-17B.

Thus, a diagnostic image of MRI may comprise diagnostic information as a function of time, in the manner analogous to that seen in FIG. 3A, or diagnostic information as a function of distance traveled by ingestible device 12, based on the information seen in FIG. 3D.

In accordance with another preferred embodiment of the present invention, gradient coils 124, formed for example, as antihelmholtz type of coils may be used.

The operation of MRI Probe 63 may be controlled by computer station 20, or by computer means 30, in a wireless manner, via receiver 70. Alternatively, the operation of MRI probe 63 may be controlled by computer means 64.

In accordance with a preferred embodiment of the present invention, for use with MRI probe 63, transmitter 54 preferably comprises an ultrasound transmitter, and receiver 70 preferably comprises an ultrasound receiver, wherein the transmitter and receiver may be incorporated into a single ultrasound transducer. Thus, interference from extraneous RF signals is minimized.

Various contrast agents may be used with MRI probe 63, for example, as taught by U.S. Pat. No. 6,315,981 to Unger, entitled, "Gas filled microspheres as magnetic resonance imaging contrast agents," whose disclosure is incorporated herein by reference.

Figure 13A:
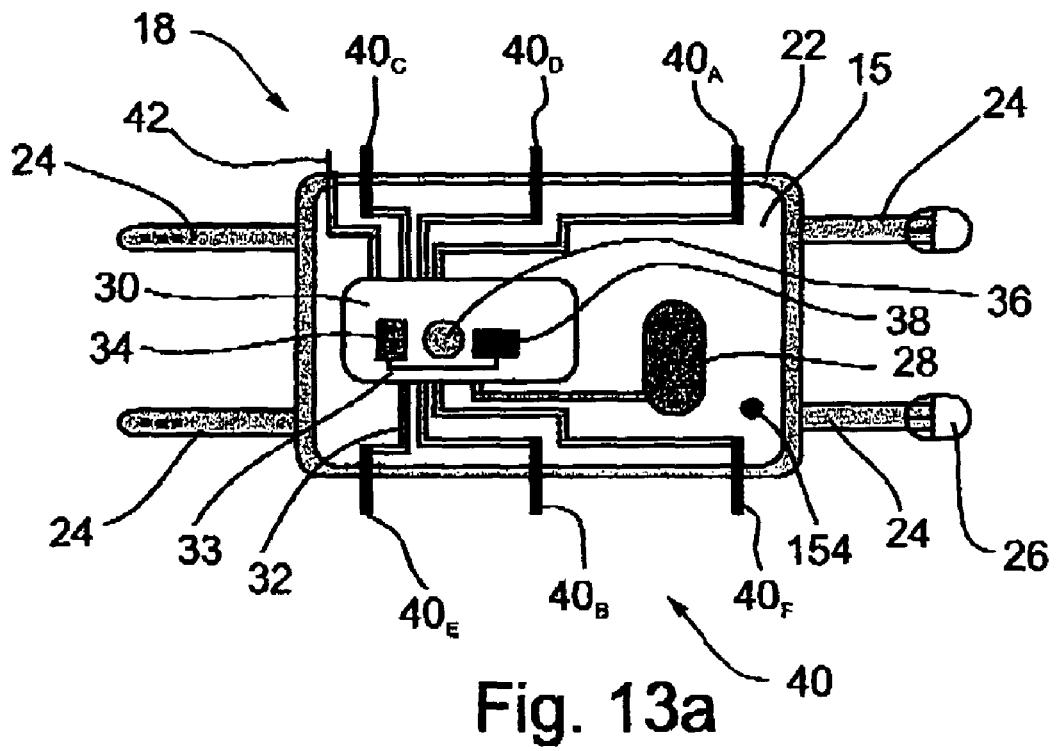
FIGS. 13A-13B schematically illustrate a tracking system, in accordance with a preferred embodiment of the present invention.
Figure 13B:
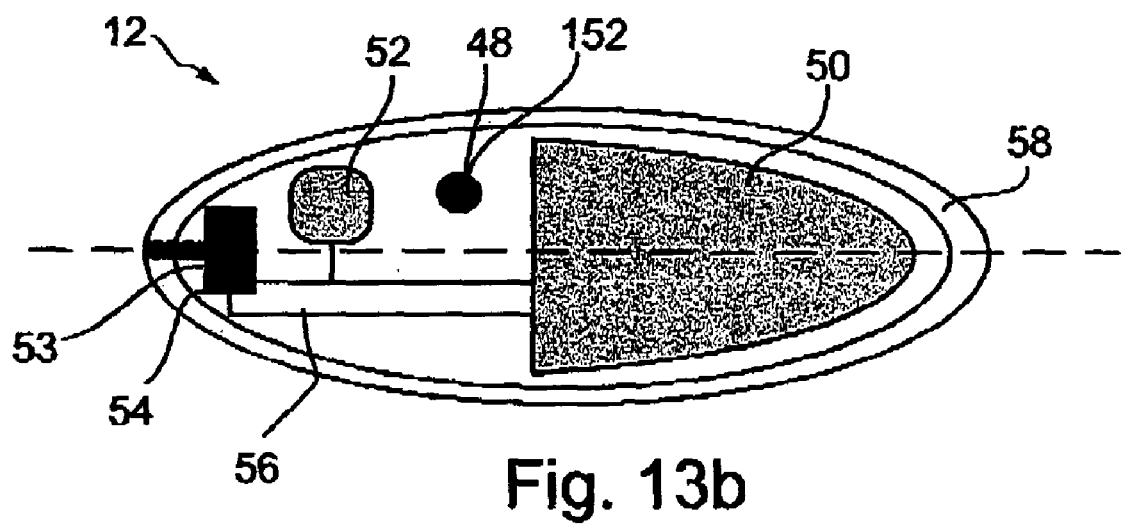

Referring further to the drawings, FIGS. 13A-13B schematically illustrate tracking system 48, using at least one acceleration sensor 152, in accordance with a preferred embodiment of the present invention.

As seen in FIG. 13A, tracking system 48 may comprise at least one acceleration sensor 152, which senses accelerations in at least three degrees of freedom, such as with respect to a set of three mutually perpendicular coordinate axes. Alternatively, tracking system 48 may comprise at least three acceleration sensors 152, each sensing accelerations along a single axis of a set of three mutually perpendicular coordinate axes. The acceleration sensors may comprise one or more miniature or micro-accelerometers. Computer means 64 or computer means 30 may estimate distance L (FIG. 3A) traveled by gastrointestinal diagnostic device 12, within gastrointestinal tract 14, as a function of an accelerations sensed by the acceleration sensors.

As seen in FIG. 13B, extracorporeal apparatus 18 may further include at least one extracorporeal acceleration sensor 154 which senses accelerations in at least three degrees of freedom, or at least three acceleration sensors, each sensing accelerations in a single degree of freedom, of the set of three mutually perpendicular coordinate axes. In this way, correction for the motion of body 16 (FIG. 1A) may be made.

Acceleration sensors 152 and 154 may be used in place of plurality of antennae 40, or in addition to them.

Figure 14A:
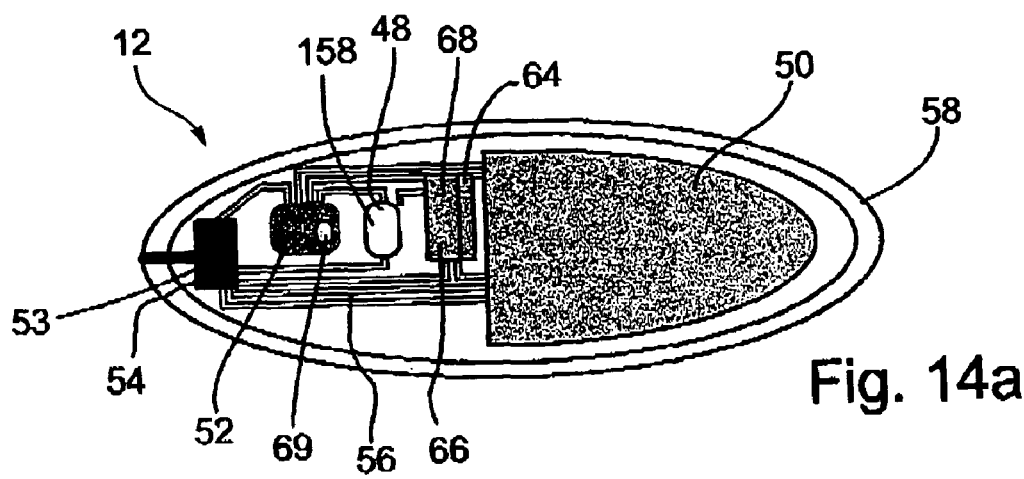
FIGS. 14A-14C schematically illustrate a tracking system, in accordance with another preferred embodiment of the present invention.
Figure 14B:
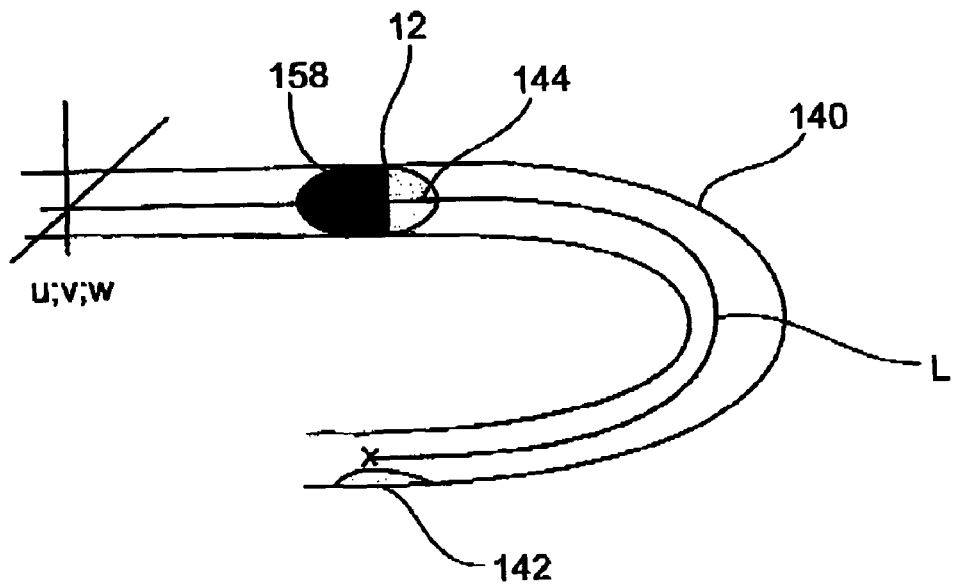
Figure 14C:
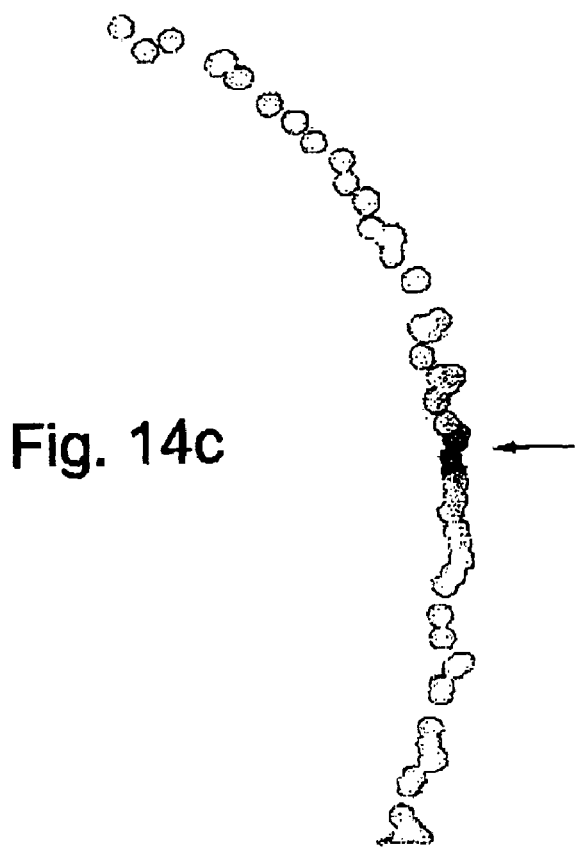

Referring further to the drawings, FIGS. 14A-14C schematically illustrate tracking system 48, by magnetic tracking and location, in accordance with another preferred embodiment of the present invention. Tracking system 48 may comprise a system 158 known as miniBird™, which is a magnetic tracking and location system commercially available from Ascension Technology Corporation, P.O. Box 527, Burlington, Vt. 05402 USA. The miniBird™ 158 measures the real-time position and orientation (six degrees of freedom) of one or more miniaturized sensors, so as to accurately track the spatial location of probes, instruments, and other devices. Thus, distance L (FIG. 3A) may be estimated. The dimensions of miniBird™ 158 are 18 mm×8 mm×8 mm for Model 800 and 10 mm×5 mm×5 mm the Model 500, small enough for use with ingestible device 12.

Experimental results of the operation of miniBird™ 158 are seen in FIGS. 14B and 14C. A flexible U-shaped plastic tube 140, of 120 cm in length and 6 cm in diameter, was fixed to a flat surface (not shown) and served as a model for the human colon. A single radiation source constituting a point source 142 of 100 µCi of $^{57}$Co was attached to the outer surface of the tube. Ingestible device 12, was simulated by radiation detector 144 comprising a 125 mm$^3$ CdZnTe crystal, obtained from eV Products, PA, USA) 375 Saxonburg Blvd. Saxonburg, Pa. 16056, used without a collimator.

Attached to radiation detector 144 was miniBird 158, forming a model of ingestible device 12. The count readings were filtered using an energy window of +/−6% around the 122 KeV energy peak. Radiation detector 144 and miniBird 158 were tied to a string (not shown) and pulled by hand, a distance L' through the lumen of tube 140, past radiation source 142. The integrated count readings and location information were relayed to a personal computer for processing and visual presentation. The end result was a color-coded map, shown in black-and-white in FIG. 14C, which was proportional to the radiation count readings detected along the tube. FIG. 14C shows a gradual increase in radiation and a gradual decline with peak radiation corresponding to the true location of the source.

The result confirms that ingestible device 12, equipped with a radiation detector and location system and software may correctly identify a radiolabeled tissue within the gastrointestinal tract.

Figure 15:
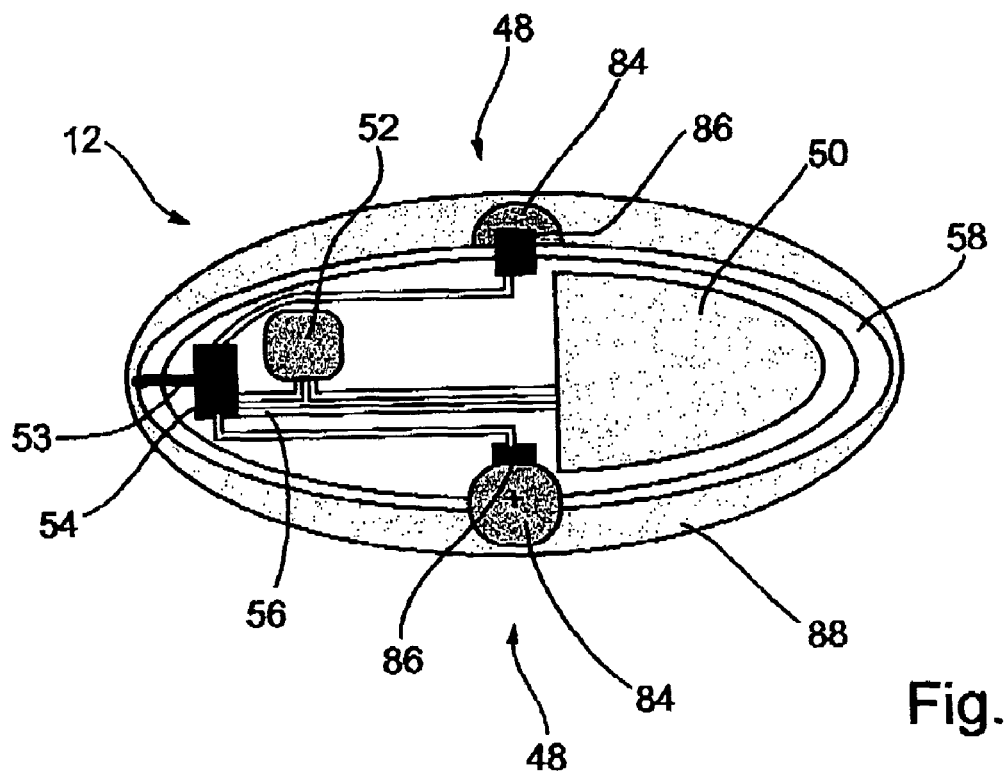
FIG. 15 schematically illustrates a tracking system, in accordance with a another preferred embodiment of the present invention.

Referring further to the drawings, FIG. 15 schematically illustrates a tracking system 48, which includes at least one miniature roller 84, in accordance with yet another embodiment of the present invention. Accordingly, ingestible device 12 further includes at least one miniature roller 84, external to shell 58. Roller 84 is in communication with a counter 86, which is internal to shell 58 and which counts complete revolutions performed by roller 84 and converts the count to signals, which are relayed to transmitter 54 and transmitted to extracorporeal computer means 30. Roller 84 measures distance traveled by ingestible device 12 in a manner similar to that by which tires measure the distance traveled by a car. In some embodiments, two or more rollers 84 may be used.

Preferably, ingestible device 12 with at least one roller 84 are enclosed within a cast 88 of gelatin, sugar or another substance that dissolves easily, to facilitate swallowing. In stomach 11 (FIG. 1A) cast 88 dissolves, uncovering at least one roller 84, which may then track the distance traveled in gastrointestinal tract 14, from intracorporeal reference system u; v; w, at the exit of stomach 11. The distance traveled by ingestible device 12, may be presented as a function of time, in a manner analogous to that of FIG. 3D.

Figure 16A:
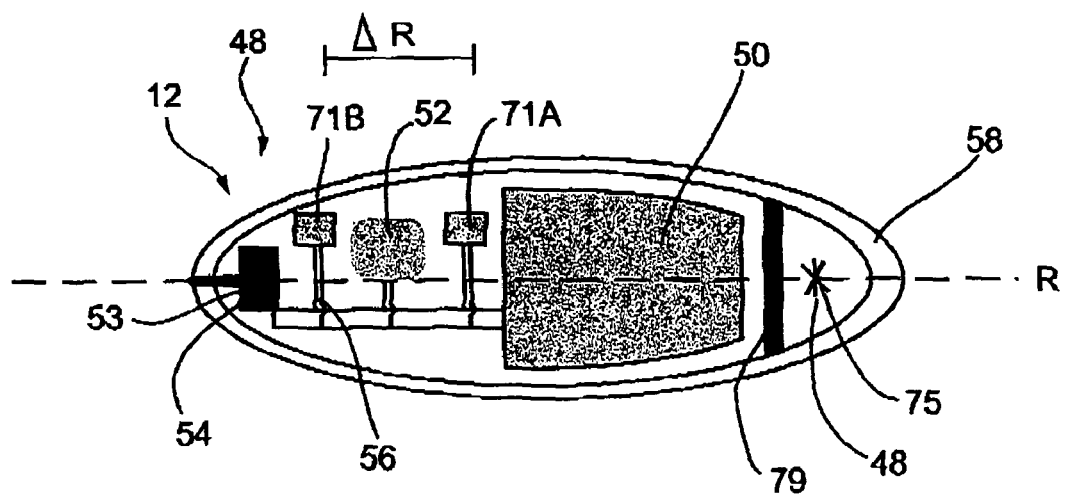
FIGS. 16A-16B schematically illustrate a tracking system, in accordance with still another preferred embodiment of the present invention.
Figure 16B:
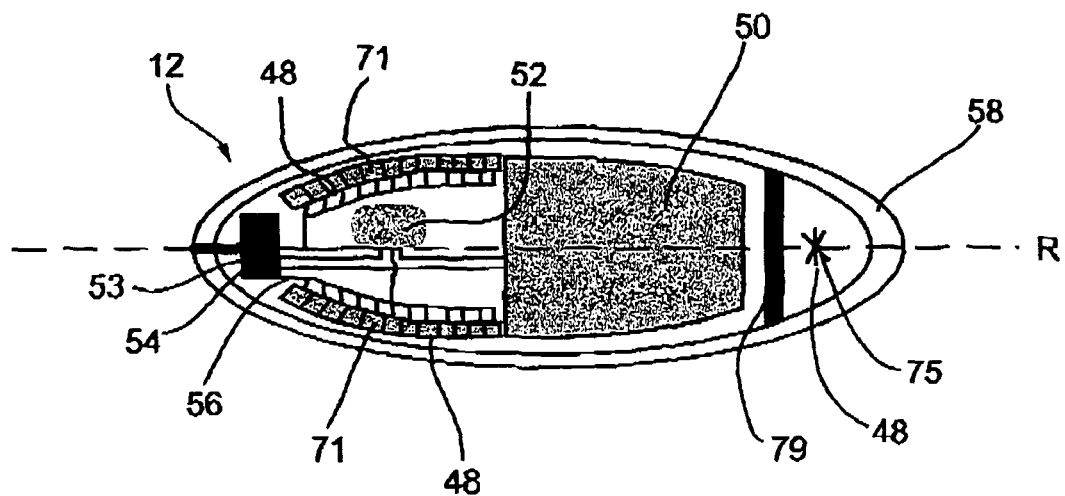

Referring further to the drawings, FIGS. 16A-16B schematically illustrate tracking system 48, which is based on cross correlation of reflected light, in accordance with still another preferred embodiment of the present invention.

Cross correlation of reflected light is a technique of movement tracking, used by Logitec iFeel™ MouseMan.

As seen in FIG. 16A, tracking system 48 comprises a light source 75, for example, a light-emitting diode 75, and at least two photo-sensing diodes, $71_A$ and $71_B$, arranged a distance Δ
□ □□□□□ □□□□□ □□□□□□□□□
Preferably, a light barrier 79 separates light-emitting diode 75 and photo-sensing diodes, $71_A$ and $71_B$.

Light, emitted from diode 75, is reflected by the walls of gastrointestinal tract 14 and detected by the at least two photo-sensing diodes, $71_A$ and $71_B$. By cross correlating detected signals at a first time T and at a later time T+ΔT, the incremental distance traveled by ingestible device 12, within gastrointestinal tract 14, during period ΔT may be evaluated. Distance L (FIG. 3A), traveled by ingestible device 12, may thus be evaluated by summing the incremental distances. Preferably, period ΔT is of the order of several seconds.

Alternatively, as seen in FIG. 16B, a photodetector 71, comprising a plurality of photo-sensing diodes, may be used, arranged with various distances between them along the R axis, to enhance the cross correlation.

In embodiments where light source 78 (FIG. 6) is used, as described hereinabove, light source 78 may be used in place of diode 75.

Additionally, photo-sensing diodes, $71_A$ and $71_B$ may be arranged to sense reflected light, emitted by light source 75 or 78, or optical fluorescence.

In accordance with the present invention, other forms of cross correlation may be used, for example, by ultrasound reflection, nuclear radiation, infrared radiation, scintillation produced by a scintillation liquid, impedance measurements, and the like.

Figure 17:
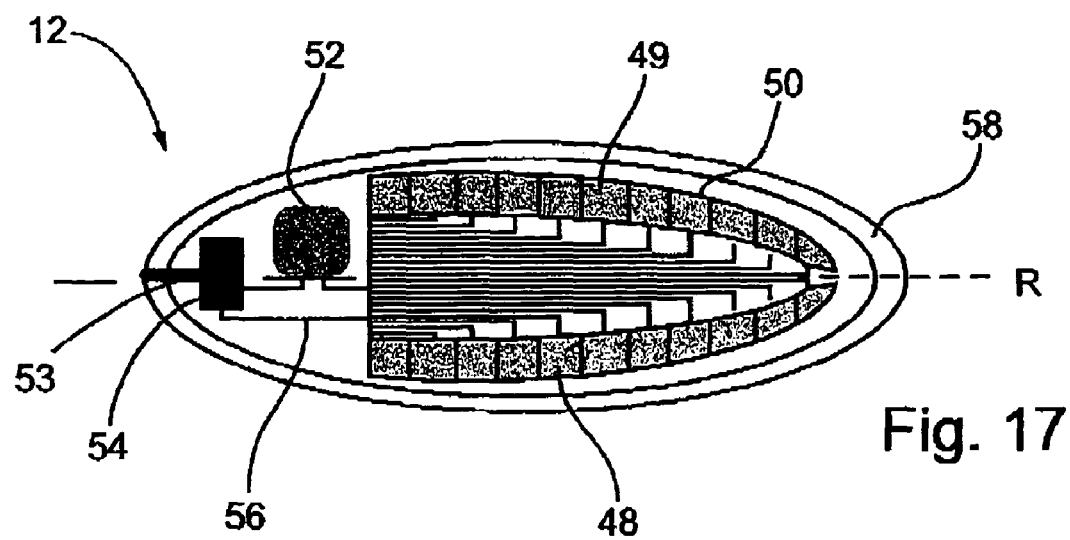
FIG. 17 schematically illustrates a tracking system, in accordance with yet another preferred embodiment of the present invention.

Referring further to the drawings, FIG. 17 schematically illustrates tracking system 48, wherein cross correlation is based on background-level nuclear radiation, in accordance with still another preferred embodiment of the present invention. Accordingly, nuclear-detector 49 includes at least two, and preferably a plurality of crystals, arranged with various distances between them along the R axis. By cross correlating background radiation levels at a first time T and at a later time T+ΔT, the incremental distance traveled by ingestible device 12 during period ΔT may be evaluated.

Figure 18:
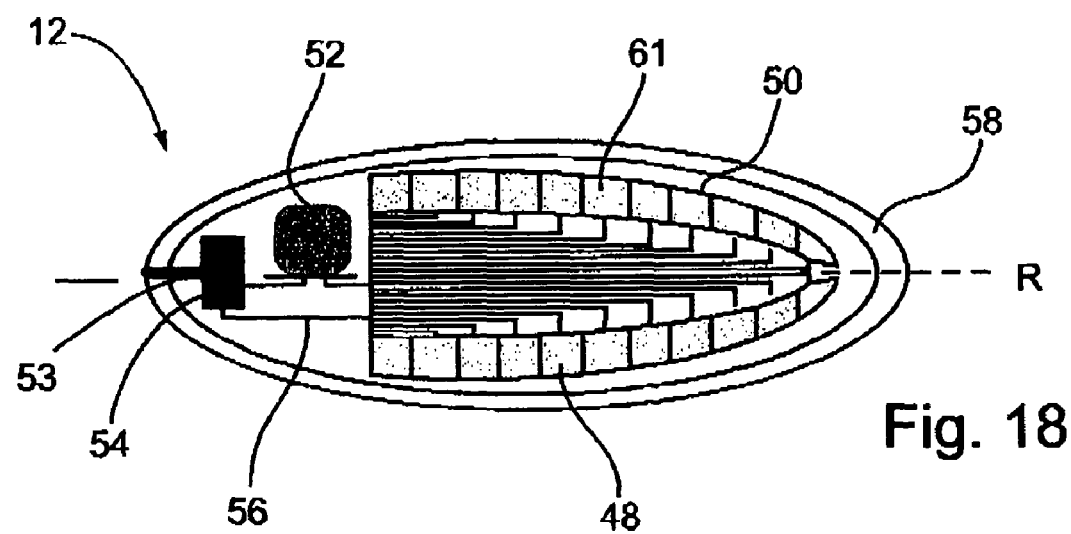
FIG. 18 schematically illustrates a tracking system, in accordance with still another preferred embodiment of the present invention.

Referring further to the drawings, FIG. 18 schematically illustrates tracking system 48, wherein cross correlation is based on infrared radiation, in accordance with yet another preferred embodiment of the present invention. Thus, thermography detector 61 may comprise at least two, and preferably a plurality of photo-sensing diodes, arranged with various distances between them along the R axis. By cross correlating infrared radiation levels at a first time T and at a later time T+ΔT, the incremental distance traveled by ingestible device 12 during period ΔT may be evaluated.

Similarly, tracking in the small intestine may be performed by cross correlation of impedance, using an impedance probe, which is preferably a multi-element impedance probe, with the multi-elements arranged with various distances between them, along the R axis, in accordance with still another preferred embodiment of the present invention.

Additionally, tracking in the small intestine may be performed by cross correlation of temperature differences, using a thermocouple probe, which is preferably a multi-element thermocouple probe, with the multi-elements arranged with various distances between them, along the R axis, in accordance with yet another preferred embodiment of the present invention.

Figure 19A:
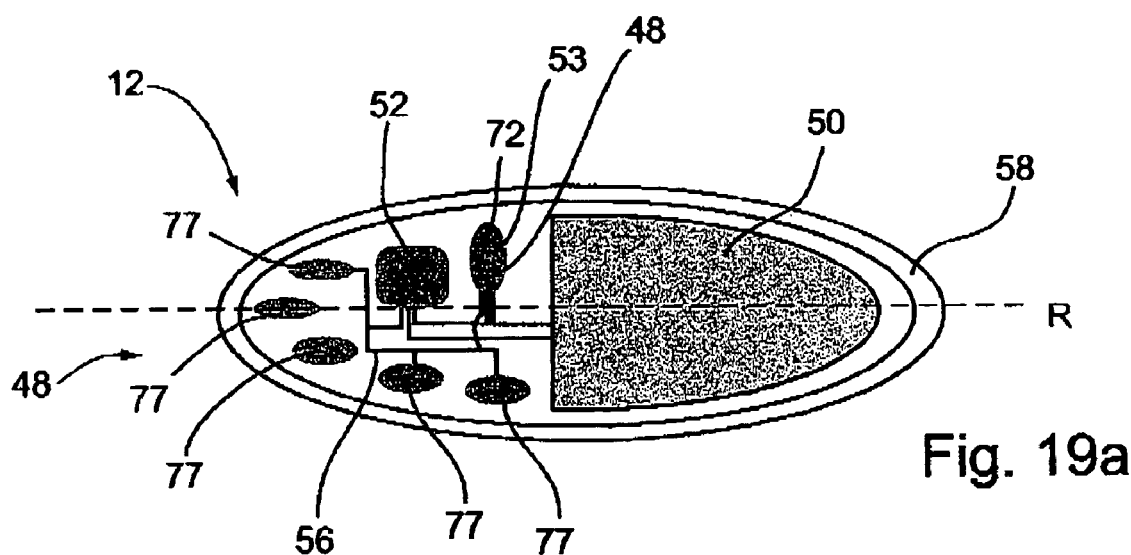
FIGS. 19A-19B schematically illustrate a tracking system, in accordance with yet another preferred embodiment of the present invention.
Figure 19B:
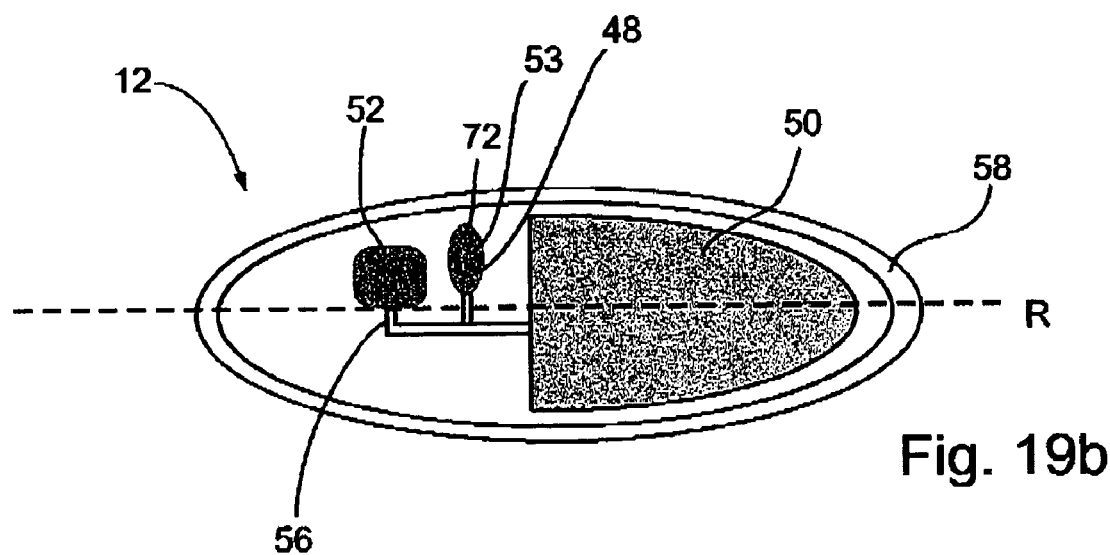

Referring further to the drawings, FIGS. 19A and 19B schematically illustrates tracking system 48, using ultrasound radiation, in accordance with still other preferred embodiments of the present invention. Tracking system 48 comprises a piezoelectric transducer 72, operable in the frequency range of about 40 KHz to about 20 MHz, at a power of few milliwatts.

Piezoelectric transducer 72 is operable by several methods, for tracking ingestible device 12, as follows:

1. Tracking may be performed by cross correlation of ultrasound radiation. As seen in FIG. 19A, a signal sent by transducer 72 will be reflected off the walls of gastrointestinal tract 14, and received again by transducer 72 and at least one additional transducer 77, of similar characteristics. Transducers 77 and 72 are arranged at a predetermined distance between them, along the R axis. By cross correlating signals from transducer 72 at a first time T and at a later time T+$\Delta$T, the incremental distance traveled by ingestible device 12 during period $\Delta$T may be evaluated. Additionally, a plurality of transducers 77 may be used, arranged with various distances between them, along the R axis.

2. Transducer 72 may operate in tandem with at least three extracorporeal receivers $40_A$, $40_B$ and $40_C$ (FIG. 1C), formed as piezoelectric transducers and arranged in direct contact with body 16, at different locations. For example, extracorporeal transducers $40_A$, $40_B$ and $40_C$ may be patch-sensor devices, described in U.S. Pat. Nos. 5,807,268; 5,913,829 and 5,885,222, all of which are assigned to MedAcoustics, Inc., Raleigh, N.C., USA, the disclosures of which are incorporated herein by reference. A first signal, sent by transducer $40_A$ is received by transducer 72, then sent out again by transducer 72 and received by transducers $40_A$, $40_B$ and $40_C$. A second signal, sent by transducer $40_B$ is received by transducer 72, then sent out again by transducer 72 and received by transducers $40_A$, $40_B$ and $40_C$. A third signal, sent by transducer $40_C$ is received by transducer 72, then sent out again by transducer 72 and received by transducers $40_A$, $40_B$ and $40_C$. A signal is then sent out again by transducer $40_A$ and the process is repeated. The distance between transducers $40_A$ and 72 is calculated based on the time the signal traveled from transducer $40_A$ to transducer 72 and back to transducer $40_A$. In a similar manner, the distances between transducers $40_B$ and 72 and between transducers $40_C$ and 72 may be calculated. As a result, the instantaneous x; y; z location of ingestible device 12 may be obtained, and distance L (FIG. 3A) traveled by ingestible device 12, may be estimated, as described hereinbelow, in conjunction with FIGS. 3C and 3D. Additional extracorporeal transducers, such as $40_D$, $40_E$, and $40_F$, may further be used.

3. Alternatively, or additionally, signals sent by transducer 72 may be received by at least three extracorporeal transducers $40_A$, $40_B$ and $40_C$, and the distances from receivers 40 to transducer 72 may be estimated in accordance with the inverse square relationship, based on differences in amplitudes.

Transducer 72 may further be used as an ultrasound transmitter, in place of, or in addition to transmitter 54 (FIG. 2A). Furthermore, transducer 72 may be used as an ultrasound receiver, in place of, or in addition to receiver 70 (FIG. 10A). As such, transducer 72 comprises data-handling apparatus 53 and is arranged for receiving and handling imaging data generated by probe 50.

It is important to point out the difference in approach, between estimating distance L (FIG. 3A), as described hereinabove, in conjunction with FIGS. 3C-3D, 13A-13B, 14A-14C and 19B, and evaluating distance L, as described hereinabove, in conjunction with FIGS. 15, 16A, 16B, 17, 18, and 19A.

In FIGS. 3C-3D, 13A-13C, 14A-14C, and 19B, instantaneous x; y; z, values are obtained with respect to extracorporeal reference system x; y; z, using at least three extracorporeal receivers, or at least one acceleration sensor, or a magnetic tracking and location system. This approach is fraught with a small error due to movement of gastrointestinal tract 14, as part of the digestive process. Thus, a calculation of the distance traveled by ingestible device 12, for example, from the exit of stomach 11 to a pathological site, will, give only an estimated distance.

Yet, in FIGS. 15, 16A, 16B, 17, 18, and 19A, incremental distances are obtained vis a vis the walls of gastrointestinal tract 14, using a roller or cross correlation of a sensed parameter. This approach is free of any error due to movement of gastrointestinal tract 14. Thus, a calculation of the distance traveled by ingestible device 12 will give a more exact value, than that of the first approach.

The present invention further includes a gastrointestinal-tract diagnostic program, comprising a range of ingestible devices, suitable for general screening of a large population, on the one hand, and specific diagnoses of suspected pathologies, on the other.

For example, general screening for gastrointestinal-tract neoplasm may be addressed with ingestible device 12, comprising nuclear-radiation detector 49, ingested after the administration of an anti-CEA or anti-TAG-72 radiopharmaceutical, or a radiopharmaceutical containing both.

Specific diagnoses, for example, of inflammations, may be addressed with ingestible device 12, comprising nuclear-radiation detector 49, ingested after the administration of $Ga^{67}$ citrate which is used for the detection of chronic inflammation, or after the administration of $Tc^{99m}$-HMPAO leukocytes, which have high sensitivity and specificity for acute infections.

It will be appreciated that many other combinations of ingestible device 12 and a specific pharmaceutical may be employed.

In accordance with another preferred embodiment of the present invention, general screening for gastrointestinal-tract pathologies may be addressed without a pharmaceutical Additionally, general screening may be addressed by providing an inexpensive ingestible device, which need not be retrieved and may be disposed of naturally, by the body. It may be pointed out that for general screening, ingestible device 12 that need not be retrieved is advantageous, since invariably, retrieval is associated with psychological and physical uncasiness.

An example of a relatively inexpensive ingestible device 12, operative without a pharmaceutical, is provided by ingestible device 12 of FIG. 7, hereinabove, wherein infrared thermography detector 61 is used for temperature imaging. Additionally, an example is provided in FIG. 8A, hereinabove, wherein at least one thermocouple probe $106_A$ is used, for temperature-difference imaging, particularly of the small intestine. Additionally, an example is provided in FIG. 9A, hereinabove, wherein at least one impedance probe $110_A$ is used, for impedance imaging, particularly of the small intestine. These may be used alone, or in combination. Since these are used without pharmaceuticals, there are little side effects associated with them.

Figure 20:
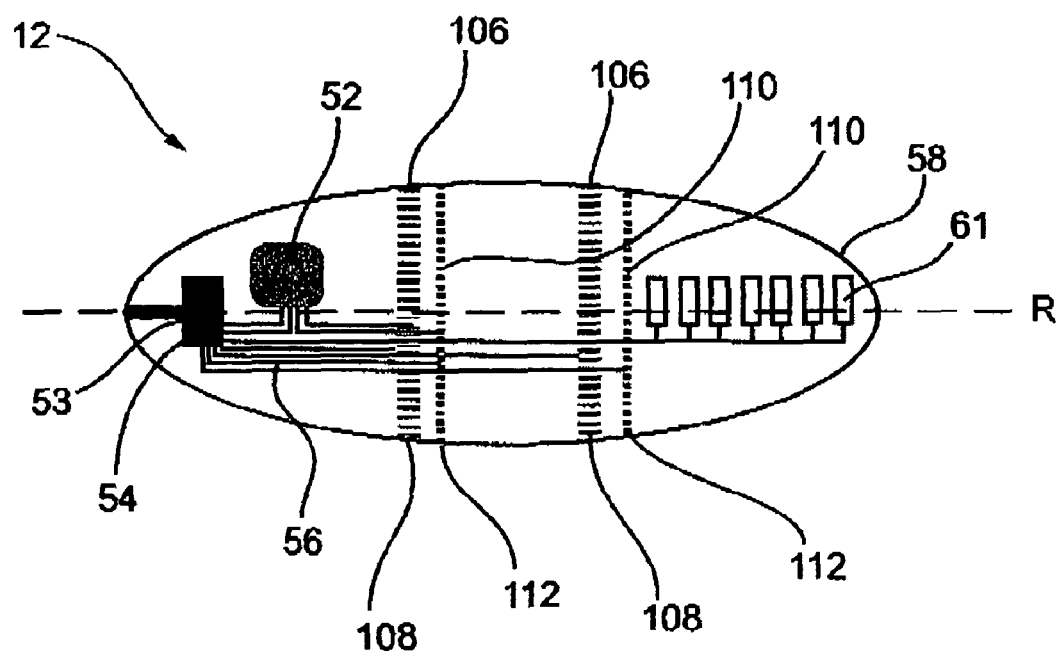
FIG. 20 schematically illustrates an ingestible device, arranged for general screening, in accordance with a preferred embodiment of the present invention.

Referring further to the drawings, FIG. 20 schematically illustrates a preferably disposable general-screening ingestible device 12, in accordance with a preferred embodiment of the present invention. Preferably, ingestible device 12 includes infrared thermography detector 61, for temperature imaging without contact Furthermore, infrared thermography detector 61 preferably includes a plurality of photo-sensing diodes, arranged, for example, along the R axis, for tracking ingestible device 12 by cross correlation of infrared radiation.

Additionally, general-screening ingestible device 12 may include a multi-element thermocouple probe 106, having a plurality of tips $108_1$ and $108_2$, arranged, for example, as two or more rings around the circumference of ingestible device 12. Furthermore, general-screening ingestible device 12 may include a multi-element impedance probe 110, having a plurality of tips $112_1$, and $112_2$, $108_2$, arranged, for example, as two or more rings around the circumference of ingestible device 12.

While multi-element thermocouple probe 106 and impedance probe 110 are suitable for diagnosis of the small intestine, infrared thermography detector 61 is arranged to produce a temperature image of entire gastrointestinal tract 14.

Preferably, ingestible device 12 further includes power source 52, transmitter 54 or transducer 72 (FIG. 19B) and related circuitry 56.

In accordance with the present invention, general screening ingestible device 12 may be administered as a first stage. Where pathologies are suspected, imaging may be repeated with ingestible device 12 arranged for other forms of diagnosis, preferably with specific pharmaceuticals.

Additionally, ingestible device 12, arranged for other forms of diagnosis may further include the probes of general screening ingestible device 12, in order to correlate early findings with those of later stages.

In accordance with the present invention, ingestible device 12 may comprise a single probe 50, or two or more different probes 50, for producing simultaneous imaging by different techniques.

In accordance with the present invention, ingestible device 12 may comprise probe 50 and a second probe, formed as a video camera, for example, a video camera as taught by U.S. Pat. No. 5,604,531, to Iddan, et al., entitled, "In vivo video camera system," and U.S. Patent Application 20010035902, to Iddan, G. J., et al. entitled, "Device and system for in vivo imaging," whose disclosures are incorporated herein by reference.

In accordance with the present invention, the choice of a radiopharmaceutical for the detection of neoplastic tissue, may include any one of the following
1. CEA-Scan is a $Tc^{99m}$-labeled monoclonal antibody fragment, which targets CEA, or an anti-CEA monoclonal antibody labeled by another radioisotope, for example, $I^{131}$. (Jessup J M. 1998, Tumor markers—prognostic and therapeutic implications for colorectal carcinoma, Surgical Oncology; 7: 139-151.)
2. $In^{99m}$-Satumomab Pendetide (Oncoscint®), as an anti TAG-72. (Molinolo A; Simpson J F; et al. 1990, Enhanced tumor binding using immunohistochemical analyses by second generation anti-tumor-associated glycoprotein 72 monoclonal antibodies versus monoclonal antibody B72.3 in human tissue, Cancer Res. 50(4): 1291-8.)
3. Anti-Lipid-Associated Sialic Acid (LASA). (Ebril K M, Jones J D, Klee G G. 1985, Use and limitations of serum total and lipid-bound sialic acid concentrations as markers for Colorectal cancer, Cancer; 55:404-409.)
4. Anti-Matrix Metaloproteinase-7 (MMP-7). (Mori M, Barnard G F et al. 1995, Overexpression of matrix metalloproteinase-7 mRNA in human colon carcinoma. Cancer; 75: 1516-1519.)

Additionally, in accordance with the present invention, a radiopharmaceutical may be used a marker for nonmalignant pathologies, such as gastrointestinal inflammations and infections. Examples include the following:
1. $Ga^{67}$ citrate. (Mettler F A, and Guiberteau M J, Eds. 1998, Inflammation and infection imaging. Essentials of nuclear medicine. Fourth edition. Pgs: 387-403.)
2. Nonspecific-polyclonal immunoglobulin G (IgG). (Mettler F A, and Guiberteau M J, ibid.)
3. Radio-labeled leukocytes, such as such as $In^{111}$ oxine leukocytes and $Tc^{99m}$ HMPAO leukocytes. (Mettler F A, and Guiberteau M J, ibid; Corstens F H; van der Meer J W. 1999. Nuclear medicine's role in infection and inflammation. Lancet; 354 (9180): 765-70.)

The particular choice of a radionuclide for labeling the radiopharmaceutical is dependent upon its nuclear properties, the physical half-life, the detection instruments' capabilities, the pharmacokinetics of the radiolabeled antibody, and the degree of difficulty of the labeling procedure. The radionuclide may be, for example, any one of Technetium $Tc^{99m}$, Iodine $I^{125}$, $I^{123}$, $I^{131}$, and $I^{133}$, Indium $In^{111}$, Gallium $Ga^{67}$, thallium $Tl^{201}$, fluorine $F^{18}$ and $P^{32}$.

Figure 21:
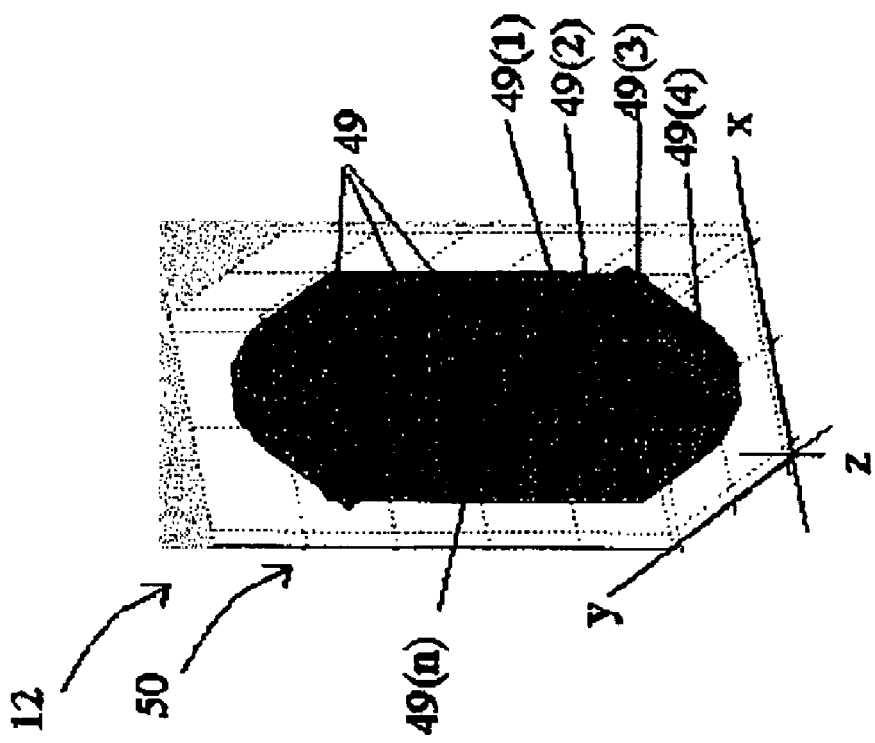
FIG. 21 schematically illustrates an ingestible device, in accordance with a preferred embodiment of the present invention.

Referring further to the drawings, FIG. 21 schematically illustrates ingestible device 12, in accordance with a preferred embodiment of the present invention. For the purpose of illustration, ingestible device 12 is shown in a coordinate system x; y; z. Preferably, probe 50 of ingestible device 12 includes a plurality of nuclear-radiation detectors 49, such as nuclear radiation detectors 49(1), 49(2), 49(3), 49(4), . . . 49(n), which preferably cover up the external surface of ingestible device 12. Preferably, each detector 49(n) is operative as a single pixel.

It will be appreciated that this design may also lend itself to a Compton camera, as some of detectors 49(n) are opposite each other. Thus, a few of detectors 49(n) may be dedicated for this purpose. The shape of ingestible device 12 may then change slightly, for example, include a narrow portion, similar for example, to a Coke bottle, to allow the compton camera detectors to be closer to each other.

Preferably, radiation detectors 49 are room temperature, solid-state detectors, preferably, CdZnTe, obtained, for example, from IMARAD IMAGING SYSTEMS LTD., of Rehovot, ISRAEL, 76124. Alternatively, other detectors as known may be used, for example, solid state detectors, such as CdTe, HgI, Si, Ge, and the like, and scintillation detectors, such as NaI(Tl), LSO, GSO, CsI, CaF, and the like.

Room temperature solid-state CdZnTe (CZT) is among the more promising nuclear detectors currently available. It has a better count-rate capability than other detectors on the market, and its pixilated structure provides intrinsic spatial resolution. Furthermore, because of the direct conversion of the gamma photon to charge-carriers, energy resolution is enhanced and there is better rejection of scatter events and improved contrast.

In accordance with the present invention, the detector may be optimized, in accordance with the teaching of "Electron lifetime determination in semiconductor gamma detector arrays," "GdTe and CdZnTe Crystal Growth and Production of Gamma Radiation Detectors," and "Driving Energy Resolution to the Noise Limit in Semiconductor Gamma Detector Arrays," Poster presented at NSS2000 Conference, Lyon France, Oct. 15-20, 2000, all by Uri Lachish, of Guma Science, P.O. Box 2104, Rehovot 76120, Israel, all of whose disclosures are incorporated herein b) reference.

Accordingly, each radiation detector $49(n)$ may be a monolithic CdZnTe crystal, doped with a trivalent donor, such as indium. Alternatively, aluminum may be used as the trivalent donor. When a trivalent dopant, such as indium, replaces a bivalent cadmium atom within the crystal lattice, the extra electron falls into a deep trap, leaving behind an ionized shallow donor. The addition of more donors shifts the Fermi level from below the trapping band to somewhere within it. An optimal donor concentration is achieved when nearly all the deep traps become occupied and the Fermi level shifts to just above the deep trapping band.

Optimal spectral resolution may be achieved by adjusting the gamma charge collection time (i.e., the shape time) with respect to the electron transition time from contact to contact. Gamma photons are absorbed at different depth within the detector where they generate the electrons. As a result, these electrons travel a different distance to the counter electrode and therefore produce a different external signal for each gamma absorption event. By making the shape time shorter than the electron transition time, from contact to contact, these external signals become more or less equal leading to a dramatic improvement in resolution.

Furthermore, for a multi-pixel detector, the electrons move from the point of photon absorption towards the positive contact of a specific pixel. The holes, which are far slower, move towards the negative contact, and their signal contribution is distributed over a number of pixels. By adjusting the gamma charge collection time (i.e., the shape time) with respect to the electron transition time from contact to contact, the detector circuit collects only the electrons' contribution to the signal, and the spectral response is not deteriorated by the charge of the holes.

For an optimal detector, crystal electrical resistively may be, for example, about $5 \times 10^8$ ohm cm. The bias voltage may be, for example, $-200$ volts. The shape time may be, for example, $0.5 \times 10^{-6}$ sec. It will be appreciated that other values, which may be larger or smaller are also possible.

Figure 22:
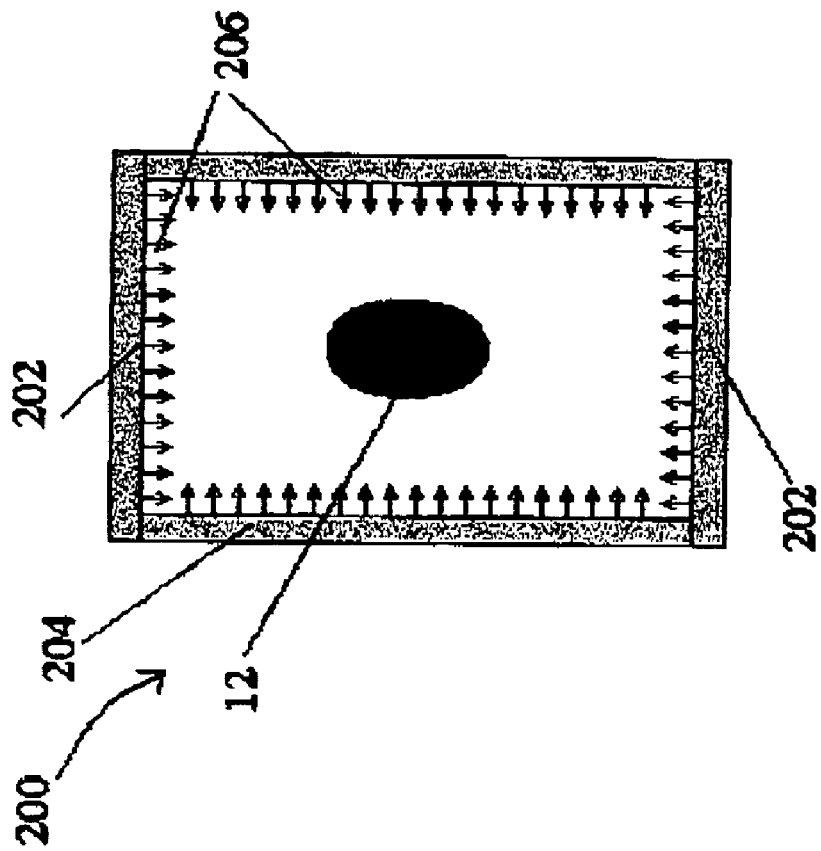
FIG. 22 schematically illustrates a device for detector calibration, in accordance with a preferred embodiment of the present invention.

Referring further to the drawings, FIG. 22 schematically illustrates a device for detector $49(n)$ calibration in accordance with a preferred embodiment of the present invention. Non-uniformity of the material leads to different sensitivities for each pixel $49(n)$, of probe 50. A correction is required to eliminate the sensitivity effect of the different pixels.

The calibration procedure includes placing ingestible device 12 in a cylindrical source 200, enclosed by cylindrical source walls 204 and top and bottom plate sources 202, and maintaining a substantially even flux 206. Preferably the radiation that is used is low gamma radiation, for example, 24 KeV.

Referring further to the drawings, FIG. 23 schematically illustrates a method for detector calibration, in accordance with a preferred embodiment of the present invention. For each detector $49(n)$, the location of the energy peak, corresponding to the peak photon energy, for example, 24 KeV, is bounded, by an upper level (UL) and a lower level (LL) for that detector, forming an energy window for the specific detector $49(n)$. Only photons which fall within the bounded energy window are counted, to exclude Compton scattering and pair production. A multi-energy source may be used, and several energy windows may be bounded for each detector $49(n)$.

After the energy windows, representing specific energy peaks, are determined for each detector $49(n)$, they are stored in a memory unit.

To correct for the different sensitivities of each detector, due to non-uniformity of the material, each detector $49(n)$ is assigned a sensitivity correction factor f(n). To obtain f(n), the total counts of ingestible device 12 in a given period is divided by the number of detectors, or pixels $49(n)$, thus obtaining an average count per pixel. That average, divided by the actual counts of a particular detector, yields the correction factor f(n). For example, $$f(1) = \frac{\text{average count per pixel}}{\text{actual counts in } 49(1)}$$

During acquisition, the sum of counts within the bounded windows of each detector $49(n)$ is multiplied by the the correction factor f(n) to obtain a sensitivity corrected count rate.

It will be appreciated that image reconstruction analysis may include various deconvolution algorithms, as known, for example, as taught in commonly owned, concurrently filed, co-pending application, "Radioactive Emission detector Equipped with a Position Tracking System," whose disclosure is incorporated herein by reference.

Figure 24:
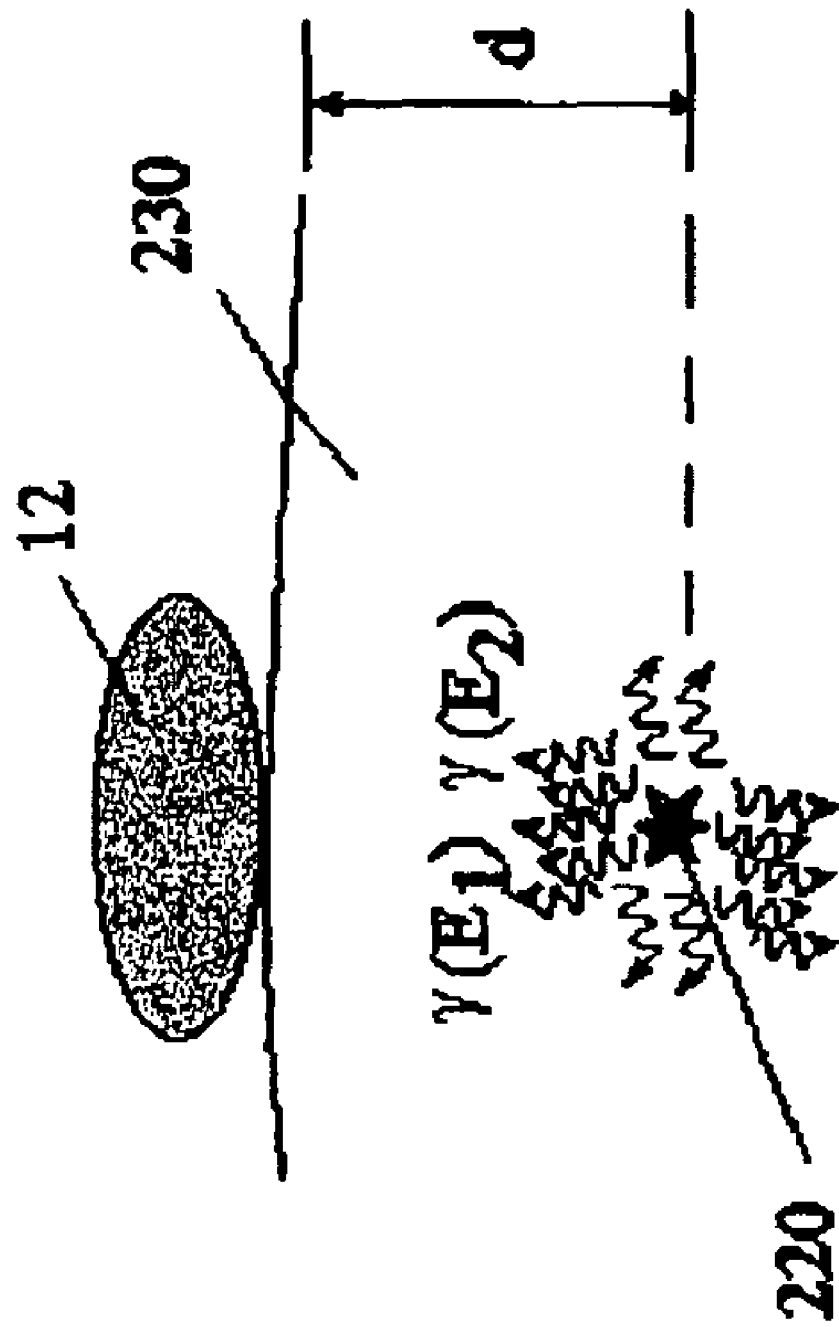
FIG. 24 schematically illustrates a method of calculating the depth of a radiation source, in accordance with a preferred embodiment of the present invention.

Referring further to the drawings, FIG. 24 schematically illustrates a method of calculating the depth, d, of a radiation source 220, based on the attenuation of photons of different energies, which are emitted from the same source 220, within tissue layer 212, by ingestible device 12, in accordance with a preferred embodiment of the present invention.

The transmitted intensity of a monochromatic gamma-ray beam of photon energy E and intensity $I_0$ crossing a) absorbing layer, such as tissue layer 212, of a depth d, is a function of the following: the photons energy E, the layer thickness d, and the total linear attenuation coefficient as a function of energy, $\mu_{total}$, of the material constituting the layer. The transmitted intensity is given by:

$$I(E) = I_0(E) \exp(-\mu_{total}(E) d) \qquad \text{(Eq-1)}$$

The linear attenuation coefficient is expressed in $cm^{-1}$ and is obtained by multiplying the cross section (in $cm^2/gr$) with the absorbing medium density. The total linear attenuation coefficient accounts for absorption due to all the relevant interaction mechanisms: photoelectric effect, Compton scattering, and pair production.

The layer thickness d, which is the depth of the radiation source, can be measured using a radionuclide that emits two or more photon energies, since attenuation is a function of the photon energy.

For photons of different energies, originating from a same source, and having the same half-life, we get:

$$\frac{I(E_1)}{I(E_2)} = \frac{I_0(E_1)}{I_0(E_2)} \cdot \frac{e^{-\mu(E_1) d}}{e^{-\mu(E_2) d}} \qquad \text{(Eq-2)}$$

$$A = \frac{I(E_1)}{I(E_2)} \ \& \ B = \frac{I_0(E_1)}{I_0(E_2)} \qquad \text{(Eq-3)}$$

$$R = \frac{A}{B} = \frac{[I(E_1)/I(E_2)]}{[I_0(E_1)/I_0(E_2)]} \qquad \text{(Eq-4)}$$

-continued $$A = B \cdot \frac{e^{-\mu(E_1)\cdot d}}{e^{-\mu(E_2)\cdot d}} \Rightarrow R = \frac{e^{-\mu(E_1)\cdot d}}{e^{-\mu(E_2)\cdot d}} \quad \text{(Eq-5)}$$

$$R = e^{\{\mu(E_2)-\mu(E_1)\}d} \Rightarrow \ln(R) = [\mu(E_2)-\mu(E_1)]d \quad \text{(Eq-6)}$$

The source depth, d, can be calculated as:

$$d = \frac{\ln(R)}{\mu(E_2)-\mu(E_1)} = \frac{\ln\{[I(E_1)/I(E_2)]/[I_0(E_1)/I_0(E_2)]\}}{\mu(E_2)-\mu(E_1)} \quad \text{(Eq-7)}$$

The linear attenuation coefficients for specific energies are calculated from the photon mass attenuation and energy absorption coefficients table.

The ratio $I_0(E_1)/I_0(E_2)$ for a known isotope or isotopes is calculated from an isotope table and the ratio $I(E_1)/I(E_2)$ is measured at the inspected object edges.

Additionally, X-ray information, for example, mammography may be used, for more material linear attenuation coefficient, since X-ray imaging provides information about the material density.

For example, we may consider a lesion inside a soft tissue, such as a breast, at a distance d that holds an isotope of $^{123}$I, which emits two main photons, as follows:

$E_1$=27 keV with 86.5%; and
$E_2$=159 keV with 83.4%.

The soft tissue density is 0.8 g/cm$^3$.

The linear attenuation coefficients for $E_1$ and $E_2$ are calculated from J. H Hubbell, "Photon Mass Attenuation and Energy—absorption Coefficients from 1 keV to 20 MeV". Int. J. Appl. Radiat Isat. Vol. 33. pp. 1269 to 1290, 1982, as follows:

$\mu(E_1)$=(0.474 cm/g→$\mu(E_1)$=0.474 cm/g·0.8 g/cm$^3$=0.38 l/cm $\mu(E_2)$=0.1489 cm/g→$\mu(E_2)$=0.1489 cm/g·0.8 g/cm$^3$=0.119 l/cm

The measured ratio between $I(E_1)$ to $I(E_2)$ on the attenuating soft tissue edge is 0.6153.

Using Eq-7, one gets that the lesion depth is: d=2 cm.

Alternatively, if the measured ration between $I(E_1)$ to $I(E_2)$ is 0.473 the extracted lesion depth is; d=3 cm.

It will be appreciated that when two or more isotopes used for obtaining the different photons, corrections for their respective half-lives may be required.

It will be appreciated that by calculating the depth of a radiation source at each position, one may obtain a radiation source depth map, with respect to the gastrointestinal, track, as ingestible device 12 travels through it. This information may be superimposed on a radiation source image, as produced by other methods. For example, a radiation source image produced by deconvolution algorithms may be superimposed on a radiation source image produced by depth calculations, based on the attenuation of photons of different energies.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A system for diagnosing a gastrointestinal tract, comprising:
   (a) an ingestible device, sized to be swallowed and arranged for traveling within a gastrointestinal tract of a body, comprising:
      (i) a probe, operative to acquire, along said gastrointestinal tract, a diagnostic image of nuclear radiation of a radiopharmaceutical;
      (ii) data-handling apparatus, in signal communication with said probe, for receiving and handling imaging data, generated by said probe;
      (iii) a power source, for powering said probe and data-handling apparatus; and
      (iv) a shell, which encapsulates said probe, data-handling apparatus, and power source within,
      wherein said ingestible device comprises a plurality of nuclear-radiation detectors, arranged around said probe, and
   (b) first circuitry comprising at least one sensor adapted to determine the location and orientation of the ingestible device in the gastrointestinal tract; and
   (c) second circuitry adapted to reconstruct the diagnostic image based on said location and orientation.

2. The system of claim 1, wherein at least one of said nuclear-radiation detectors is arranged for detecting gamma and beta radiation.

3. The system of claim 2, wherein said at least one nuclear-radiation detector is gated substantially to a photon energy associated with a particular radioisotope.

4. The system of claim 2, wherein said at least one nuclear-radiation detector is gated substantially to at least two photon energies associated with two particular radioisotopes.

5. The system of claim 1, wherein some of said plurality of nuclear-radiation detectors may be gated substantially to a photon energy associated with a specific radioisotope, while others may be gated substantially to a photon energy associated with a different radioisotope.

6. The system of claim 2, wherein said at least one nuclear-radiation detector is not collimated, to detect nuclear radiation impinging at any angle.

7. The system of claim 1, wherein said ingestible device is arranged as a compton camera.

8. A method of nuclear imaging, comprising:
   (1) providing a system for diagnosing a gastrointestinal tract, comprising:
      (a) an ingestible device, sized to be swallowed and arranged for traveling within a gastrointestinal tract of a body, comprising:
         (i) a probe, operative to acquire, along said gastrointestinal tract, a diagnostic image of nuclear radiation of a radiopharmaceutical;

(ii) data-handling apparatus, in signal communication with said probe, for receiving and handling imaging data, generated by said probe;
(iii) a power source, for powering said probe and data-handling apparatus; and
(iv) a shell, which encapsulates said probe, data-handling apparatus, and power source within,
wherein said ingestible device comprises a plurality of nuclear radiation detectors, arranged around said probe, and
(b) first circuitry comprising at least one sensor adapted to determine the location and orientation of the ingestible device in the gastrointestinal tract and
(c) second circuitry adapted to reconstruct the diagnostic image based on said location and orientation;
(2) scanning a radioactivity emitting source of at least two photon energies with said ingestible device, and obtaining a count rate for the at least two photons;
(3) monitoring the position of the ingestible device using said first circuitry; and
(4) calculating the depth of the radioactivity emitting source, at each position, based on the different attenuation of photons of different energies, emitted from the radioactivity emitting source.

9. The method of claim 8, and further including constructing an image of the radioactivity emitting source.

10. The method of claim 8, wherein the monitoring takes place at very short time intervals of between 100 and 200 milliseconds.

11. The method of claim 8, wherein said nuclear-radiation detector is not collimated, to detect nuclear radiation impinging at any angle.

12. The method of claim 8, and further including image reconstruction by deconvolution algorithms.

13. The method of claim 8, wherein said ingestible device comprises a nuclear-radiation detector, arranged for detecting gamma and beta radiation.

14. The method of claim 8, wherein said plurality of nuclear-radiation detectors are arranged around the external surface of said ingestible device, for detecting gamma and beta radiation.

15. A method of diagnosing a gastrointestinal tract, the method comprising:
(1) providing a system for diagnosing a gastrointestinal tract, comprising:
(a) an ingestible device, sized to be swallowed and arranged for traveling within a gastrointestinal tract of a body, comprising:
(i) a probe, operative to acquire, along said gastrointestinal tract, a diagnostic image of nuclear radiation of a radiopharmaceutical;
(ii) data-handling apparatus, in signal communication with said probe, for receiving and handling imaging data, generated by said probe;
(iii) a power source, for powering said probe and data-handling apparatus; and
(iv) a shell, which encapsulates said probe, data-handling apparatus, and power source within,
wherein said ingestible device comprises a plurality of nuclear radiation detectors, arranged around said probe, and
(b) first circuitry comprising at least one sensor adapted to determine the location and orientation of the ingestible device in the gastrointestinal tract and
(c) second circuitry adapted to reconstruct the diagnostic image based on said location and orientation;
(2) inserting said ingestible device comprising a probe and a sensor into a gastrointestinal tract of a body;
(3) collecting diagnostic imaging data along said gastrointestinal tract by detecting nuclear radiation of a radiopharmaceutical using said plurality of nuclear radiation detectors
(4) determining the location and orientation of the ingestible device in the gastrointestinal tract by said first circuitry; and
(5) reconstructing a diagnostic image from said collected imaging data based on said location and orientation.

16. A system according to claim 1 wherein said ingestible device is shaped as a pill.

17. A system according to claim 1, wherein said ingestible device further comprises a transmitter for transmitting data to said at least one sensor, wherein the at least one sensor determines the location and orientation of the ingestible device in the gastrointestinal tract based on said data.

* * * * *